(12) United States Patent
Altieri

(10) Patent No.: US 6,943,150 B1
(45) Date of Patent: Sep. 13, 2005

(54) SURVIVIN, A PROTEIN THAT INHIBITS CELLULAR APOPTOSIS AND ITS MODULATION

(75) Inventor: Dario C. Altieri, Hamden, CT (US)

(73) Assignee: Yale University, New Haven, CT (US)

( * ) Notice: Subject to any disclaimer, the term of this patent is extended or adjusted under 35 U.S.C. 154(b) by 568 days.

(21) Appl. No.: 09/690,825

(22) Filed: Oct. 18, 2000

Related U.S. Application Data

(62) Division of application No. 08/975,080, filed on Nov. 20, 1997, now Pat. No. 6,245,523.
(60) Provisional application No. 60/031,435, filed on Nov. 20, 1996.

(51) Int. Cl.⁷ .......................... C07K 7/06; C07K 7/08; C07K 14/435; C07K 19/00; A61K 38/17
(52) U.S. Cl. ........................ 514/21; 514/12; 514/13; 514/14; 514/15; 530/324; 530/326; 530/327; 530/328
(58) Field of Search ................................. 530/328, 327, 530/326, 324, 350, 358, 828; 514/12, 13, 14, 15, 21, 2

(56) References Cited

U.S. PATENT DOCUMENTS

| | | | | |
|---|---|---|---|---|
| 6,107,041 A | * | 8/2000 | Korneleuk | |
| 6,277,640 B1 | * | 8/2001 | Bennett et al. | 435/455 |

FOREIGN PATENT DOCUMENTS

| | | |
|---|---|---|
| WO | 95/20655 | 3/1995 |

OTHER PUBLICATIONS

The abstract of Ghosh et al (Accession No. 2003: 837371 Caplus on STN), 2003.*
The abstract of Dumas et al (Accession No. AAG02311, Dgene on STN), 2003.*
Mathews and Van Holde, Biochemistry, 1996, pp. 165–171.*
Matthews, B. Genetic and Structural Analysis of the Protein Stability Problem, In: Perspectives in Biochemistry, 1989, vol. 1, p 6–9, Ed. Hans Neurath.*
Bork, Genome Research, 1998, vol. 10, pp. 398–400.*
The abstract of Aziz et al (Accession No. 2002:833060, Caplus on STN), 2002.*
Skipper et al, Journal of Experimental Medicine, 1996, vol. 183, pp. 527–534.*
Hiraki et al, Clinical Cancer Research, 1999, vol. 5, pp. 933–936.*
Welt and Ritter, Seminars in Oncology, 1999, vol. 26, pp. 683–690.*
Becker et al, International Immunology, 1993, vol. 5, pp. 1501–1508.*
Paul et al, PNAS, 1998, vol. 14, pp. 401–405.*

Ada, Immunology and Cell biology, 1999, vol. 77, pp. 180–185.*
Altieri Dario C., Xa receptor EPR–1, *FASEB J*(1995) 9:860–865.
Ambrosini G. et al., "Molecular Dissection of Effector Cell Protease Receptor–1 Recognition of Factor Xa", the Journal of Biological Chemistry, vol. 271, No. 2, Jan. 12, 1996, p. 1243–1248.
Ambrosini et al., "A Novel Anti–Apoptosis Gene, *Survivin*, Expressed in Cancer and Lymphoma", *Nature Medicine*, vol. 3, No. 8, pp. 917–921 (Aug. 1997).
Birnbaum, M.J. et al., An Apoptosis–inhibiting Gene from a Nuclear Polyhedrosis Virus Encoding a Polypeptide with CYS/HIS Sequence Motifs—*J Virology* (1994) 68:2521–2528.
Clem et al., "Anti–apoptotic Genes of Baculovirus", *Death and Differentiation*, vol. 3, pp. 9–16 (Jan. 1996).
Clem, R.J. et al., Control of Programmed Cell Death by the Baculovirus Gene p35 and iap—*Mol Cell Biol* (1994) 14:5212–5222.
Duchosal, M.A. et al., "In vivo Immunosupresion by Targeting a Novel POrotease Receptor", Letters to Nature, vol. 380, Mar. 28, 1996, pp. 352–356.
Duckett, C.S. et Al., A Conserved Family of Cellular Genes Related to the Baculovirus Iap Gene and Encoding Apoptosis Inhibitors—EMBO J (1996) 15:2685–2694.
Hay, B.A. et al., Drosophila Homologs of Baculovirus Inhibitor of Apoptosis Proteins Function to Block Cell Death—*Cell*(1995) 83:1253–1262.
International Search Report.
Liston, P. et al., Suppression of Apoptosis in Mammalian Cells by Naip and a Related Family of Iap Genes—*Nature* (1996) 379:349–353.
Rothe, M. et al., The TNFR2–TRAF Signaling Complex Contains Two Novel Proteins Related to Baculoviral Inhibitor of Apoptosis Proteins, *Cell*(1995) 83:1243–1252.
Roy, N. et al., the Gene for Neuronal Apoptosis Inhibitory Protein Is Partially Deleted in Individuals with Spinal Muscular Atrophy, *Cell*(1995) 80:167–178.

* cited by examiner

Primary Examiner—Karen A. Canella
(74) Attorney, Agent, or Firm—Morgan Lewis & Bockius LLP

(57) ABSTRACT

The present invention provides the amino acid of a protein that inhibits cellular apoptosis, herein termed the Survivin protein and nucleic acid molecules that encode Survivin. Based on this disclosure, the present invention provides isolated Survivin protein, isolated Survivin encoding nucleic acid molecules, methods of isolating other members of the Survivin family of proteins, methods for identifying agents that block Survivin mediated inhibition of cellular apoptosis, methods of using agents that block Survivin mediated inhibition or Survivin expression to modulate biological and pathological processes, and methods of assaying Survivin activity.

24 Claims, 27 Drawing Sheets

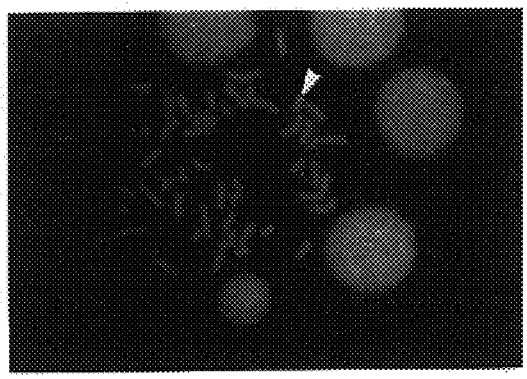
FIG. 1A
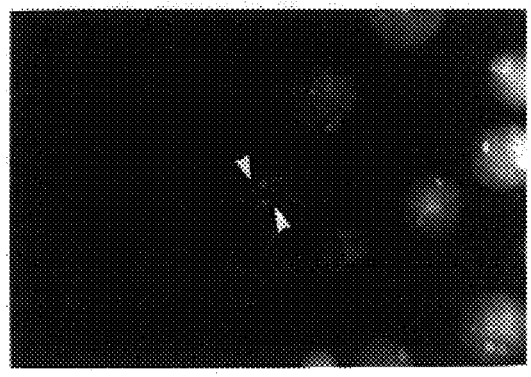
FIG. 1B
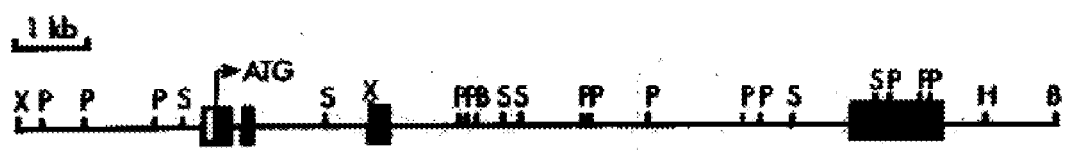
FIG. 1C
| 5' Exon | Intron | 3' Exon |
|---|---|---|
| (2918)GCGG\|GTGAG------- | (3161)CTGTCCCTTGCAG\| | ATGGC |
| (3280)CCAT\|GTAAG------- | (5145)TTGATTTTTCTAG\| | AGAGG |
| (5272)AATT\|GTATG------- | (11942)TCTTTATTTCCAG\| | GCAAA |
FIG. 1D

FIG. 4A

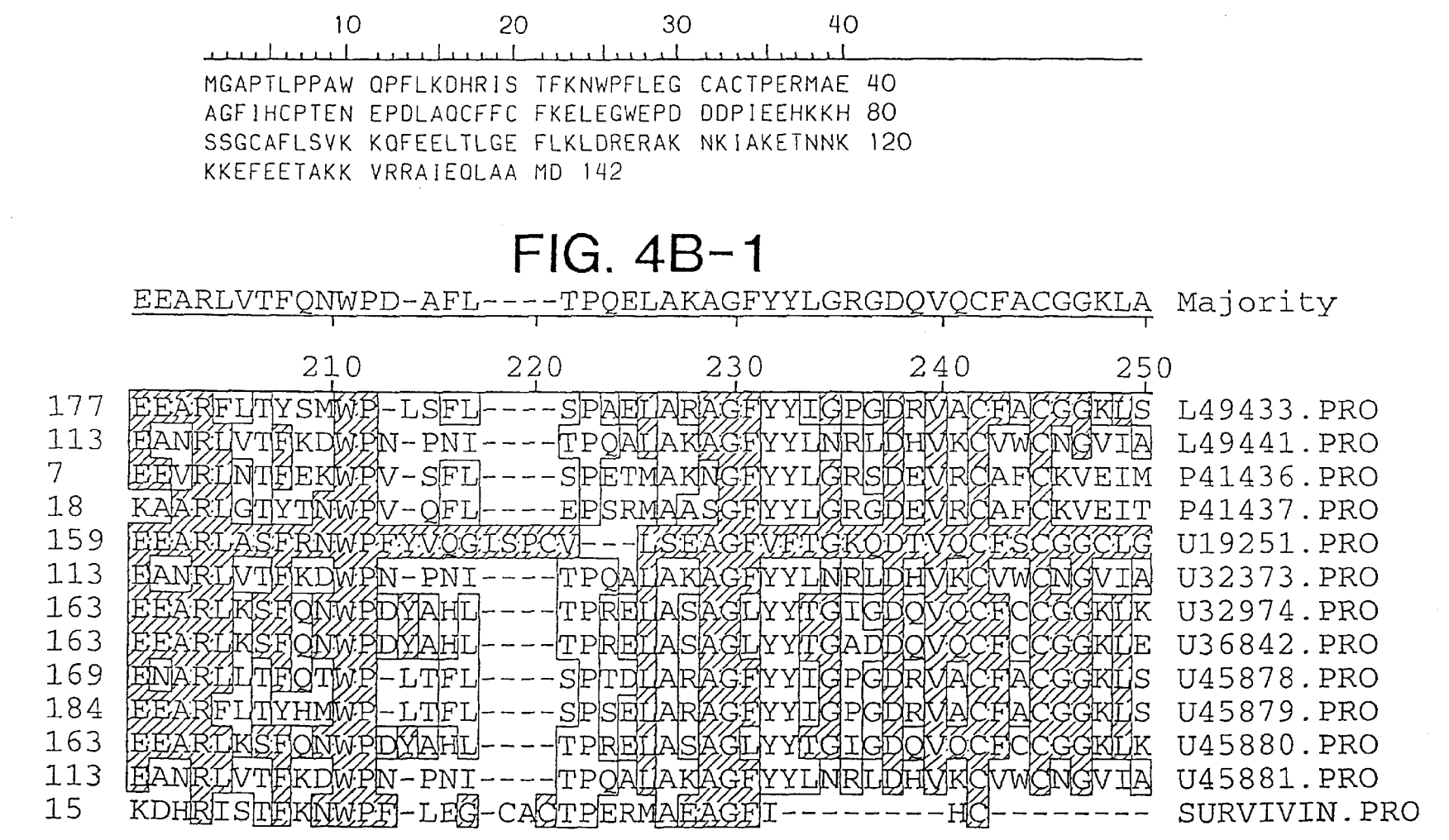

```
         10         20         30         40
         |          |          |          |
MGAPTLPPAW QPFLKDHRIS TFKNWPFLEG CACTPERMAE 40
AGFIHCPTEN EPDLAQCFFC FKELEGWEPD DDPIEEHKKH 80
SSGCAFLSVK KQFEELTLGE FLKLDRERAK NKIAKETNNK 120
KKEFEETAKK VRRAIEQLAA MD 142
```

Survivin

RbIgG

FIG. 5A   FIG. 5B   FIG. 5C

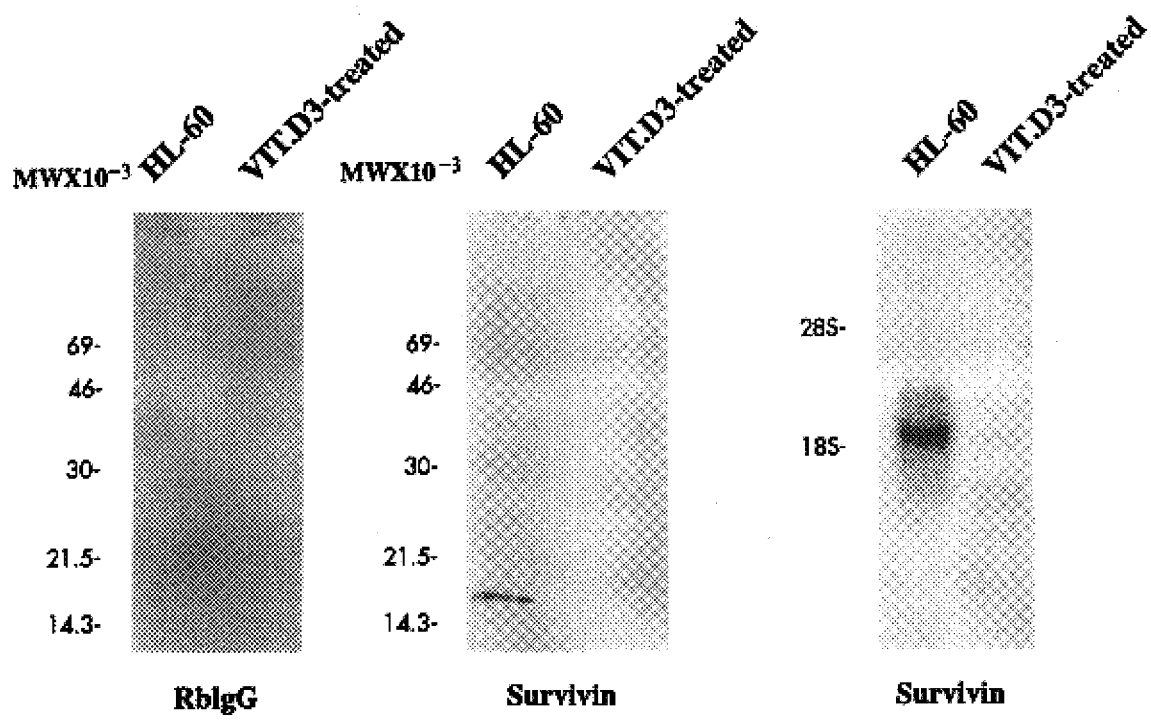
RbIgG  
Immunoblotting  
FIG. 8A
Survivin  
Immunoblotting  
FIG. 8B
Survivin  
Northern Blot  
FIG. 8C
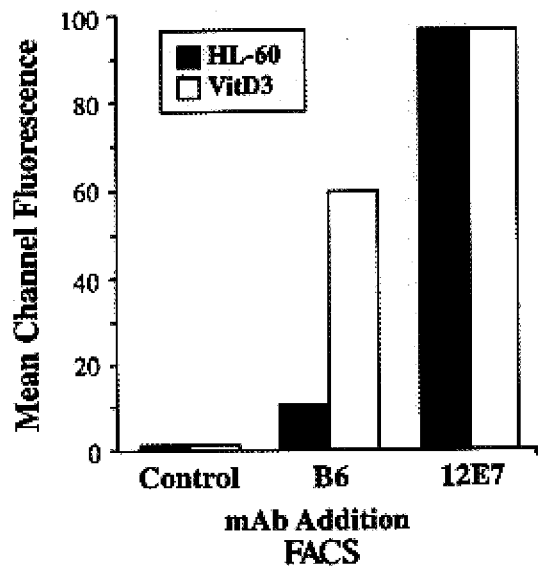
mAb Addition  
FACS
FIG. 8D

FIG. 10A translation=MGAPTLPPAWQPFLKDHRISTFKNWPFLEGCACTPERMAEAGFIHCP
TENEPDLAQCFFCFKELEGWEPDDDPIEEHKKHSSGCAFLSVKKQFEELTLGEFL
KLDRERAKNKIAKETNNKKKEFEETAKKVRRAIEQLAAMD

| | | | | |
|---|---|---|---|---|
| 1 | TCTAGACATG | CGGATATATT | CAAGCTGGGC | ACAGCACAGC | AGCCCCACCC |
| 51 | CAGGCAGCTT | GAAATCAGAG | CTGGGGTCCA | AAGGGACCAC | ACCCCGAGGG |
| 101 | ACTGTGTGGG | GGTCGGGGCA | CACAGGCCAC | TGCTTCCCCC | CGTCTTTCTC |
| 151 | AGCCATTCCT | GAAGTCAGCC | TCACTCTGCT | TCTCAGGGAT | TTCAAATGTG |
| 201 | CAGAGACTCT | GGCACTTTTG | TAGAAGCCCC | TTCTGGTCCT | AACTTACACC |
| 251 | TGGATGCTGT | GGGGCTGCAG | CTGCTGCTCG | GCTCGGGAG | GATGCTGGGG |
| 301 | GCCCGGTGCC | CATGAGCTTT | TGAAGCTCCT | GGAACTCGGT | TTTGAGGGTG |
| 351 | TTCAGGTCCA | GGTGGACACC | TGGGCTGTCC | TTGTCCATGC | ATTTGATGAC |
| 401 | ATTGTGTGCA | GAAGTGAAAA | GGAGTTAGGC | CGGGCATGCT | GGCTTATGCC |
| 451 | TGTAATCCCA | GCACTTTGGG | AGGCTGAGGC | GGGTGGATCA | CGAGGTCAGG |
| 501 | AGTTCAATAC | CAGCCTGGCC | AAGATGGTGA | AACCCCGTCT | CTACTAAAAA |
| 551 | TACAAAAAAA | TTAGCCGGGC | ATGGTGGCGG | GCGCATGTAA | TCCCAGCTAC |
| 601 | TGGGGGGGCT | GAGGCAGAGA | ATTGCTGGAA | CCCAGGAGAT | GGAGGTTGCA |
| 651 | GTGAGCCAAG | ATTGTGCCAC | TGCACTGCAC | TCCAGCCTGG | CGACAGAGCA |
| 701 | AGACTCTGTC | TCAAAAAAAA | AAAAAAAAAG | TGAAAAGGAG | TTGTTCCTTT |
| 751 | CCTCCCTCCT | GAGGGCAGGC | AACTGCTGCG | GTTGCCAGTG | GAGGTGGTGC |
| 801 | GTCCTTGGTC | TGTGCCTGGG | GGCCACCCCA | GCAGAGGCCA | TGGTGGTGCC |
| 851 | AGGGCCCGGT | TAGCGAGCCA | ATCAGCAGGA | CCCAGGGGCG | ACCTGCCAAA |
| 901 | GTCAACTGGA | TTTGATAACT | GCAGCGAAGT | TAAGTTTCCT | GATTTTGATG |
| 951 | ATTGTGTTGT | GGTTGTGTAA | GAGAATGAAG | TATTTCGGGG | TAGTATGGTA |
| 1001 | ATGCCTTCAA | CTTACAAACG | GTTCAGGTAA | ACCACCCATA | TACATACATA |
| 1051 | TACATGCATG | TGATATATAC | ACATACAGGG | ATGTGTGTGT | GTTCACATAT |
| 1101 | ATGAGGGGAG | AGAGACTAGG | GGAGAGAAAG | TAGGTTGGGG | AGAGGGAGAG |
| 1151 | AGAAAGGAAA | ACAGGAGACA | GAGAGAGAGC | GGGGAGTAGA | GAGAGGGAAG |
| 1201 | GGGTAAGAGA | GGGAGAGGAG | GAGAGAAAGG | GAGGAAGAAG | CAGAGAGTGA |
| 1251 | ATGTTAAAGG | AAACAGGCAA | AACATAAACA | GAAAATCTGG | GTGAAGGGTA |
| 1301 | TATGAGTATT | CTTTGTACTA | TTCTTGCAAT | TATCTTTTAT | TTAAATTGAC |
| 1351 | ATCGGGCCGG | GCGCAGTGGC | TCACATCTGT | AATCCCAGCA | CTTTGGGAGG |
| 1401 | CCGAGGCAGG | CAGATCACTT | GAGGTCAGGA | GTTTGAGACC | AGCCTGGCAA |
| 1451 | ACATGGTGAA | ACCCCATCTC | TACTAAAAAT | ACAAAATTA | GCCTGGTGTG |
| 1501 | GTGGTGCATG | CCTTTAATCT | CAGCTACTCG | GGAGGCTGAG | GCAGGAGAAT |
| 1551 | CGCTTGAACC | CGTGGCGGGG | AGGAGGTTGC | AGTGAGCTGA | GATCATGCCA |
| 1601 | CTGCACTCCA | GCCTGGGCGA | TAGAGCGAGA | CTCAGTTTCA | AATAAATAAA |
| 1651 | TAAACATCAA | AATAAAAGT | TACTGTATTA | AAGAATGGGG | GCGGGGTGGG |
| 1701 | AGGGGTGGGG | AGAGGTTGCA | AAAATAAATA | AATAAATAAA | TAAACCCCAA |
| 1751 | AATGAAAAAG | ACAGTGGAGG | CACCAGGCCT | GCGTGGGGCT | GGAGGGCTAA |
| 1801 | TAAGGCCAGG | CCTCTTATCT | CTGGCCATAG | AACCAGAGAA | GTGAGTGGAT |
| 1851 | GTGATGCCCA | GCTCCAGAAG | TGACTCCAGA | ACACCCTGTT | CCAAAGCAGA |
| 1901 | GGACACACTG | ATTTTTTTT | TAATAGGCTG | CAGGACTTAC | TGTTGGTGGG |
| 1951 | ACGCCCTGCT | TTGCGAAGGG | AAAGGAGGAG | TTTGCCCTGA | GCACAGGCCC |
| 2001 | CCACCCTCCA | CTGGGCTTTC | CCCAGCTCCC | TTGTCTTCTT | ATCACGGTAG |
| 2051 | TGGCCCAGTC | CCTGGCCCCT | GACTCCAGAA | GGTGGCCCTC | CTGGAAACCC |
| 2101 | AGGTCGTGCA | GTCAACGATG | TACTCGCCGG | ACAGCGATG | TCTGCTGCAC |
| 2151 | TCCATCCCTC | CCTGTTCAT | TTGTCCTTCA | TGCCCGTCTG | GAGTAGATGC |

FIG. 10B

```
2201    TTTTTGCAGA GGTGGCACCC TGTAAAGCTC TCCTGTCTGA CTTTTTTTTT
2251    TTTTTTAGAC TGAGTTTTGC TCTTGTTGCC TAGGCTGGAG TGCAATGGCA
2301    CAATCTCAGC TCACTGCACC CTCTGCCTCC CGGGTTCAAG CGATTCTCCT
2351    GCCTCAGCCT CCCGAGTAGT TGGGATTACA GGCATGCACC ACCACGCCCA
2401    GCTAATTTTT GTATTTTTAG TAGAGACAAG GTTTCACCGT GATGGCCAGG
2451    CTGGTCTTGA ACTCCAGGAC TCAAGTGATG CTCCTGCCTA GGCCTCTCAA
2501    AGTGTTGGGA TTACAGGCGT GAGCCACTGC ACCCGGCCTG CACGCGTTCT
2551    TTGAAAGCAG TCGAGGGGGC GCTAGGTGTG GGCAGGACG AGCTGGCGCG
2601    GCGTCGCTGG GTGCACCGCG ACCACGGGCA GAGCCACGCG GCGGGAGGAC
2651    TACAACTCCC GGCACACCCC GCGCCGCCCC GCCTCTACTC CCAGAAGGCC
2701    GCGGGGGGTG GACCGCCTAA GAGGGCGTGC GCTCCCGACA TGCCCCGCGG
2751    CGCGCCATTA ACCGCCAGAT TTGAATCGCG GGACCCGTTG GCAGAGGTGG
               |————▶Start
2801    CGGCGGCGGC ATGGGTGCCC CGACGTTGCC CCCTGCCTGG CAGCCCTTTC
2851    TCAAGGACCA CCGCATCTCT ACATTCAAGA ACTGGCCCTT CTTGGAGGGC
2901    TGCGCCTGCA CCCCGGAGCG GGTGAGACTG CCCGGCCTCC TGGGGTCCCC
2951    CACGCCCGCC TTGCCCTGTC CCTAGCGAGG CCACTGTGAC TGGGCCTCGG
3001    GGGTACAAGC CGCCCTCCCC TCCCCGTCCT GTCCCCAGCG AGGCCACTGT
3051    GGCTGGGCCC CTTGGGTCCA GGCCGGCCTC CCCTCCCTGC TTTGTCCCCA
3101    TCGAGGCCTT TGTGGCTGGG CCTCGGGGTT CCGGGCTGCC ACGTCCACTC
3151    ACGAGCTGTG CTGTCCCTTG CAGATGGCCG AGGCTGGCTT CATCCACTGC
3201    CCCACTGAGA ACGAGCCAGA CTTGGCCCAG TGTTTCTTCT GCTTCAAGGA
3251    GCTGGAAGGC TGGGAGCCAG ATGACGACCC CATGTAAGTC TTCTCTGGCC
3301    AGCCTCGATG GGCTTTGTTT TGAACTGAGT TGTCAAAAGA TTTGAGTTGC
3351    AAAGACACTT AGTATGGGAG GGTTGCTTTC CACCCTCATT GCTTCTTAAA
3401    CAGCTGTTGT GAACGGATAC CTCTCTATAT GCTGGTGCCT TGGTGATGCT
3451    TACAACCTAA TTAAATCTCA TTTGACCAAA ATGCCTTGGG GTGGACGTAA
3501    GATGCCTGAT GCCTTTCATG TTCAACAGAA TACATCAGCA GACCCTGTTG
3551    TTGTGAACTC CCAGGAATGT CCAAGTGCTT TTTTTGAGAT TTTTTAAAAA
3601    ACAGTTTAAT TGAAATATAA CCTACACAGC ACAAAAATTA CCCTTTGAAA
3651    GTGTGCACTT CACACTTTCG GAGGCTGAGG CGGGCGGATC ACCTGAGGTC
3701    AGGAGTTCAA GACCTGCCTG CCAACTTGG CGAAACCCCG TCTCTACTAA
3751    AAATACAAAA ATTAGCCGGG CATGGTAGCG CACGCCCGTA ATCCCAGCTA
3801    CTCGGGAGGC TAAGGCAGGA GAATCGCTTG AACCTGGGAG GCGGAGGTTG
3851    CAGTGAGCCG AGATTGTGCC AATGCACTCC AGCCTCGGCG ACAGAGCGAG
3901    ACTCCGTCAT AAAAATAAAA AATTGAAAAA AAAAAAGAA AGAAAGCATA
3951    TACTTCAGTG TTGTTCTGGA TTTTTTTCTT CAAGATGCCT AGTTAATGAC
4001    AATGAAATTC TGTACTCGGA TGGTATCTGT CTTTCCACAC TGTAATGCCA
4051    TATTCTTTTC TCACCTTTTT TTCTGTCGGA TTCAGTTGCT TCCACAGCTT
4101    TAATTTTTTT CCCCTGGAGA TCTTAGTATG TTTGCTATGG TGGTTATACT
4151    GCATCCCCGT AATCACTGGG AAAAGATCAG TGGTATTCTT CTTGAAAATG
4201    AATAAGTGTT ATGATATTTT CAGATTAGAG TTACAACTGG CTGTCTTTTT
4251    GGACTTTGTT TGGCCATGTT TTCATTGTAA TGCAGTTCTG GTAACGGTGA
4301    TAGTCAGTTA TACAGGAGA CTCCCCTAGC AGAAAATGAG AGTGTGAGCT
4351    AGGGGGTCCC TTGGGGAACC CGGGGCAATA ATGCCCTTCT CTGCCCTTAA
4401    TCCTTACAGT GGGCCGGGCA CGGTGGCTTA CGCCTGTAAT ACCAGCACTT
4451    TGGGAGGCCG AGGCGGGCGG ATCACGAGGT CAGGAGATCG AGACCATCTT
4501    GGCTAATACG GTGAAACCCC GTCTCCACTA AAAATACAAA AAATTAGCCG
```

FIG. 10C

```
4551    GGCGTGGTGG TGGGCGCCTG TAGTCCCAGC TACTCGGGAG GCTGAGGCAG
4601    GAGAATGGCG TGAACCCAGG AGGCGGAGCT TGCAGTGAGC CGAGATTGCA
4651    CCACTGCACT CCAGCCTGGG CGACAGAATG AGACTCCGTC TCAAAAAAAA
4701    AAAAAAAGA  AAAAAATCTT TACAGTGGAT TACATAACAA TTCCAGTGAA
4751    ATGAAATTAC TTCAAACAGT TCCTTGAGAA TGTTGGAGGG ATTTGACATG
4801    TAATTCCTTT GGACATATAC CATGTAACAC TTTTCCAACT AATTGCTAAG
4851    GAAGTCCAGA TAAAATAGAT ACATTAGCCA CACAGATGTG GGGGAGATG
4901    TCCACAGGGA GAGAGAAGGT GCTAAGAGGT GCCATATGGG AATGTGGCTT
4951    GGGCAAAGCA CTGATGCCAT CAACTTCAGA CTTGACGTCT TACTCCTGAG
5001    GCAGAGCAGG GTGTGCCTGT GGAGGGCGTG GGGAGGTGGC CCGTGGGGAG
5051    TGGACTGCCG CTTTAATCCC TTCAGCTGCC TTTCCGCTGT TGTTTTGATT
5101    TTTCTAGAGA GGAACATAAA AAGCATTCGT CCGGTTGCGC TTTCCTTTCT
5151    GTCAAGAAGC AGTTTAAGA  ATTAACCCTT GGTGAATTTT TGAAACTGGA
5201    CAGAGAAAGA GCCAAGAACA AAATTGTATG TATTGGGAAT AAGAACTGCT
5251    CAAACCCTGT TCAATGTCTT TAGCACTAAA CTACCTAGTC CCTCAAAGGG
5301    ACTCTGTGTT TTCCTCAGGA AGCATTTTTT TTTTTTTTCT GAGATAGAGT
5351    TTCACTCTTG TTGCCCAGGC TGGAGTGCAA TGGTGCAATC TTGGCTCACT
5401    GCAACCTCTG CCTCTCGGGT TCAAGTGATT CTCCTGCCTC AGCCTCCCAA
5451    GTAACTGGGA TTACAGGGAA GTGCCACCAC ACCCAGCTAA TTTTTGTATT
5501    TTTAGTAGAG ATGGGGTTTC ACCACATTGC CCAGGCTGGT CTTGAACTCC
5551    TGACCTCGTG ATTCGCCCAC CTTGGCCTCC CAAAGTGCTG GGATTACAGG
5601    CGTGAACCAC CACGCCTGGC TTTTTTTTTT TTGTTCTGAG ACACAGTTTC
5651    ACTCTGTTAC CCAGGCTGGA GTAGGGTGGC CTGATCTCGG ATCACTGCAA
5701    CCTCCGCCTC CTGGGCTCAA GTGATTTGCC TGCTTCAGCC TCCCAAGTAG
5751    CCGAGATTAC AGGCATGTGC CACCACACCC AGGTAATTTT TGTATTTTTG
5801    GTAGAGACGA GGTTTCACCA TGTTGGCCAG GCTGGTTTTG AACTCCTGAC
5851    CTCAGGTGAT CCACCCGCCT CAGCCTCCCA AAGTGCTGAG ATTATAGGTG
5901    TGAGCCACCA CACCTGGCCT CAGGAAGTAT TTTTATTTTT AAATTTATTT
5951    ATTTATTTGA GATGGAGTCT TGCTCTGTCG CCCAGGCTAG AGTGCAGCGA
6001    CGGGATCTCG GCTCACTGCA AGCTCCGCCC CCCAGGTTCA AGCCATTCTC
6051    CTGCCTCAGC CTCCCGAGTA GCTGGGACTA CAGGCGCCCG CCACCACACC
6101    CGGCTAATTT TTTTGTATTT TTAGTAGAGA CGGGTTTTCA CCGTGTTAGC
6151    CAGGAGGGTC TTGATCTCCT GACCTCGTGA TCTGCCTGCC TCGGCCTCCC
6201    AAAGTGCTGG GATTACAGGT GTGAGCCACC ACACCCGGCT ATTTTTATTT
6251    TTTGAGACA  GGGACTCACT CTGTCACCTG GGCTGCAGTG CAGTGGTACA
6301    CCATAGCTCA CTGCAGCCTC GAACTCCTGA GCTCAAGTGA TCCTCCCACC
6351    TCATCCTCAC AAGTAATTGG GACTACAGGT GCACCCCACC ATGCCCACCT
6401    AATTTATTTA TTTATTTATT TATTTATTTT CATAGAGATG AGGGTTCCCT
6451    GTGTTGTCCA GGCTGGTCTT GAACTCCTGA GCTCACGGGA TCCTTTTGCC
6501    TGGGCCTCCC AAAGTGCTGA GATTACAGGC ATGAGCCACC GTGCCCAGCT
6551    AGGAATCATT TTTAAAGCCC CTAGGATGTC TGTGTGATTT TAAAGCTCCT
6601    GGAGTGTGGC CGGTATAAGT ATATACCGGT ATAAGTAAAT CCCACATTTT
6651    CTGGGCTTTA TTTATTTATT TATTTATTTA TTTATTTTTA ATTTTTTTTT
6701    TTGAGACGAG TCTCACTTTG TCACCCAGGC TGGAGTGCAG TGGCACGATC
6751    TCGGCTCACT GCAACCTCTG CCTCCGGGG  TCAAGCGATT CTCCTGCCTT
6801    AGCCTCCCGA GTAGCTGGGA CTACAGGCAC GCACCACCAT GCCTGGCTAA
6851    TTTTTGTATT TTTAGTAGAC GGGGTTTCAC CATGCTGGCC AAGCTGGTCT
6901    CAAACTCCTG ACCTTGTGAT CTGCCCGCTT TAGCCTCCCA GAGTGCTGGG
```

FIG. 10D

```
6951  ATTACAGGCA TGAGCCACCA TGCGTGGTCT TTTTAAAATT TTTTGATTTT
7001  TTTTTTTTTT GAGACAGAGC CTTGCTCTGT CGCCCAGGCT GGAGTGCAGT
7051  GGCACGATCT CAGCTCACTA CAAGCTCCGC CTCCCGGGTT CACGCCATTC
7101  TTCTGCCTCA GCCTCCTGAG TAGCTGGGAC TACAGGTGCC CACCACCACG
7151  CCTGGCTAAT TTTTTTGGT ATTTTTATTA GAGACAAGGT TTCATCATGT
7201  TGGCCAGGCT GGTCTCAAAC TCCTGACCTC AAGTGATCTG CCTGCCTCGG
7251  CCTCCCAAAG CGCTGAGATT ACAGGTGTGA TCTACTGCGC CAGGCCTGGG
7301  CGTCATATAT TCTTATTTGC TAAGTCTGGC AGCCCACAC AGAATAAGTA
7351  CTGGGGGATT CCATATCCTT GTAGCAAAGC CCTGGGTGGA GAGTCAGGAG
7401  ATGTTGTAGT TCTGTCTCTG CCACTTGCAG ACTTTGAGTT TAAGCCAGTC
7451  GTGCTCATGC TTTCCTTGCT AAATAGAGGT TAGACCCCCT ATCCCATGGT
7501  TTCTCAGGTT GCTTTTCAGC TTGAAAATTG TATTCCTTTG TAGAGATCAG
7551  CGTAAAATAA TTCTGTCCTT ATATGTGGCT TTATTTTAAT TTGAGACAGA
7601  GTGTCACTCA GTCGCCCAGG CTGGAGTGTG GTGGTGCGAT CTTGGCTCAC
7651  TGCGACCTCC ACCTCCAGG TTCAAGCGAT TCTCGTGCCT CAGGCTCCCA
7701  AGTAGCTGAG ATTATAGGTG TGTGCCACCA GGCCCAGCTA ACTTTTGTAT
7751  TTTTAGTAGA GACAGGGTTT TGCCATGTTG GCTAAGCTGG TCTCGAACTC
7801  CTGGCCTCAA GTGATCTGCC CGCCTTGGCA TCCCAAAGTG CTGGGATTAC
7851  AGGTGTGAAC CACCACACCT GGCCTCAATA TAGTGGCTTT TAAGTGCTAA
7901  GGACTGAGAT TGTGTTTTGT CAGGAAGAGG CCAGTTGTGG GTGAAGCATG
7951  CTGTGAGAGA GCTTGTCACC TGGTTGAGGT TGTGGGAGCT GCAGCGTGGG
8001  AACTGGAAAG TGGGCTGGGG ATCATCTTTT TCCAGGTCAG GGGTCAGCCA
8051  GCTTTTCTGC AGCGTGCCAT AGACCATCTC TTAGCCCTCG TGGGTCAGAG
8101  TCTCTGTTGC ATATTGTCTT TTGTTGTTTT TCACAACCTT TTAGAAACAT
8151  AAAAAGCATT CTTAGCCCGT GGGCTGGACA AAAAAAGGCC ATGACGGGCT
8201  GTATGGATTT GGCCCAGCAG GCCCTTGCTT GCCAAGCCCT GTTTTAGACA
8251  AGGAGCAGCT TGTGTGCCTG GAACCATCAT GGGCACAGGG GAGGAGCAGA
8301  GTGGATGTGG AGGTGTGAGC TGGAAACCAG GTCCCAGAGC GCTGAGAAAG
8351  ACAGAGGGTT TTTGCCCTTG CAAGTAGAGC AACTGAAATC TGACACCATC
8401  CAGTTCCAGA AAGCCCTGAA GTGCTGGTGG ACGCTGCGGG GTGCTCCGCT
8451  CTAGGGTTAC AGGGATGAAG ATGCAGTCTG GTAGGGGAG TCCACTCACC
8501  TGTTGGAAGA TGTGATTAAG AAAAGTAGAC TTTCAGGGCC GGGCATGGTG
8551  GCTCACGCCT GTAATCCCAG CACTTTGGGA GGCCGAGGCG GGTGGATCAC
8601  GAGGTCAGGA GATCGAGACC ATCCTGGCTA ACATGGTGAA ACCCCGTCTT
8651  TACTAAAAAT ACAAAAAATT AGCTGGGCGT GGTGGCGGGC GCCTGTAGTC
8701  CCAGCTACTC GGGAGGCTGA GGCAGGAGAA TGGCGTGAAC CTGGGAGGTG
8751  GAGCTTGCTG TGAGCCGAGA TCGCGCCACT GCACTCCAGC CTGGGCGACA
8801  GAGCGAGACT CCGTCTCAAA AAAAAAAAA AAAGTAGGCT TTCATGATGT
8851  GTGAGCTGAA GGCGCAGTAG GCAGAAGTAG AGGCCTCAGT CCCTGCAGGA
8901  GACCCCTCGG TCTCTATCTC CTGATAGTCA GACCCAGCCA CACTGGAAAG
8951  AGGGAGACA TTACAGCCTG CGAGAAAAGT AGGGAGATTT AAAAACTGCT
9001  TGGCTTTTAT TTTGAACTGT TTTTTTTGTT TGTTTGTTTT CCCCAATTCA
9051  GAATACAGAA TACTTTATG GATTTGTTTT TATTACTTTA ATTTTGAAAC
9101  AATATAATCT TTTTTTTGTT GTTTTTTGA GACAGGGTCT TACTCTGTCA
9151  CCCAGGCTGA GTGCAGTGGT GTGATCTTGG CTCACCTCAG CCTCGACCCC
9201  CTGGGCTCAA ATGATTCTCC CACCTCAGCT TCCCAAGTAG CTGGGACCAC
9251  AGGTGCGTGT GTTGCGCTAT ACAAATCCTG AAGACAAGGA TGCTGTTGCT
9301  GGTGATGCTG GGGATTCCCA AGATCCCAGA TTTGATGGCA GGATGCCCCT
```

FIG. 10E

```
9351   GTCTGCTGCC TTGCCAGGGT GCCAGGAGGG CGCTGCTGTG GAAGCTGAGG
9401   CCCGGCCATC CAGGGCGATG CATTGGGCGC TGATTCTTGT TCCTGCTGCT
9451   GCCTCGGTGC TTAGCTTTTG AAACAATGAA ATAAATTAGA ACCAGTGTGA
9501   AAATCGATCA GGGAATAAAT TTAATGTGGA ATAAACTGA ACAACTTAGT
9551   TCTTCATAAG AGTTTACTTG GTAAATACTT GTGATGAGGA CAAAACGAAG
9601   CACTAGAAGG AGAGGCGAGT TGTAGACCTG GGTGGCAGGA GTGTTTTGTT
9651   TGTTTTCTTT GGCAGGGTCT TGCTCTGTTG CTCAGGCTGG AGTACAGTGG
9701   CACAATCACA GCTCACTATA GCCTCGACCT CCTGGACTCA AGCAATCCTC
9751   CTGCCTCAGC CTCCCAGTAG CTGGGACTAC AGGCGCATGC CACCATGCCT
9801   GGCTAATTTT AAATTTTTTT TTTTCTCTTT TTTGAGATGG AATCTCACTC
9851   TGTCGCCCAG GCTGGAGTGC AGTGGCGTGA TCTCGGCTGA CGGCAAGCTC
9901   CGCCTCCCAG GTTCACTCCA TTCGCCTGCC TCAGCCTCCC AAGTAGCTGG
9951   GACTACAGGC GCTGGGATTA CAAACCCAAA CCCAAAGTGC TGGGATTACA
10001  GGCGTGAGCC ACTGCACCCG GCCTGTTTTG TCTTTCAATA GCAAGAGTTG
10151  TGTTTGCTTC GCCCCTACCT TTAGTGGAAA AATGTATAAA ATGGAGATAT
10201  TGACCTCCAC ATTGGGGTGG TTAAATTATA GCATGTATGC AAAGGAGCTT
10251  CGCTAATTTA AGGCTTTTTT GAAAGAGAAG AAACTGAATA ATCCATGTGT
10301  GTATATATAT TTTAAAAGCC ATGGTCATCT TTCCATATCA GTAAAGCTGA
10351  GGCTCCTGG GACTGCAGAG TTGTCCATCA CAGTCCATTA TAAGTGCGCT
10401  GCTGGGCCAG GTGCAGTGGC TTGTGCCTGA ATCCCAGCAC TTTGGGAGGC
10451  CAAGGCAGGA GGATTCATTG AGCCCAGGAG TTTTGAGGCG AGCCTGGGCA
10501  ATGTGGCCAG ACCTCATCTC TTCAAAAAAT ACACAAAAAA TTAGCCAGGC
10551  ATGGTGGCAC GTGCCTGTAG TCTCAGCTAC TCAGGAGGCT GAGGTGGGAG
10601  GATCACTTTG AGCCTTGCAG GTCAAAGCTG CAGTAAGCCA TGATCTTGCC
10651  ACTGCATTCC AGCCTGGATG ACAGAGCGAG ACCCTGTCTC TAAAAAAAAA
10701  AAAAACCAAA CGGTGCACTG TTTTCTTTTT TCTTATCAAT TTATTATTTT
10751  TAAATTAAAT TTTCTTTTAA TAATTTATAA ATTATAAATT TATATTAAAA
10801  AATGACAAAT TTTTATTACT TATACATGAG GTAAAACTTA GGATATATAA
10851  AGTACATATT GAAAAGTAAT TTTTTGGCTG GCACAGTGGC TCACACCTGT
10901  AATCCCAGCA CTTTGGGAGG CCGTGGCGGG CAGATCACAT GAGATCATGA
10951  GTTCGAGACC AACCTGACCA ACATGGAGAG ACCCCATCTC TACTAAAAAT
11001  ACAAAATTAG CCGGGGTGGT GGCGCATGCC TGTAATCCCA GCTACTCGGG
11051  AGGCTGAGGC AGGAGAATCT CTTGAACCCG GGAGGCAGAG GTTGCGGTGA
11101  GCCAAGATCG TGCCTTTGCA CACCAGCCTA GGCAACAAGA GCGAAAGTCC
11151  GTCTCAAAAA AAAAGTAATT TTTTTAAGT TAACCTCTGT CAGCAAACAA
11201  ATTTAACCCA ATAAAGGTCT TTGTTTTTA ATGTAGTAGA GGAGTTAGGG
11251  TTTATAAAAA ATATGGTAGG GAAGGGGGTC CCTGGATTTG CTAATGTGAT
11301  TGTCATTTGC CCCTTAGGAG AGAGCTCTGT TAGCAGAATG AAAAAATTGG
11351  AAGCCAGATT CAGGGAGGGA CTGGAAGCAA AAGAATTTCT GTTCGAGGAA
11401  GAGCCTGATG TTTGCCAGGG TCTGTTTAAC TGGACATGAA GAGGAAGGCT
11451  CTGGACTTTC CTCCAGGAGT TTCAGGAGAA AGGTAGGGCA GTGGTTAAGA
11501  GCAGAGCTCT GCCTAGACTA GCTGGGGTGC CTAGACTAGC TGGGGTGCCC
11551  AGACTAGCTG GGGTGCCTAG ACTAGCTGGG TACTTGAGT GGCTCCTTCA
11601  GCCTGGACCT CGGTTTCCTC ACCTGTATAG TAGAGATATG GGAGCACCCA
11651  GCGCAGGATC ACTGTGAACA TAAATCAGTT AATGGAGGAA GCAGGTAGAG
11701  TGGTGCTGGG TGCATACCAA GCACTCCGTC AGTGTTTCCT GTTATTCGAT
11751  GATTAGGAGG CAGCTTAAAC TAGAGGGAGT TGAGCTGAAT CAGGATGTTT
11801  GTCCCAGGTA GCTGGGAATC TGCCTAGCCC AGTGCCCAGT TTATTTAGGT
```

FIG. 10F

```
11851    GCTCTCTCAG TGTTCCCTGA TTGTTTTTTC CTTTGTCATC TTATCTACAG
11901    GATGTGACTG GGAAGCTCTG GTTTCAGTGT CATGTGTCTA TTCTTTATTT
11951    CCAGGCAAAG GAAACCAACA ATAAGAAGAA AGAATTTGAG GAAACTGCGA
12001    AGAAAGTGCG CCGTGCCATC GAGCAGCTGG CTGCCATGGA TTGAGGCCTC
12051    TGGCCGGAGC TGCCTGGTCC CAGAGTGGCT GCACCACTTC CAGGGTTTAT
12101    TCCCTGGTGC CACCAGCCTT CCTGTGGGCC CCTTAGCAAT GTCTTAGGAA
12151    AGGAGATCAA CATTTTCAAA TTAGATGTTT CAACTGTGCT CCTGTTTTGT
12201    CTTGAAAGTG GCACCAGAGG TGCTTCTGCC TGTGCAGCGG GTGCTGCTGG
12251    TAACAGTGGC TGCTTCTCTC TCTCTCTCTC TTTTTGGGG GCTCATTTTT
12301    GCTGTTTTGA TTCCCGGGCT TACCAGGTGA GAAGTGAGGG AGGAAGAAGG
12351    CAGTGTCCCT TTTGCTAGAG CTGACAGCTT TGTTCGCGTG GGCAGAGCCT
12401    TCCACAGTGA ATGTGTCTGG ACCTCATGTT GTTGAGGCTG TCACAGTCCT
12451    GAGTGTGGAC TTGGCAGGTG CCTGTTGAAT CTGAGCTGCA GGTTCCTTAT
12501    CTGTCACACC TGTGCCTCCT CAGAGGACAG TTTTTTTGTT GTTGTGTTTT
12551    TTTGTTTTTT TTTTTTGGTA GATGCATGAC TTGTGTGTGA TGAGAGAATG
12601    GAGACAGAGT CCCTGGCTCC TCTACTGTTT AACAACATGG CTTTCTTATT
12651    TTGTTTGAAT TGTTAATTCA CAGAATAGCA CAAACTACAA TTAAAACTAA
12701    GCACAAAGCC ATTCTAAGTC ATTGGGAAA CGGGGTGAAC TTCAGGTGGA
12751    TGAGGAGACA GAATAGAGTG ATAGGAAGCG TCTGGCAGAT ACTCCTTTTG
12801    CCACTGCTGT GTGATTAGAC AGGCCCAGTG AGCCGCGGGG CACATGCTGG
12851    CCGCTCCTCC CTCAGAAAAA GGCAGTGGCC TAAATCCTTT TTAAATGACT
12901    TGGCTCGATG CTGTGGGGGA CTGGCTGGGC TGCTGCAGGC CGTGTGTCTG
12951    TCAGCCCAAC CTTCACATCT GTCACGTTCT CCACACGGGG GAGAGACGCA
13001    GTCCGCCCAG GTCCCGCTT TCTTTGGAGG CAGCAGCTCC CGCAGGGCTG
13051    AAGTCTGGCG TAAGATGATG GATTTGATTC GCCCTCCTCC CTGTCATAGA
13101    GCTGCAGGGT GGATTGTTAC AGCTTCGCTG GAAACCTCTG GAGGTCATCT
13151    CGGCTGTTCC TGAGAAATAA AAAGCCTGTC ATTTCAAACA CTGCTGTGGA
13201    CCCTACTGGG TTTTTAAAAT ATTGTCAGTT TTTCATCGTC GTCCCTAGCC
13251    TGCCAACAGC CATCTGCCCA GACAGCCGCA GTGAGGATGA GCGTCCTGGC
13301    AGAGACGCAG TTGTCTCTGG GCGCTTGCCA GAGCCACGAA CCCCAGACCT
13351    GTTTGTATCA TCCGGGCTCC TTCCGGGCAG AAACAACTGA AAATGCACTT
13401    CAGACCCACT TATTTATGCC ACATCTGAGT CGGCCTGAGA TAGACTTTTC
13451    CCTCTAAACT GGGAGAATAT CACAGTGGTT TTGTTAGCA GAAAATGCAC
13501    TCCAGCCTCT GTACTCATCT AAGCTGCTTA TTTTTGATAT TTGTGTCAGT
13551    CTGTAAATGG ATACTTCACT TTAATAACTG TTGCTTAGTA ATTGGCTTTG
13601    TAGAGAAGCT GGAAAAAAAT GGTTTTGTCT TCAACTCCTT TGCATGCCAG
13651    GCGGTGATGT GGATCTCGGC TTCTGTGAGC CTGTGCTGTG GGCAGGGCTG
13701    AGCTGGAGCC GCCCCTCTCA GCCCGCCTGC CACGGCCTTT CCTTAAAGGC
13751    CATCCTTAAA ACCAGACCCT CATGGCTGCC AGCACCTGAA AGCTTCCTCG
13801    ACATCTGTTA ATAAAGCCGT AGGCCCTTGT CTAAGCGCAA CCGCCTAGAC
13851    TTTCTTTCAG ATACATGTCC ACATGTCCAT TTTTCAGGTT CTCTAAGTTG
13901    GAGTGGAGTC TGGGAAGGGT TGTGAATGAG GCTTCTGGGC TATGGGTGAG
13951    GTTCCAATGG CAGGTTAGAG CCCCTCGGGC CAACTGCCAT CCTGGAAAGT
14001    AGAGACAGCA GTGCCCGCTG CCCAGAAGAG ACCAGCAAGC CAAACTGGAG
14051    CCCCCATTGC AGGCTGTCGC CATGTGGAAA GAGTAACTCA CAATTGCCAA
14101    TAAAGTCTCA TGTGGTTTTA TCTACTTTTT TTTTCTTTTT CTTTTTTTT
14151    GAGACAAGGC CTTGCCCTCC CAGGCTGGAG TGCAGTGGAA TGACCACAGC
14201    TCACCGCAAC CTCAAATTCT TGCGTTCAAG TGAACCTCCC ACTTTAGCCT
```

FIG. 10G

```
14251   CCCAAGTAGC TGGGACTACA GGCGCACGCC ATCACACCCG GCTAATTGAA
14301   AAATTTTTTT TTTTGTTTAG ATGGAATCTC ACTTTGTTGC CCAGGCTGGT
14351   CTCAAACTCC TGGGCTCAAG TGATCATCCT GCTTCAGCGT CCGACTTGTT
14401   GGTATTATAG GCGTGAGCCA CTGGGCCTGA CCTAGCTACC ATTTTTTAAT
14451   GCAGAAATGA AGACTTGTAG AAATGAAATA ACTTGTCCAG GATAGTCGAA
14501   TAAGTAACTT TTAGAGCTGG GATTTGAACC CAGGCAATCT GGCTCCAGAG
14551   CTGGGCCCTC ACTGCTGAAG GACACTGTCA GCTTGGGAGG GTGGCTATGG
14601   TCGGCTGTCT GATTCTAGGG AGTGAGGGCT GTCTTTAAAG CACCCCATTC
14651   CATTTTCAGA CAGCTTTGTC AGAAAGGCTG TCATATGGAG CTGACACCTG
14701   CCTCCCCAAG GCTTCCATAG ATCCTCTCTG TACATTGTAA CCTTTTATTT
14751   TGAAATGAAA ATTCACAGGA AGTTGTAAGG CTAGTACAGG GGATCC
```

SURVIVIN, A PROTEIN THAT INHIBITS CELLULAR APOPTOSIS AND ITS MODULATION

STATEMENT OF RELATED APPLICATIONS

This is a divisional of application U.S. application Ser. No. 08/975,080, filed on Nov. 20, 1997, now U.S. Pat. No. 6,245,523, which claims the benefit of U.S. Provisional Application No. 60/031,435, filed Nov. 20, 1996, both of which are herein incorporated by reference in their entirety.

FIELD OF THE INVENTION

The present invention relates to the field of modulating cell apoptosis, particularly agents useful to inhibit apoptosis, as well as to diagnostic and prognostic assays involving conditions in mediated by the expression of inhibitors of apoptosis. The invention specifically relates to the identification of a novel human gene, tentatively named Survivin. Survivin encodes a protein, Survivin, that inhibits cellular apoptosis, particularly in cancer cells and embryonic cells.

BACKGROUND OF THE INVENTION

Regulation of cell proliferation by programmed cell death (apoptosis) maintains tissue homeostasis during development and differentiation (Raff, M. D., Nature (1992) 356:397–400; Vaux, D. L. et al., Cell (1994) 76:777–779). This process involves an evolutionarily conserved multistep cascade (Oltvai, Z. et al., Cell (1994) 79:189–192), and is controlled by proteins that promote or counteract apoptotic cell death. Apoptosis also involves cell surface receptors (Smith, A. et al., Cell (1994) 76, 959–962), and associated signal transducers (Tartaglia, L. A. et al., Immunol Today (1992) 13:151–153), protease gene families (Martin, S. L. et al., Cell (1995) 82:349–352), intracellular second messengers (Kroemer, G. et al., FASEB J (1995) 9:1277–1287), tumor suppressor genes (Haffner, R. et al., Curr Op Gen Dev (1995) 5:84–90), and negative regulatory proteins that counteract apoptotic cell death (Hockenbery, D. et al., Nature (1990) 348:334–336). Aberrantly increased apoptosis or abnormally prolonged cell survival (Oltvai, Z. N. et al., Cell (1994) 79:189–192) may both contribute to the pathogenesis of human diseases, including autoimmune disorders, neurodegenerative processes, and cancer (Steller, H., Science (1995) 267:1445–1449; Thompson, C. B., Science (1995) 267:1456–1462).

Specifically, for example, inhibitors of apoptosis, most notably of the bcl-2 family (Reed, J, J Cell Biol (1994) 124:1–6, and Yang, E, et al., Blood (1996) 88:386–401), maintain lymphoid homeostasis and morphogenesis in adult (Hockenbery, D et al., Proc Natl Acad Sci USA (1991) 88:6961–6965) and fetal (LeBrun, D. et al. (1993) 142:743–753) tissues. Deregulated expression of bcl-2 has also been implicated in cancer, by aberrantly prolonging cell survival and facilitating the insurgence of transforming mutations.

In addition to bcl-2, several members of a new gene family of inhibitors of apoptosis related to the baculovirus IAP gene (Birnbaum, M. J. et al., J Virology (1994) 68:2521–2528; Clem, R. J. et al., Mol Cell Biol (1994) 14:5212–5222) have been identified in Drosophila and mammalian cells (Duckett, C. S. et al., EMBO J (1996) 15:2685–2694; Hay, B. A. et al., Cell (1995) 83:1253–1262; Liston, P. et al., Nature (1996) 379:349–353; Rothe, M. et al., Cell (1995) 83:1243–1252; Roy, N. et al., Cell (1995) 80:167–178). These molecules are highly conserved evolutionarily; they share a similar architecture organized in two or three approximately 70 amino acid amino terminus Cys/His baculovirus IAP repeats (BIR) and by a carboxy terminus zinc-binding domain, designated RING finger (Duckett, C. S. et al., EMBO J (1996) 15:2685–2694; Hay, B. A. et al., Cell (1995) 83:1253–1262; Liston, P. et al., Nature (1996) 379:349–353; Rothe, M. et al., Cell (1995) 83:1243–1252; Roy, N. et al., Cell (1995) 80:167–178). Recombinant expression of IAP proteins blocks apoptosis induced by various stimuli in vitro (Duckett, C. S. et al., EMBO J (1996) 15:2685–2694; Liston, P. et al., Nature (1996) 379:349–353), and promotes abnormally prolonged cell survival in the developmentally-regulated model of the Drosophila eye, in vivo (Hay, B. A. et al., Cell (1995) 83:1253–1262). Finally, deletions in a IAP neuronal inhibitor of apoptosis, NAIP, were reported in 75% of patients with spinal muscular atrophy, thus suggesting a potential role of this gene family in human diseases (Roy, N. et al., Cell (1995) 80:167–178).

Therapeutic and diagnostic uses of nucleic acids that encode various inhibitors of apoptosis relating to a member of the IAP family have been described in the patent literature. See, for example, International Patent Applications No. WO 97/06255, WO 97/26331, and WO 97/32601. In particular, the uses of such genes and gene products are contemplated for the novel protein and its encoding nucleic acid discussed below.

Recently, a novel gene encoding a structurally unique IAP apoptosis inhibitor, designated Survivin has been identified. Survivin is a −16.5 kD cytoplasmic protein containing a single BIR, and a highly charged carboxyl-terminus coiled-coil region instead of a RING finger, which inhibits apoptosis induced by growth factor (IL-3) withdrawal when transferred in B cell precursors (Ambrosini, G. et al., Nature Med. (1997) 3:917–921). At variance with bcl-2 or other IAP proteins, Survivin is undetectable in adult tissues, but becomes prominently expressed in all the most common human cancers of lung, colon, breast, pancreas, and prostate, and in −50% of high-grade non-Hodgkin's lymphomas, in vivo. Intriguingly, the coding strand of the Survivin gene was highly homologous to the sequence of Effector cell Protease Receptor-1 (EPR-1) (Altieri, D. C., FASEB J (1995) 9:860–865), but oriented in the opposite direction, thus suggesting the existence of two separate genes duplicated in a head-to-head configuration.

The present invention is based on the identification of a novel human gene which is nearly identical to EPR-1, but oriented in the opposite direction. The antisense EPR-1 gene product, designated Survivin, is a distantly related member of the IAP family of inhibitors of apoptosis (Duckett, C. S. et al., EMBO J (1996) 15:2685–2694; Hay, B. A. et al., Cell (1995) 83:1253–1262; Liston, P. et al., Nature (1996) 379:349–353; Rothe, M. et al., Cell (1995) 83:1243–1252; Roy, N. et al., Cell (1995) 80:167–178), and is prominently expressed in actively proliferating transformed cells and in common human cancers, in vivo, but not in adjacent normal cells. Functionally, inhibition of Survivin expression by up-regulating its natural antisense EPR-1 transcript resulted in massive apoptosis and decreased cell growth.

SUMMARY OF THE INVENTION

The present invention is based, in part, on the isolation and identification of a protein that is expressed in most cancer cells and inhibits cellular apoptosis, hereinafter Survivin or the Survivin protein. Based on this observation, the present invention provides purified Survivin protein.

The present invention further provides nucleic acid molecules that encode the Survivin protein. Such nucleic acid molecules can be in an isolated form, or can be operably linked to expression control elements or vector sequences.

The present invention further provides methods of identifying other members of the Survivin family of proteins. Specifically, the nucleic acid sequence of Survivin can be used as a probe, or to generate PCR primers, in methods to identify nucleic acid molecules that encode other members of the Survivin family of proteins.

The present invention further provides antibodies that bind to Survivin. Such antibodies can be either polyclonal or monoclonal. Anti-Survivin antibodies can be used in a variety of diagnostic formats and for a variety of therapeutic methods.

The present invention further provides methods for isolating Survivin binding partners. Survivin binding partners are isolated using the Survivin protein as a capture probe. Alternatively, Survivin can be used as bait in the yeast two-hybrid system to screen an expression library and identify genes that encode proteins that bind to the Survivin protein. Binding partners isolated by these methods are useful in preparing antibodies and also serve as targets for drug development.

The present invention further provides methods to identify agents that can block or modulate the association of Survivin with a binding partner. Specifically, an agent can be tested for the ability to block, reduce or otherwise modulate the association of Survivin with a binding partner by contacting Survivin, or a fragment thereof, and a binding partner with a test agent and determining whether the test agent blocks or reduces the binding of the Survivin protein to the binding partner.

The present invention further provides methods for reducing or blocking the association of Survivin with one or more of its binding partners. Specifically, the association of Survivin with a binding partner can be blocked or reduced by contacting Survivin, or the binding partner, with an agent that blocks the binding of Survivin to the binding partner. The method can utilize an agent that binds to Survivin or to the binding partner.

The present invention further provides methods of regulating the expression of Survivin within a cell. Expression of Survivin within a cell can be regulated so as to produce or inhibit the production of Survivin.

Blocking Survivin/binding partner associations or Survivin expression can be used to modulate biological and pathological processes that require Survivin. For example, methods that reduce Survivin production induce apoptosis of tumor cells. Stimulation of Survivin production can be used as a means of extending the culturability of cells or tissues.

The biological and pathological processes that require Survivin or Survivin/binding partner interactions can further be modulated using gene therapy methods. Additional genetic manipulation within an organism can be used to alter the expression of a Survivin gene or the production of a Survivin protein in an animal model. For example, a Survivin gene can be altered to correct a genetic deficiency; peptide modulators of Survivin activity can be produced within a target cell using genetic tansformation methods to introduce a modulator encoding nucleic acid molecules into a target cell; etc. The use of nucleic acids for antisense and triple helix therapies and interventions are expressly contemplated.

The present invention further provides methods of reducing the severity of pathological processes that require Survivin. Since expression of Survivin or association of Survivin with a binding partner is required for Survivin-mediated biological processes, agents that block Survivin expression, Survivin activity or the association of Survivin with a binding partner, can be used in therapeutic methods.

Figure 2A:
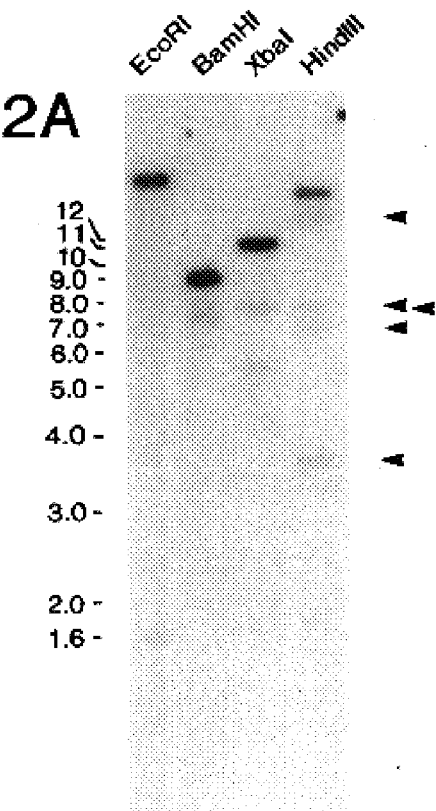
FIGS. 2A–C show the complexity and evolutionary conservation of EPR-1-related sequences. A. Southern blot of human genomic DNA. Samples were digested with the indicated restriction enzymes, transferred to GeneScreen nylon membranes and hybridized with the EPR-1 cDNA, in 5×SSC, 0.5% SDS, 5× Denhardt's and 0.1% sodium pyrophosphate at 65° C. Radioactive bands indicated by an arrow (7.6 kb BamHI, 7.5 kb XbaI and HindIII fragments of 15, 7.5, 6.4, and 3.7 kb) do not derive from the antisense EPR-1 gene in FIG. 1C. B. Southern blot of pulsed field gel electrophoresis. High molecular weight human genomic DNA was digested with the indicated restriction enzymes, separated by pulsed field gel electrophoresis for 20 h at 200 V with a pulse time of 75 sec, transferred to nylon membrane, and hybridized with the EPR-1 cDNA, as described in A. C. Multiple species Southern blot. EcoRI-digested genomic DNA from the indicated species was hybridized with a 3 548 bp fragment of the EPR-1 cDNA, as described in A. For all panels, molecular weight markers in kb are shown on the left.

B. Sequence alignment of the BIR in Survivin (SEQ ID NOS: 8 and 21) and in other IAP proteins by the Clustal method. IAP proteins are identified by accession number, L49433 (SEQ ID NOS: 9 and 22), TNFR2-TRAF signaling complex-associated IAP; L49441 (SEQ ID NOS: 10 and 23), apoptosis 2 inhibitor (*Drosophila*); P41436 (SEQ ID NOS: 11 and 24), IAP gene from *Cydia pomonella granulosis* virus; P41437 (SEQ ID NOS 12 and 25), IAP gene from *Orgya pseudotsugata* nuclear polyhedrosis virus; U19251 (SEQ ID NOS: 13 and 26), NAIP, neuronal inhibitor of apoptosis; U32373 (SEQ ID NOS 14 and 27), IAP-like protein ILP from *Drosofila melanogaster*; U32974 (SEQ ID NOS: 15 and 28), human IAP-like protein ILP; U36842 (SEQ ID NOS: 16 and 29), mouse inhibitor of apoptosis; U45878 (SEQ ID NOS: 17 and 30), human inhibitor of apoptosis 1; U45879 (SEQ ID NOS: 18 and 31), human inhibitor of apoptosis 2; U45880 (SEQ ID NOS: 19 and 32), X-linked inhibitor of apoptosis; U45881 (SEQ ID NOS: 20 and 33), *Drosofila* inhibitor of apoptosis. Conserved residues are boxed, identities between Survivin and NAIP (U19251); SEQ ID NOS: 13 and 26 are boxed and shaded. C. Immunoblotting with anti-Survivin antibody JC700. Protein-normalized aliquots of SDS-extracts of cell lines HEL (erythroleukemia), Daudi and JY (B lymphoma), THP-1 (monocytic), Jurkat and MOLT13 (T leukemia), or non transformed human lung Lu18 fibroblasts, HUVEC or PBMC were separated by electrophoresis on a 5–20% SDS gradient gel, transferred to Immobilon and immunoblotted with control non-immune rabbit IgG (RbIgG), or anti-Survivin antibody JC700 (Survivin). Protein bands were visualized by alkaline phosphatase-conjugated goat anti-rabbit IgG and tetrazolium salts. Molecular weight markers in kDa are shown on the left.

Figures 5A, 5B, 5C:
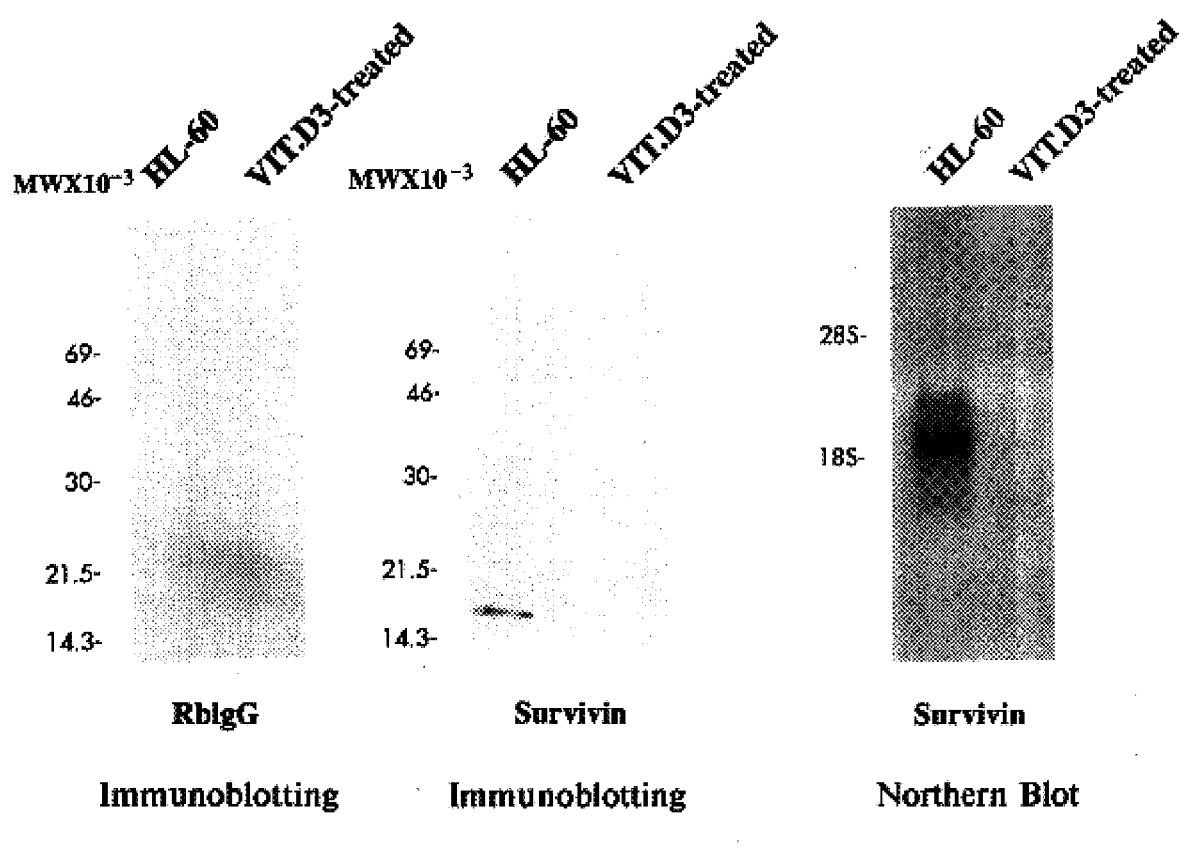

FIGS. 5A–C show the regulation of Survivin expression by cell growth/differentiation. HL-60 cells were terminally differentiated to a mature monocytic phenotype by a 72 h culture with 0.1 mM vitamin $D_3$ plus 17.8 mg/ml indomethacin. Survivin expression before or after vitamin $D_3$ differentiation was detected by immunoblotting with JC700 antibody, or by Northern hybridization with a Survivin-specific single strand probe. RbIgG, control non-immune rabbit IgG. Protein molecular weight markers in kDa and position of ribosomal bands are shown on the left of each blot.

FIGS. 6A–H show the over-expression of Survivin in human cancer, in vivo. A. Immunohistochemical staining of human lung adenocarcinoma with affinity-purified anti-Survivin antibody JC700 (20 $\mu$/ml). B. Inhibition of JC700 staining of lung adenocarcinoma by pre-absorption with the immunizing Survivin 3–19 peptide. C. Immunohistochemical expression of Survivin in squamous lung cell carcinoma, but not in the adjacent normal gland epithelium of the lung (C, arrow). D. In-situ hybridization of Survivin mRNA in squamous lung cell carcinoma with a Survivin-specific riboprobe. E. Expression of Survivin in pancreatic adenocarcinoma by immunohistochemistry with JC700. F. Normal pancreas, negative for Survivin expression by immunohistochemistry. G. In situ hybridization of Survivin mRNA expression in colon adenocarcinoma, but H, not in the adjacent non neoplastic colon gland epithelium (H, arrow). Magnifications are ×200, except G, ×400.

Figure 7A:
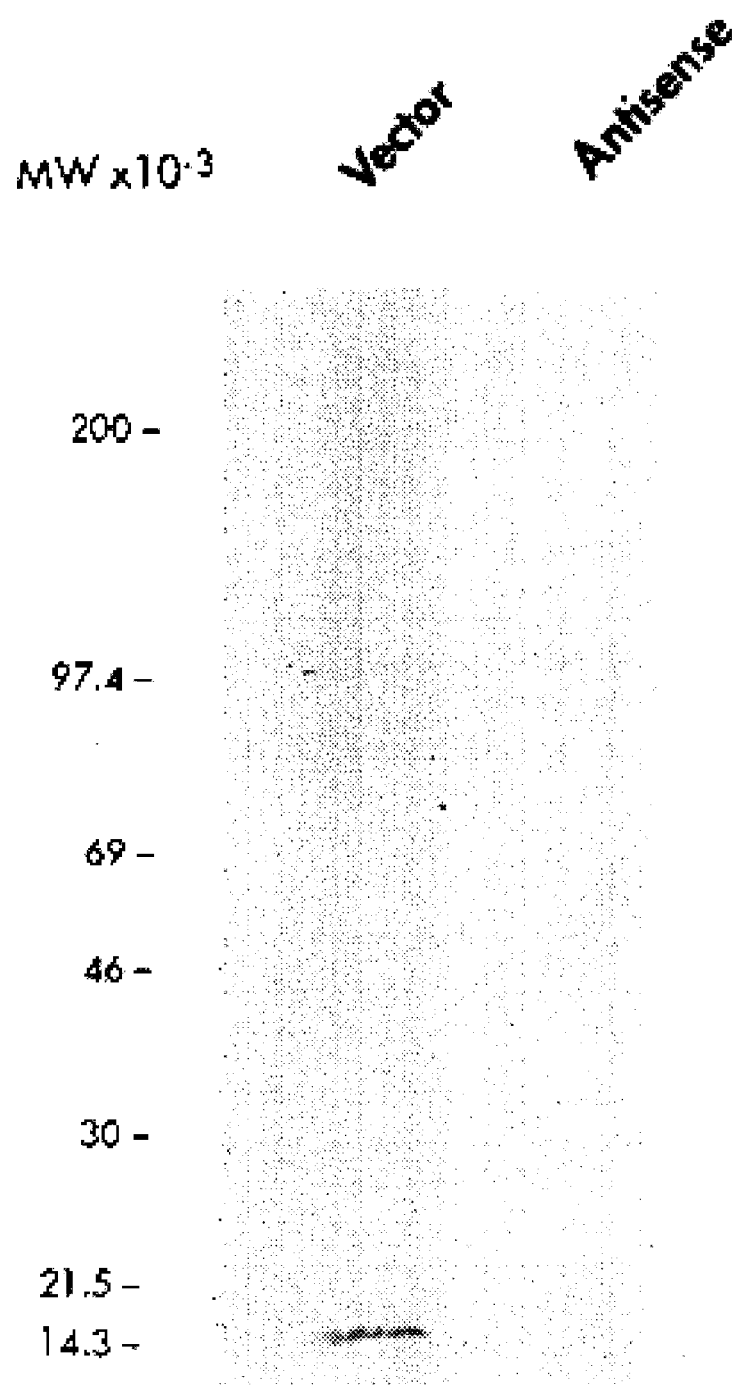
Figures 1, 7B:
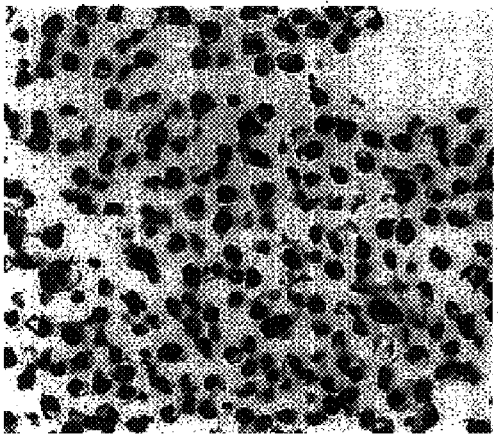
FIGS. 1A–D show the identification of a complementary EPR-1gene. A, B. Chromosomal location. A digoxigenin-labeled human P1 genomic clone selected by hybridization with the EPR-1 cDNA, was incubated with metaphase chromosomes isolated from phytohemagglutinin-stimulated PBMC in 50% formamide, 10% dextran sulfate and 2×SSC. The EPR-1-hybridizing gene was mapped in single-color labeling to the long arm of a group E chromosome (A), and in two-color staining with probe D17Z1, specific for the centromere of chromosome 17 (B), to the long arm of chromosome 17 (B), to band 17q25. C. Map of the antisense EPR-1 gene. A contig spanning 14796 bp was derived from two EPR-1-hybridizing P1 clones, subcloned in pBSKS⁻, and completely sequenced on both strands. Orientation of the map is 5'→3' with respect to the position of intron-exon boundaries (see below). Exons are solid boxes, a putative CpG island upstream exon 1 is an open box. The translational initiation codon (ATG) is indicated. Restriction sites are: B, BamHI, H, HindIII; P, PstI; S, SmaI; X, XbaI. D. Intron-exon boundaries of the antisense EPR-1 gene. Positions of the intron-exon boundaries in bp are indicated in parenthesis. The first nucleotide sequence corresponds to SEQ ID NO: 5. The second nucleotide sequence corresponds to SEQ ID NO: 6. The third nucleotide sequence corresponds to SEQ ID NO: 7.
Figures 2, 7B:
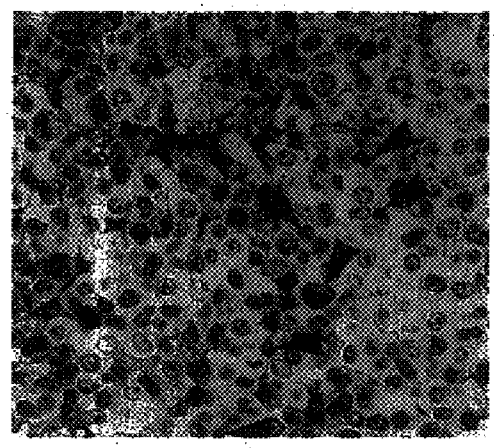
Figures 3, 7B:
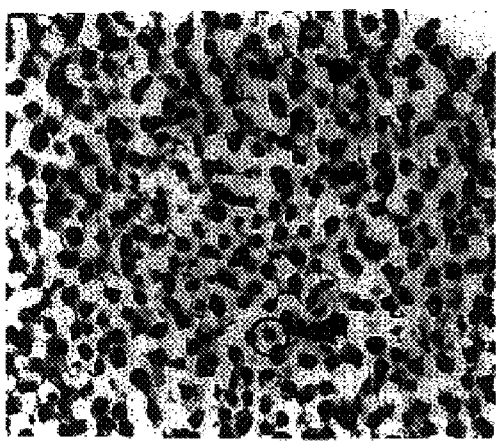
Figures 4, 7B:
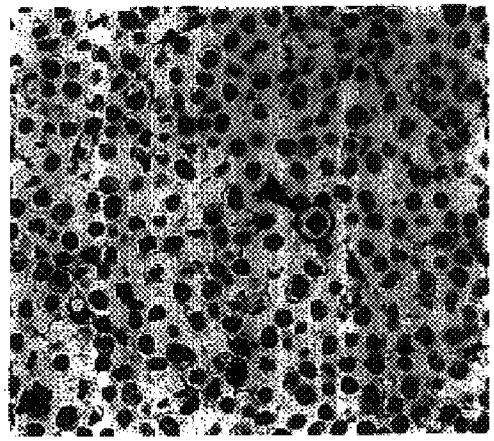
Figure 7C:
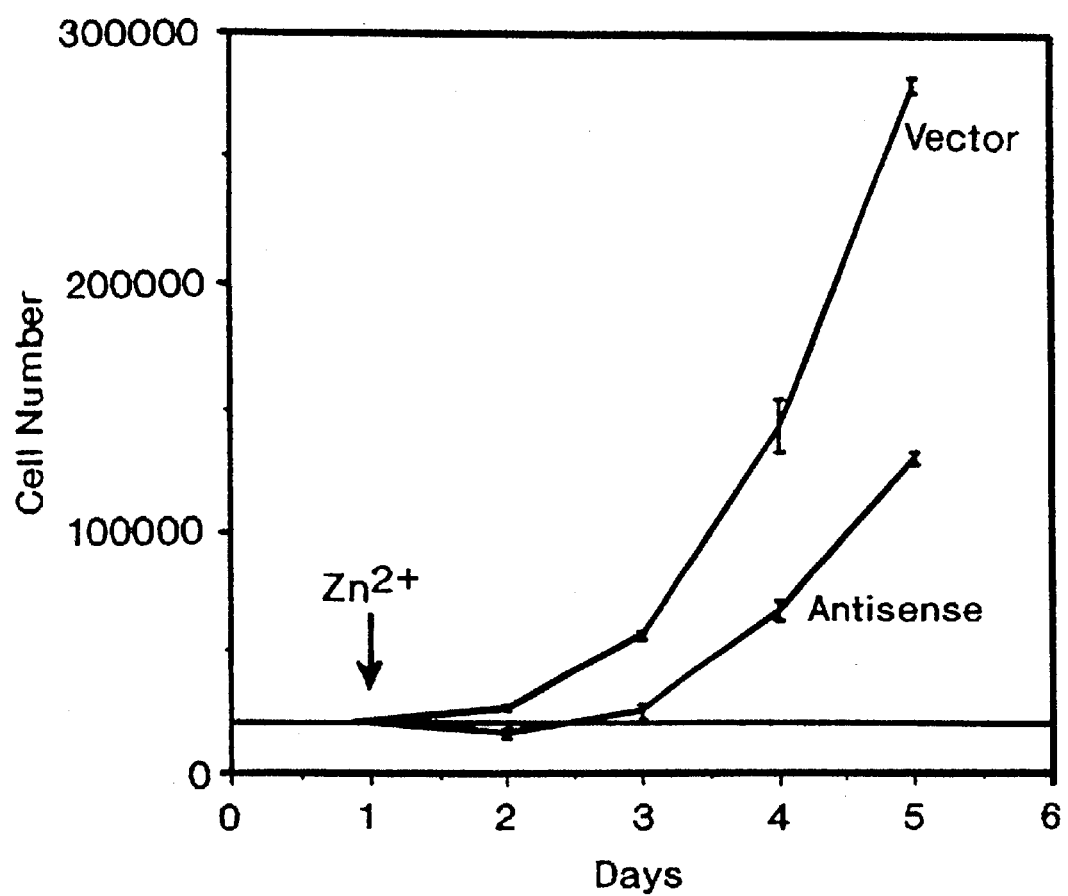

FIGS. 7A–C show the effect of Survivin on apoptosis/proliferation. A. EPR-1-regulation of Survivin expression. HeLa cells were transfected with control vector pML1 or the EPR-1 cDNA (which is antisense to Survivin) by electroporation, and selected in hygromicin (0.4 mg/ml). Aliquots of vector control HeLa cells (Vector) or Survivin antisense transfectants (Antisense) were induced with 200 mM $ZnSO_4$ detergent-solubilized, and immunoblotted with the anti-Survivin JC700 antibody. Molecular weight markers are shown on the left. B. Effect of Survivin on apoptosis. Survivin antisense transfectants (1, 2), or vector control HeLa cells (3, 4) were induced with $Zn^{2+}$ ions in 0% FBS for 24 h and stained by the AptoTag method with TdT-catalyzed dUTP labeling of 3-OH DNA ends and immunoperoxidase (1, 3), or by hematoxylineosin (HE) (2, 4). 1. Prominent nuclear DNA fragmentation detected by AptoTag staining in serum-starved Survivin antisense transfectants; 2. HE staining of antisense transfectants reveals the presence of numerous apoptotic bodies (arrows); 3. AptoTag staining of vector control HeLa cells detects a few sparse apoptotic cell (arrow); 4. HE staining of vector control HeLa cells. The arrow indicates a single apoptotic body. Magnification ×400. C. Effect of Survivin on cell growth. Twenty thousands vector control HeLa cells (Vector) or Survivin antisense transfectants (Antisense) were seeded in 24-well plates, induced with $ZnSO_4$, harvested at the indicated time points, and cell proliferation was determined microscopically by direct cell count. Data are the mean±SEM of replicates of a representative experiment out of seven independent determinations.

FIGS. 8A–D show the expression of Survivin in HL-60 cells. HL-60 cells were examined via Western and Northern blots for Survivin expression.

Figure 9:
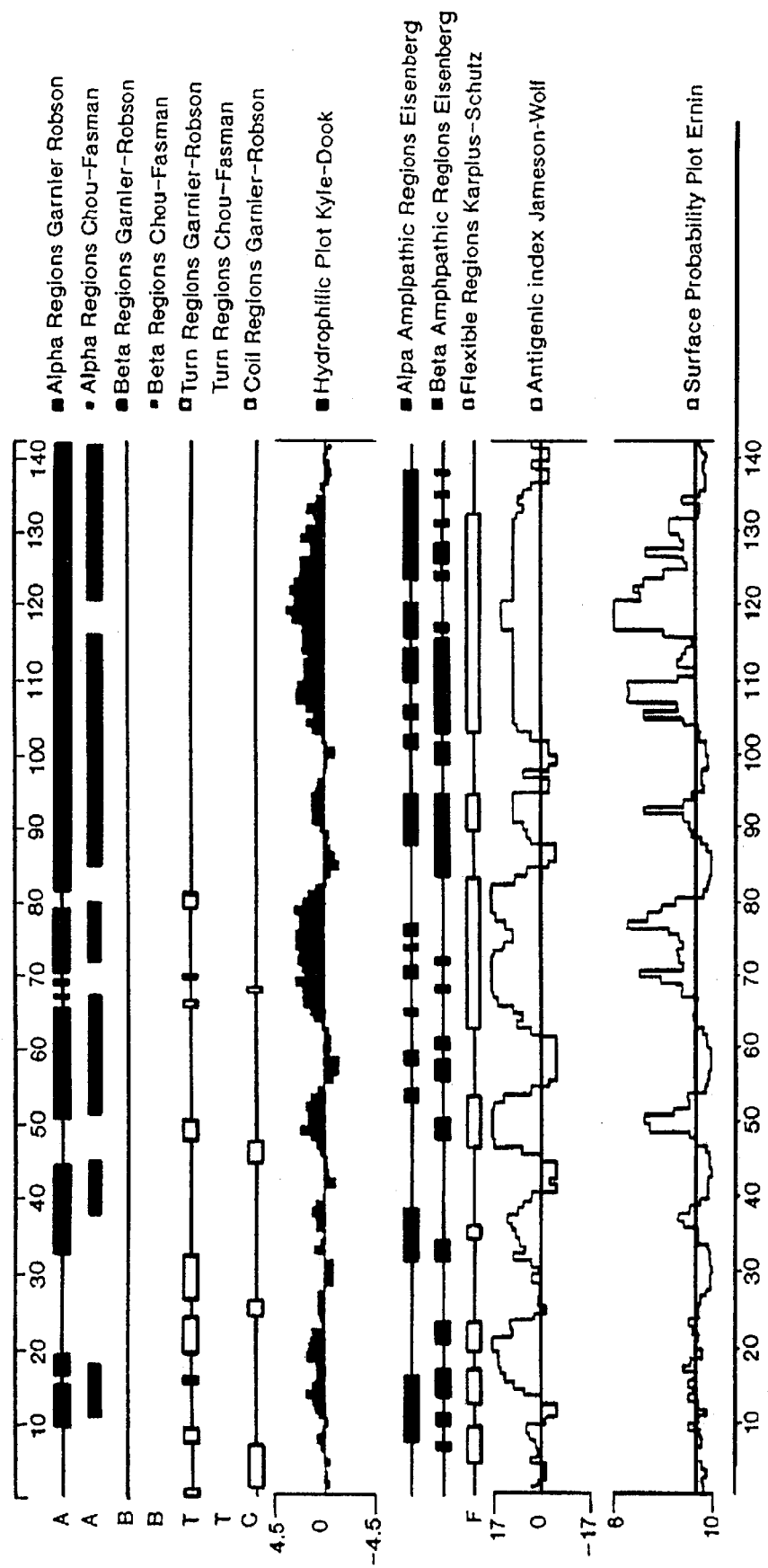

FIG. 9 presents a structural analysis of Survivin. The Survivin protein was analyzed using the Chou-Fasman. Garner-Robson, Kyle-Doolittle, Eisenberg, Karplus-Schultz, Jameson-Wolf and Emini analysis methods.

FIGS. 10A–G show the nucleotide Sequence of Survivin, which corresponds to SEQ ID NO: 35. The amino acid sequence displayed in FIG. 10 corresponds to SEQ ID NO: 34.

Figure 11A:
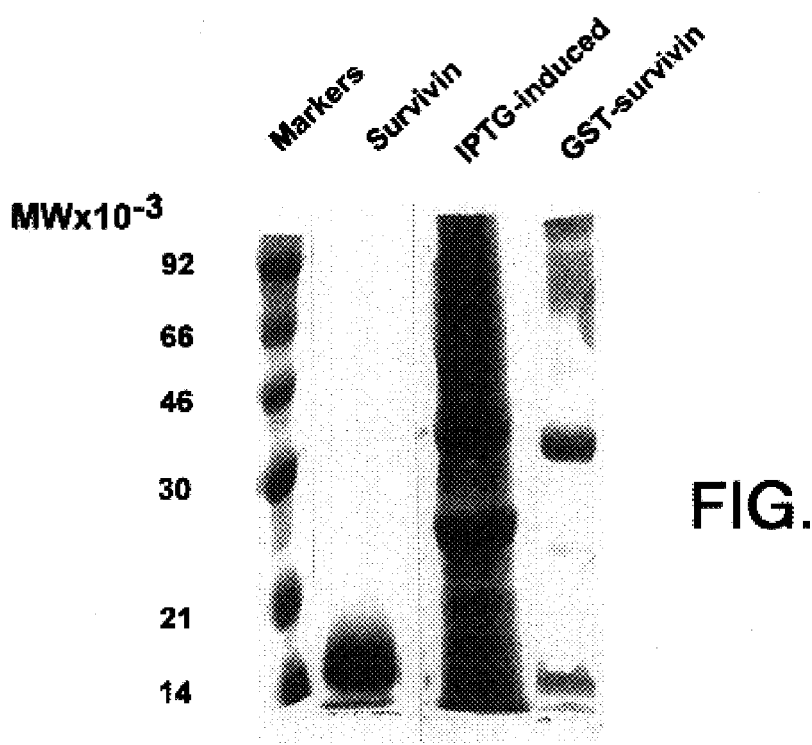
Figure 11B:
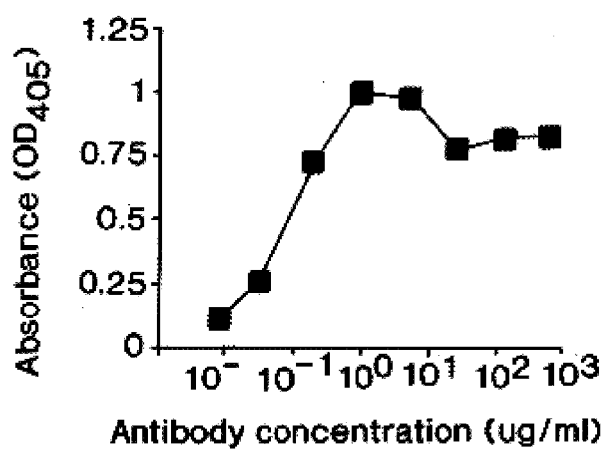
Figure 11C:
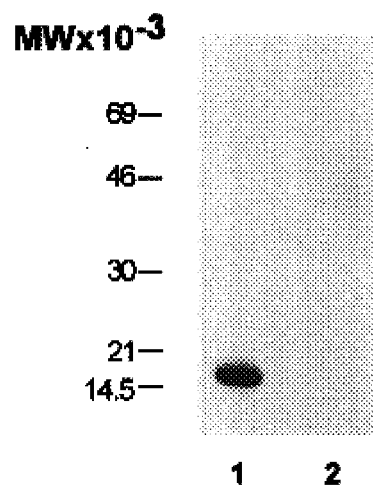

FIGS. 11A–C show the expression of Survivin and the generation and characterization of anti-Survivin mAb 8E2 by ELISA and immunoblotting.

Figure 12:
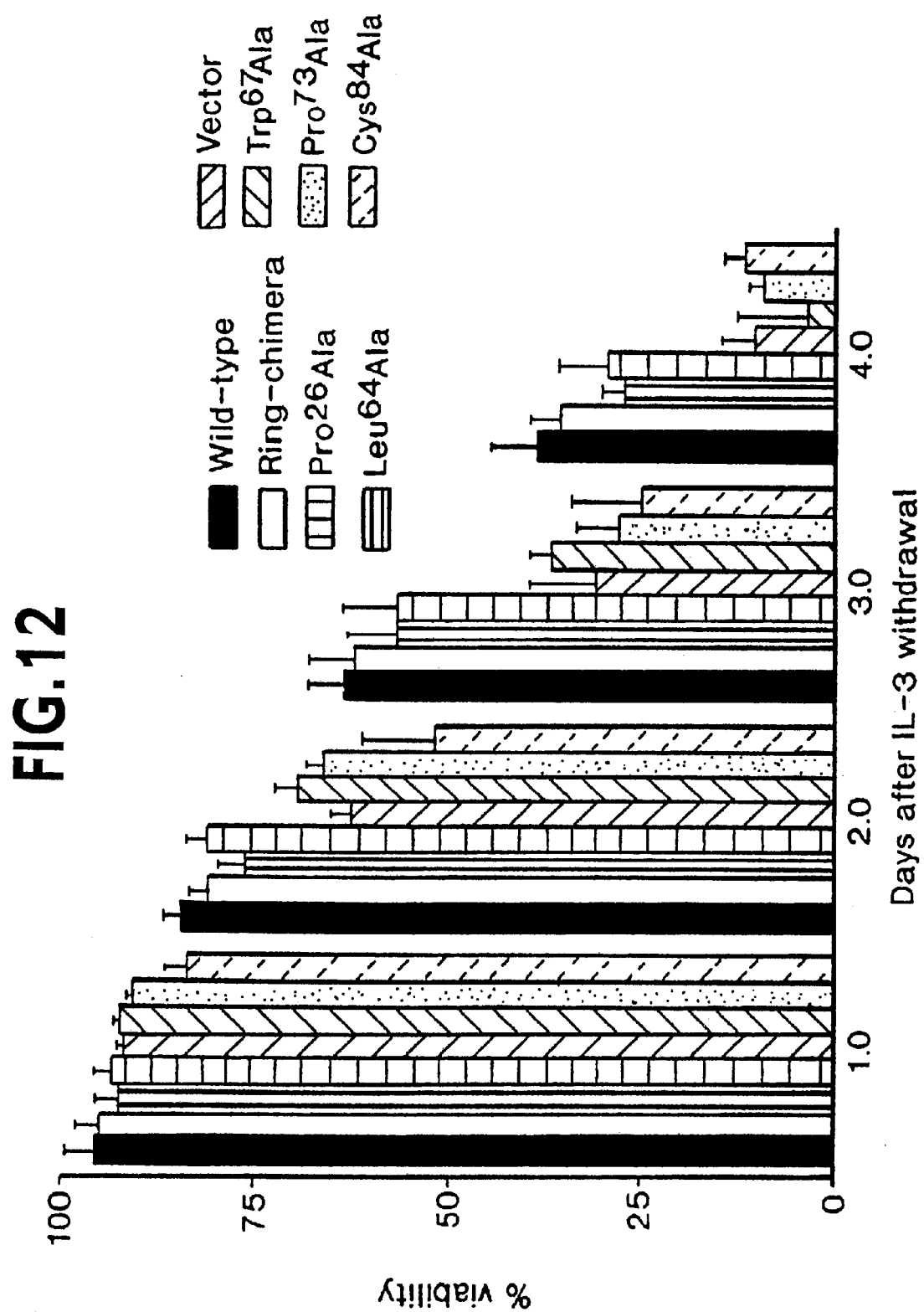

FIG. 12 shows the site-directed mutagenesis of Survivin and identification of key functional residues involved in apoptosis inhibition.

Figure 13:
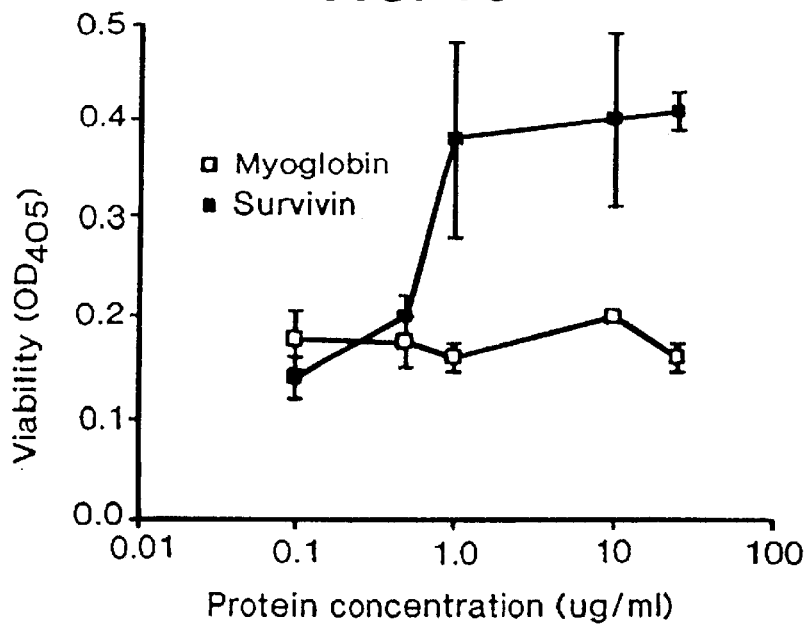

FIG. 13 shows the cytoprotective effect of Survivin addition on endothelial cell apoptosis.

Figure 14A:
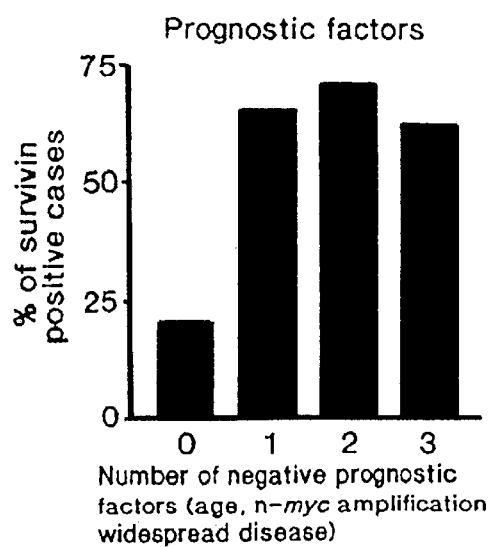
Figure 14B:
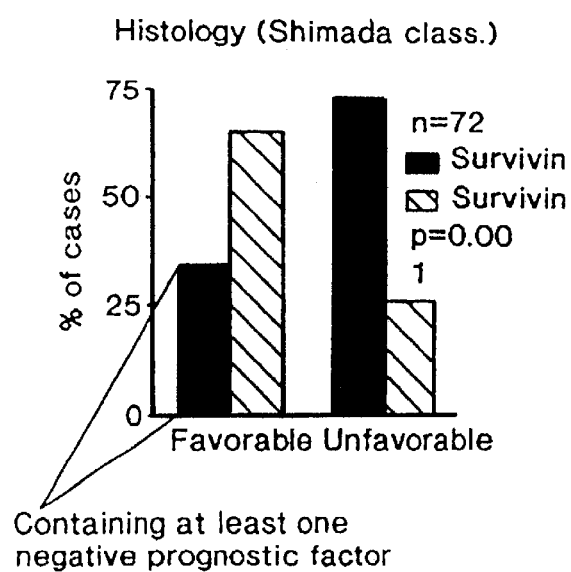

FIGS. 14A–B show that the presence of Survivin is a negative predictive-prognostic factor in neuroblastoma.

Figure 15A:
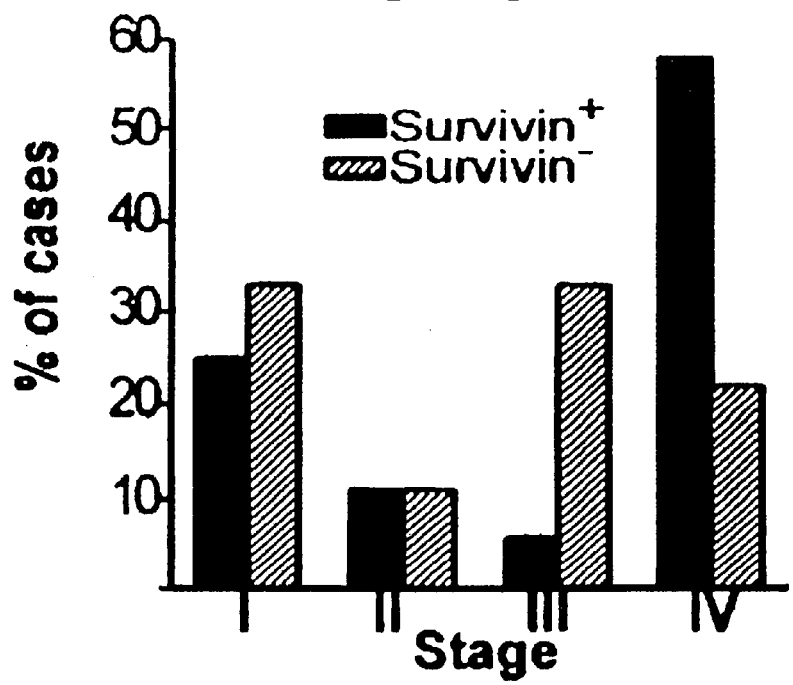
Figure 15B:
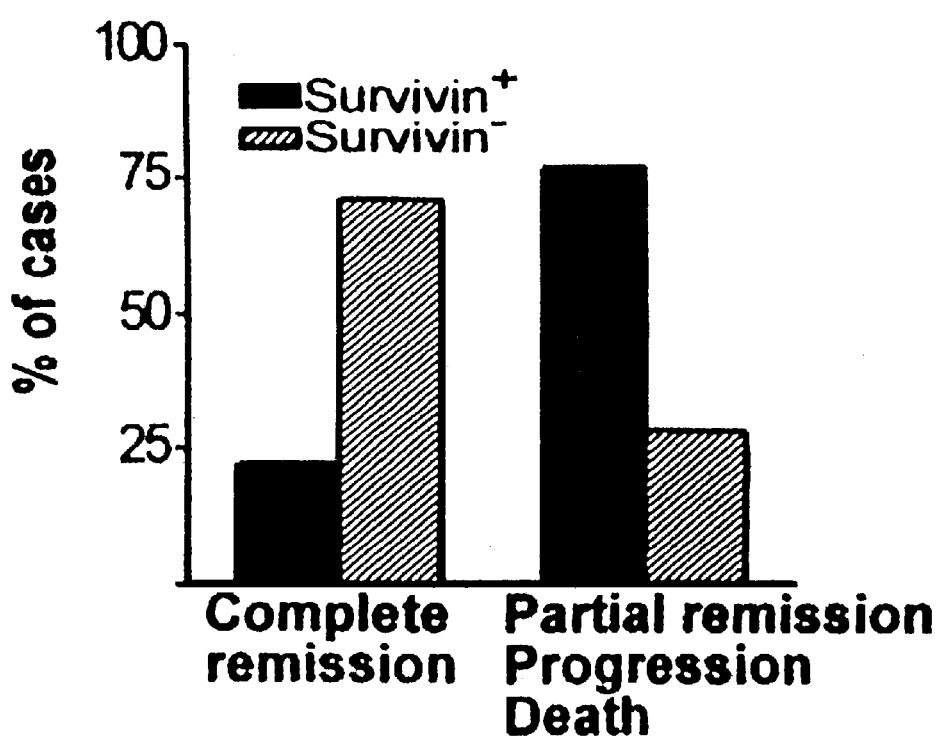

FIGS. 15A–B show that the presence of Survivin is a negative predictive prognostic factor in high-grade non-Hodgkin's lymphoma.

Figure 16:
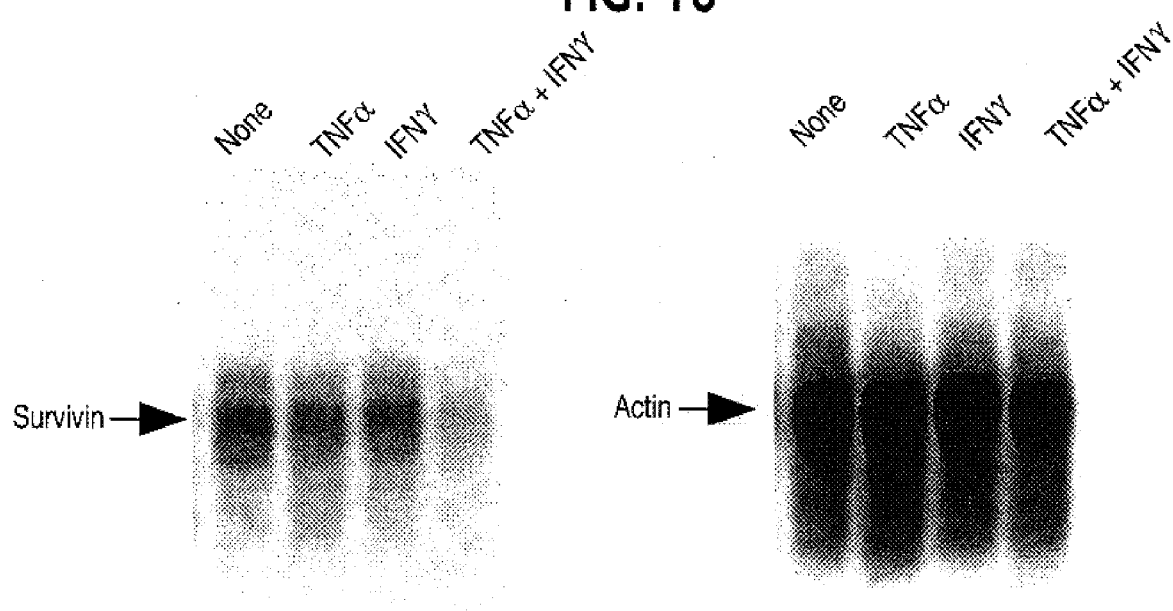

FIG. 16 shows the down regulation of Survivin induced by inflammatory and cytostatic cytokines.

Figure 17:
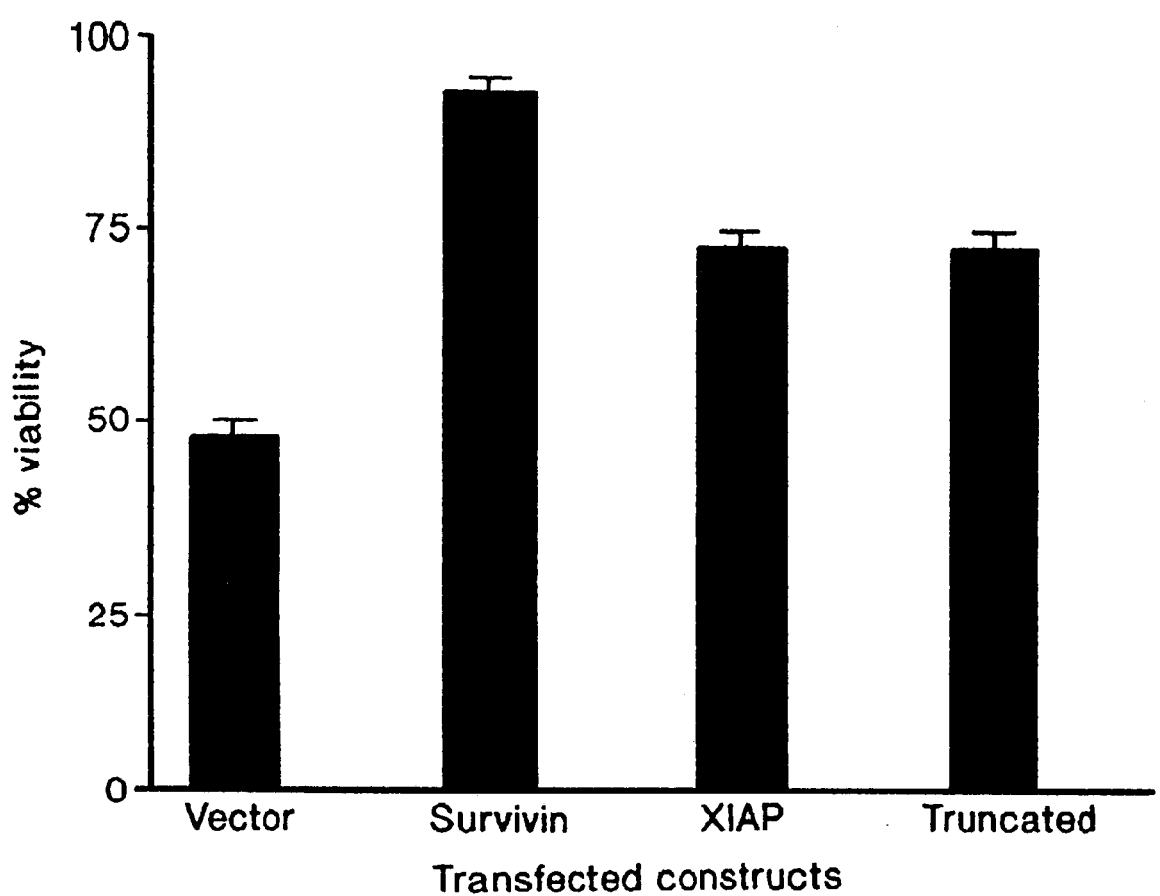

FIG. 17 shows the effects of Survivin constructs or XIAP on apoptosis induced in NIH3T3 cells by hydrogen peroxide.

DETAILED DESCRIPTION OF THE PREFERRED EMBODIMENT

I. General Description

The present invention is based in part on identifying a novel protein that is expressed in tumor cells and inhibits cellular apoptosis, hereinafter the Survivin protein or Survivin. Survivin is also found to be expressed in embryonic tissues.

The Survivin protein can be used as an agent, or serve as a target for agents, that can be used to inhibit or stimulate Survivin mediated inhibition of cellular apoptosis, for example to block abnormal cell growth or to extend cell growth in culture.

As used herein, modulation of apoptosis means increasing or decreasing the number of cells that would otherwise undergo apoptosis in a given cell population. This can be effected by increasing or decreasing the amount of Survivin present in a cell or by increasing or decreasing the activity of the Survivin. Preferably, the given cell population in which apoptosis is to be modulated is found in a tumor or other tissue or group of cells in which beneficial effect results from the modulation. Also, preferably, the increase or decrease in number of cells that would otherwise undergo apoptosis in a given cell population is at least about 10%, 20%, 40% or more preferably at least about 50% of the cells in that population.

The present invention is further based on the development of methods for isolating proteins that bind to Survivin Probes based on the Survivin protein or fragments of Survivin as discussed below are used as capture probes to isolate Survivin binding proteins. Dominant negative proteins, DNAs encoding these proteins, antibodies to these binding proteins, peptide fragments of these proteins or mimics of these proteins may be introduced into cells to affect Survivin function. Additionally, these proteins provide novel targets for screening of synthetic small molecules and combinatorial or naturally occurring compound libraries to discover novel therapeutics to regulate Survivin function.

II. Identification, General Characterization and Tissue Distribution of Survivin The present invention is based on the identification on chromosome 17q25 of a novel member of the IAP family of inhibitors of apoptosis, designated Survivin, which may confer a selective advantage for cancer cell growth. Relevant features of the Survivin gene include its developmentally- and differentiation-regulated expression, its nearly identical and complementary DNA sequence with the factor Xa receptor EPR-1 , and its abundant in vivo expression in common human malignancies, but not in the adjacent non-neoplastic population. As described below, targeting Survivin expression by metallothionein-induction of EPR-1 mRNA resulted in apoptosis and inhibition of proliferation of HeLa cell transfectants.

In addition to their contribution to hemostasis, cellular receptors for blood proteases have recently emerged as pleiotropic signaling molecules, playing a crucial role in embryologic development (Connolly, A. J. et al., *Nature* (1996) 381:516–519), and vasculogenesis (Carmeliet, P. et al., *Nature* (1996) 383:73–75). In this context, the Survivin gene was isolated by hybridization with the cDNA for EPR-1, a receptor for factor Xa contributing to procoagulant activity (Altieri, D. C., *FASEB J* (1995) 9:860–865), and T cell activation (Duchosal, M. A. et al., *Nature* (1996) 380:352–356). Although the Survivin coding sequence was found to be nearly identical to the EPR-1 cDNA, its orientation was unambiguously assigned to the antisense EPR-1 strand for the position of the consensus splice sites at intron-exon boundaries (Padgett, R. A. et al., *Ann Rev Biochem* (1986) 55:1119–1150). On the other hand, the authenticity of the EPR-1 "sense" strand was demonstrated in previous studies, when mammalian cells transfected with the EPR-1 cDNA or with chimeric EPR-1 constructs (Ambrosini, G. et al., *J Biol Chem* (1996) 271:1243–1248 and Altieri, D. C., *FASEB J* (1995) 9:860–865), were recognized by anti-EPR-1 mAbs and bound factor Xa in a specific and saturable reaction.

These findings could be reconciled by the existence of multiple, highly homologous, EPR-1 transcripts oriented in opposite directions. The heterogeneity of EPR-1 mRNA and the complex pattern of Southern hybridization support this hypothesis. Previously, double strand EPR-1 probes detected three strongly hybridizing bands of 1.9, 3.4 and ~1.5 kb in mRNA of EPR-1$^+$ cells (Altieri, D. C., *FASEB J* (1995) 9:860–865). Here, single strand-specific probes confirmed the presence of multiple mature and polyadenylated EPR-1-related messages, and revealed that the 1.9 and 3.4 kb bands corresponded to two highly regulated, antisense EPR-1 transcripts, while the 1.5 kb band, more accurately defined as 1.2 kb, coincided with a genuine EPR-1-encoding message. While the 1.9 kb antisense transcript clearly originated from the Survivin gene described here, a gene encoding the 1.2 kb "sense" EPR-1 message has not yet been identified.

However, (i) the presence of several genomic EPR-1-hybridizing bands unrelated to the Survivin gene, (ii) the different restriction pattern of EPR-1 sequences in various species, and (iii) the numerous expressed sequence tag database entries matching ($P=0.018-7\times10^{-11}$) the positive (accession n. W46267), or the negative (accession n. W34764, W83810, T29149) EPR-1 strand, altogether suggest the existence of at least a second, highly-related, EPR-1 gene oriented in the opposite direction to that described here, and encoding the previously characterized factor Xa receptor (Altieri, D. C., *FASEB J* (1995) 9:860–865).

A similar situation could arise from gene duplication event(s) involving EPR-1sequences. Interestingly, the single hybridization signal detected on chromosome 17q25, and the single hybridizing bands identified in a Southern blot of high molecular weight genomic DNA, suggest that EPR-1-related sequences potentially oriented in opposite directions may be adjacent in close proximity, within a physical interval of 75–130 kb.

The presence of multiple EPR-1 transcripts oriented in opposite directions implies a reciprocal regulatory mechanism by naturally occurring antisense. This is consistent with the predominantly discordant and mutually exclusive distribution of sense and antisense EPR-1 messages in developing or adult tissues in vivo, and during HL-60 cell terminal differentiation. While antisense regulation is common in prokaryotes (Green, P. J. et al., *Annu Rev Biochem* (1986) 55:569–597), a growing number of eukaryotic gene products have been recently characterized for the occurrence of functional antisense transcripts potentially participating in gene regulation, including basic fibroblast growth factor (Kimmelman, D. et al., *Cell* (1989) 59:687–696; Murphy, P. R. et al., *Molecular Endocrinology* (1994) 8:852–859), al(I) collagen (Farrell, C. M. et al., *J Biol Chem* (1995) 270:3400–3408 and Lukens, 1995), n-myc (Krystal, G. W. et al., *Mol Cell Biol* (1990) 10:4180–4191), c-myc (Celano, P. et al., *J Biol Chem* (1992) 267:15092–15096), p53 (Khochbin, S. et al., *EMBO J* (1989) 8:4107–4114), c-erbAa (Lazar, M. A. et al., *Mol Cell Biol* (1989) 9:1128–1136), and CD3 ζ/η/θ locus (Lerner, A. et al., *J Immunol* (1993) 151:3152–3162).

As described below, the existence of a EPR-1/Survivin gene balance regulated by functional antisense was demonstrated in HeLa cell transfectants, when metallothionein-induced transcription of the EPR-1 "sense" strand suppressed the expression of Survivin and profoundly influenced apoptosis/cell proliferation (see below). This regulatory mechanism was not due to a potential protein association between EPR-1 and Survivin, since the EPR-1 construct used for these experiments lacked a translational initiation codon. Additional experiments have evaluated the ability of a Survivin antisense to inhibit cell growth. This was done by transiently co-transfecting the Survivin antisense with a LacZ reported plasmid and making a determination of cell viability after a 48-h transfection in β-galactosidase expressing cells. The results indicated that the viability of Survivin antisense transfectants was <20% of control cells transfected with the empty vector. A control antisense of ICAM-1 (intercellular adhesion molecule-1) similarly co-transfected in HeLa cells was ineffective.

Survivin was found to be a small protein of 142 amino acids (~16.5 kDa) with no amino acid sequence homology to EPR-1, and designated Survivin for the presence of a BIR-homologous domain (Birnbaum, M. J. et al., *J Virology* (1994) 68:2521–2528; Clem, R. J. et al., *Mol Cell Biol* (1994) 14:5212–5222) found in IAP inhibitors of apoptosis (Duckett, C. S. et al., EMBO J (1996) 15:2685–2694; Hay, B. A. et al., Cell (1995) 83:1253–1262; Liston, P. et al., Nature (1996) 379:349–353; Rothe, M. et al., Cell (1995) 83:1243–1252; Roy, N. et al., Cell (1995) 80:167–178). Based on overall sequence conservation, the absence of a carboxy terminus RING finger and the presence of a single, partially conserved, BIR domain, Survivin is the most distantly related member of the IAP family, sharing the highest degree of similarity with NAIP (Roy, N. et al., Cell (1995) 80:167–178). Thus, unlike bcl-2 or other IAP proteins, Survivin is undetectable in adult tissues, but becomes prominently expressed in all the most common human cancers of lung, colon, breast, pancreas, and prostate, and in ~50% of high-grade non-Hodgkin's lymphomas, in vivo. Additionally, unlike other IAP proteins (Deveraux, Q. et al., Nature (1997) 388:300–304), Survivin does not bind caspases in a cell-free system (Roy, N. et al., Blood (1997) 595:2645.

Consistent with the anti-apoptosis properties of IAP proteins in vitro (Duckett, C. S. et at. *EMBO J* (1996) 15:2685–2694; Liston, P. et al., *Nature* (1996) 379:349–353), and in vivo (Hay, B. A. et al., *Cell* (1995) 83:1253–1262), inhibition of Survivin expression by the EPR-1 transcript (which naturally is antisense to Survivin) resulted in increased apoptosis, as determined by in situ internucleosomal DNA fragmentation in HeLa cell transfectants. The ability of a RING finger-less IAP protein to counteract apoptosis is not without a precedent, as demonstrated by the suppression of apoptosis mediated by NAIP (Liston, P. et al., *Nature* (1996) 379:349–353), and by the in vivo gain-of-function of a *Drosofila* IAP protein following deletion of the RING finger (Hay, B. A. et al., *Cell* (1995) 83:1253–1262). Although anti-apoptosis genes are thought to play an indirect role in cell growth, by favoring the accumulation of oncogenic mutations(s) in aberrantly long-living cells (Reed, J. C., *J Cell Biol* (1994) 124:1–6), down-regulation of Survivin resulted in a profound inhibition of HeLa cell proliferation. While this may derive from rapid disappearance of HeLa cells expressing the highest levels of antisense transcripts by apoptosis, a similar decrease in tumor cell proliferation has been reported in vivo after antisense inhibition of bcl-2 (Reed, J. C. et al., *Proc Natl Acad Sci USA* (1990) 87:3660–3664).

The possibility that IAP proteins may play a more general role in cell proliferation, not exclusively restricted to apoptosis inhibition, has been proposed earlier. Rothe et al., have recently demonstrated that the amino terminus BIR in two IAP proteins (cIAPs) physically interacts with the signal transducers associated with the 75 kDa TNF receptor (Rothe, M. et al., *Cell* (1995) 83:1243–1252), a molecule primarily implicated in cell proliferation and survival rather than apoptotic signaling (Tartaglia, L. A. et al. *Immunol Today* (1992) 13:151–153). While it is not known if Survivin is physically linked to signaling molecules (Rothe, M. et al., *Cell* (1995) 83:1243–1252), the structural divergence of its BIR as compared with other IAP proteins (Duckett, C. S. et al., *EMBO J* (1996) 15:2685–2694; Hay, B. A. et al., *Cell* (1995) 83:1253–1262; Liston, P. et al., *Nature* (1996) 379:349–353; Rothe, M. et al., *Cell* (1995) 83:1243–1252; Roy, N. et al., *Cell* (1995) 80:167–178), may confer specificity for supramolecular interaction(s) potentially relevant to its particular mechanism of apoptosis inhibition/cell growth.

Dysregulation of programmed cell death (apoptosis) has recently emerged as a primary mechanism contributing to the pathogenesis of various human diseases, including cancer (Steller, H., *Science* (1995) 267;1445–1449; Thompson, C. B., *Science* (1995)267:1456–1462). While the impact of anti-apoptosis gene(s) in neoplasia is highlighted by the role of bcl-2 in follicular lymphoma (Korsmeyer, S. J., *Blood* (1992) 80:879–886), a potential distribution of LAP proteins in cancer had not been previously investigated. In this context, one of the most striking characteristics of Survivin was its abundant expression in actively proliferating transformed cell lines, and in all the most common human malignancies of lung, colon, pancreas, and breast, in vivo, but not in the non-neoplastic adjacent cell population. This distribution in multiple human cancers may signal a fundamental role of this molecule in apoptosis/cell proliferation mechanisms in neoplasia. By analogy with the paradigm of bcl-2, over-expression of Survivin in cancer may lead to aberrantly prolonged cell viability (Veis, D. J. et al., *Cell* (1993) 75:229–240), increased resistance to chemotherapy-induced apoptosis (Miyashita, T. et al., *Blood* (1993) 81:151–157), and, as suggested by the in vitro studies reported above, in a direct advantage for transformed cell proliferation.

On the other hand, for its presence in normal PBMC and benign breast adenomas, in vivo (unpublished observations), Survivin expression cannot be interpreted per se as a marker of malignant transformation but may reflect a more general, developmental- or cell type-specific response to certain stimuli. This is consistent with the presence of Survivin during normal embryonic (our unpublished observations) and fetal development, and its rapid disappearance in growth-arrested cell types (i.e. vitamin $D_3$-treated HL-60), and terminally-differentiated tissues, in vivo. At variance with other IAP proteins which are constitutively found in adult mature tissues (Duckett, C. S. et al., *EMBO J* (1996) 15:2685–2694; Liston, P. et al., *Nature* (1996) 379:349–353; Rothe, M. et al., *Cell* (1995) 83:1243–1252), this pattern of expression is reminiscent of the distribution of bcl-2 in fetal tissues (LeBrun, D. P. et a., *Am J Pathol* (1993) 142:743–753), and its more restricted presence in differentiated cells, correlating with susceptibility to apoptosis (Hockenbery, D. M. et al., *Proc Natl Acad Sci USA* (1991) 88:6961–6965).

In summary, these findings identify Survivin as a novel link between IAP proteins and cancer, in vivo. A key implication of the data presented below is the possibility to balance the effect of this potent anti-apoptosis gene by manipulating a normal cell regulatory mechanism, centered on the expression of EPR-1 (Altieri, D. C., *FASEB J* (1995) 9:860–865). Targeting Survivin may then remove a selective advantage for transformed cell growth and be therapeutically beneficial to increase the susceptibility of cancer cells to chemotherapy-induced apoptosis. Along the same line, identification of polymorphic markers and construction of extended aplotypes within and around the EPR-1/Survivin locus may provide new insights on the population genetics of susceptibility to chemotherapy.

III. Specific Embodiments
A. Survivin Protein

The present invention provides isolated Survivin protein, as well as allelic variants of the Survivin protein, and conservative amino acid substitutions of the Survivin protein. As used herein, the Survivin protein (or Survivin) refers to a protein that has the amino acid sequence of human Survivin depicted in FIG. 4. The term "Survivin protein" also includes naturally occurring allelic variants of Survivin, naturally occurring proteins that have a slightly different amino acid sequence than that specifically recited above. Allelic variants, though possessing a slightly different amino acid sequence than those recited above, will still have the requisite ability to inhibit cellular apoptosis.

As used herein, the Survivin family of proteins refers to Survivin proteins that have been isolated from organisms in addition to humans. The methods used to identify and isolate other members of the Survivin family of proteins are described below.

Survivin is a member of the IAP (inhibitory apoptosis proteins) family of protein. However, Survivin is the first member of a unique subfamily of IAP proteins that differ from other IAP proteins in significant ways. Despite homology and sequence conservation in the BIR module between Survivin and other members of this gene family, there arc important structural differences that are unique to members of the Survivin family of proteins. First unlike any other IAP protein, Survivin has only one BIR module (most of the other molecules have 2–3). Further, Survivin does not contain a carboxy-terminal RING finger but has a predicted coiled-coil instead. Only the Neuronal Apoptosis Inhibitory Protein (NAIP) in the IAP family lacks a RING finger, but does not contain a carboxy-terminus coiled coil. Finally there is no DNA sequence similarity between Survivin and other IAP proteins (PCR primers designed on Survivin are unlikely to detect other IAP proteins and vice-versa).

The Survivin proteins of the present invention are preferably in isolated from. As used herein, a protein is said to be isolated when physical, mechanical or chemical methods are employed to remove the Survivin protein from cellular constituents that are normally associated with the Survivin protein. A skilled artisan can readily employ standard purification methods to obtain an isolated Survivin protein.

The Survivin proteins of the present invention further include conservative variants of the Survivin proteins herein described. As used herein, a conservative variant refers to alterations in the amino acid sequence that do not adversely affect the ability of the Survivin protein to bind to a Survivin binding partner and/or to inhibit cellular apoptosis. A substitution, insertion or deletion is said to adversely affect the Survivin protein when the altered sequence prevents the Survivin protein from associating with a Survivin binding partner and/or prevents the Survivin protein from inhibiting cellular apoptosis. For example, the overall charge, structure or hydrophobic/hydrophilic properties of Survivin can be altered without adversely affecting the activity of Survivin Accordingly, the amino acid sequence of Survivin can be altered, for example to render the peptide more hydrophobic or hydrophilic, without adversely affecting the activity of Survivin.

The allelic variants, the conservative substitution variants and the members of the Survivin family of proteins, will have the ability to inhibit cellular apoptosis. Such proteins will ordinarily have an amino acid sequence having at least about 75% amino acid sequence identity with the human Survivin sequence, more preferably at least about 80%, even more preferably at least about 90%, and most preferably at least about 95%. Identity or homology with respect to such sequences is defined herein as the percentage of amino acid residues in the candidate sequence that are identical with the known peptides, after aligning the sequences and introducing gaps, if necessary, to achieve the maximum percent homology, and including any conservative substitutions as being homologous. N-terminal, C-terminal or internal extensions, deletions, or insertions into the peptide sequence shall not be construed as affecting homology.

Figures 1, 4C:
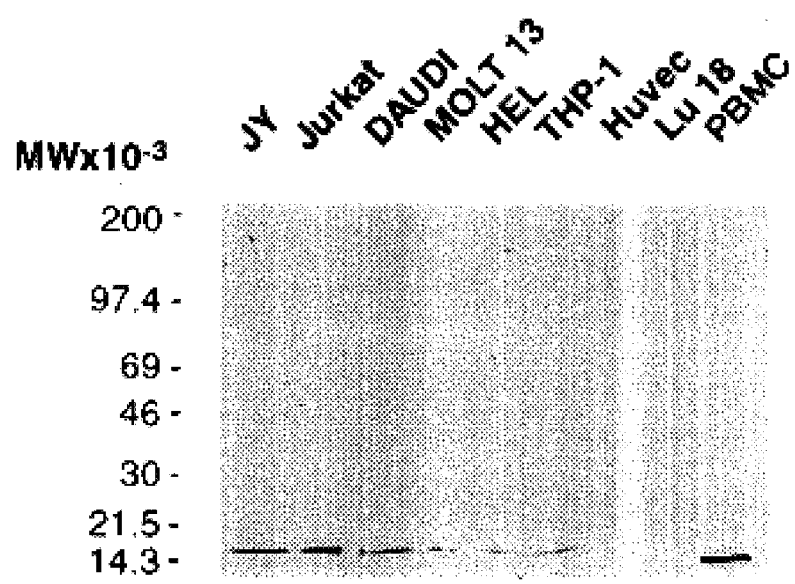
FIGS. 4A–C show the sequence analysis of Survivin and expression in cell lines. A. Predicted translation of the antisense EPR-1gene product (Survivin)(SEQ ID NO: 34).
Figures 2, 4C:
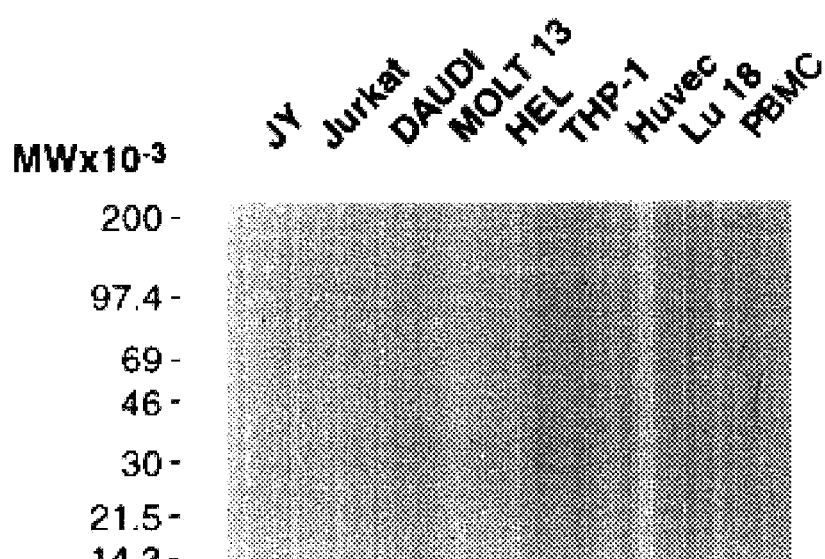

Thus, the Survivin proteins of the present invention include molecules having the amino acid sequences disclosed in FIG. 1; fragments thereof having a consecutive sequence of at least about 3, 5, 10 or 5 amino acid residues of the Survivin protein; amino acid sequence variants of such sequence wherein an amino acid residue has been inserted N- or C-terminal to, or within, the disclosed Survivin sequence; amino acid sequence variants of the disclosed Survivin sequence, or their fragments as defined above, that have been substituted by another residue. Contemplated variants further include those containing predetermined mutations by, e.g., homologous recombination, site-directed or PCR mutagenesis, and the corresponding Survivin proteins of other animal species, including but not limited to rabbit, rat, murine, porcine, bovine, ovine, equine and non-human primate species, and the alleles or other naturally occurring variants of the Survivin family of proteins; and derivatives wherein the Survivin protein has been covalently modified by substitution, chemical, enzymatic, or other appropriate means with a moiety other than a naturally occurring amino acid (for example a detectable moiety such as an enzyme or radioisotope). The recombinant Survivin protein also can be used to solve the molecular structure of Survivin by 2D-NMR, circular dichroism and X-ray crystallography, thus integrating the site-directed mutagenesis approach and the rational design of specific small molecule inhibitors.

As described below, members of the Survivin family of proteins can be used: 1) as a target to block Survivin mediated inhibition of cellular apoptosis, 2) to identify and isolate binding partners that bind Survivin, 3) in methods to identify agents that block the association of Survivin with a Survivin binding partner, 4) as a target to assay for Survivin mediated inhibition of cellular apoptosis, 5) as an agent to block cellular apoptosis, administered alone or as part of a combination therapy, 6) as a binding partner in an assay to quantitate circulating levels of anti-Survivin antibodies, 7) as an antigen to elicit production of anti-Survivin antibodies that in turn can be used in an assay to quantitate circulating levels of Survivin and or can be used for immunohistochemical purposes, and 8) as a therapeutic anti-cancer vaccine, or component of a polyvalent vaccine.

B. Anti-Survivin Antibodies

The present invention further provides antibodies that selectively bind to a Survivin protein. The anti-Survivin antibodies particularly contemplated include monoclonal and polyclonal antibodies as well as fragments containing the antigen binding domain and/or one or more complement determining regions.

Antibodies are generally prepared by inmunizing a suitable mammalian host using a Survivin protein, or fragment, in isolated or immunoconjugated form (Harlow, Antibodies, Cold Spring Harbor Press, NY (1989)). FIG. 9 provides a Jameson-Wolf plot of the antigenic index of various regions of Survivin. Such regions, in combination with the other structural analysis provided in FIG. 9, provide suitable fragments for use in generating Survivin specific antibodies. Methods for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective.

Administration of the Survivin immunogen is conducted generally by injection over a suitable time period and with use of a suitable adjuvant, as is generally understood in the art. During the immunization schedule, titers of antibodies can be taken to determine adequacy of antibody formation.

While the polyclonal antisera produced in this way may be satisfactory for some applications, for pharmaceutical compositions, monoclonal antibody preparations are preferred. Immortalized cell lines which secrete a desired monoclonal antibody may be prepared using the standard method of Kohler and Milstein or modifications which effect immortalization of lymphocytes or spleen cells, as is generally known. The immortalized cell lines secreting the desired antibodies are screened by immunoassay in which the antigen is the Survivin peptide. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of receptor can also be produced in the context of chimeras or CDR grafted antibodies of multiple species origin.

The antibodies thus produced are useful not only as modulators of the association of Survivin with a Survivin binding partner, but are also useful in immunoassays for detecting Survivin expression/activity and for the purification of Survivin and associated binding partners.

C. Survivin Encoding Nucleic Acid Molecules

The present invention further provides nucleic acid molecules that encode Survivin, and the related Survivin proteins herein described, preferably in isolated form For convenience, all Survivin encoding nucleic acid molecules will be referred to as the Survivin encoding nucleic acid molecule, the Survivin gene, or Survivin. As used herein, "nucleic acid" is defined as RNA or DNA that encodes a peptide as defined above, or is complementary to a nucleic acid sequence encoding such peptides, or hybridizes to such a nucleic acid and remains stably bound to it under stringent conditions, or encodes a polypeptide sharing at least 75% sequence identity, preferably at least 80%, and more preferably at least 85%, with the peptide sequences. Specifically contemplated are genomic DNA, cDNA, mRNA and antisense molecules, as well as nucleic acids based on an alternative backbone or including alternative bases whether derived from natural sources or synthesized. Such hybridizing or complementary nucleic acid, however, is defined further as being novel and unobvious over any prior art nucleic acid including that which encodes, hybridizes under appropriate stringency conditions, or is complementary to a nucleic acid encoding a Survivin protein according to the present invention.

As used herein, "stringent conditions" are conditions in which hybridization yields a clear and detectable sequence. Stringent conditions are those that (1) employ low ionic strength and high temperature for washing, for example, 0.015 M NaCl, 0.0015 M sodium citrate 0.1% SDS at 50° C.; or (2) employ during hybridization a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

As used herein, a nucleic acid molecule is said to be "isolated" when the nucleic acid molecule is substantially separated from contaminant nucleic acid encoding other polypeptides from the source of nucleic acid.

The present invention further provides fragments of the Survivin encoding nucleic acid molecule. As used herein, a fragment of a Survivin encoding nucleic acid molecule refers to a small portion of the entire protein encoding sequence. The size of the fragment will be determined by the intended use. For example, if the fragment is chosen so as to encode an active portion of the Survivin protein, such as the C-terminal β coils or the IAP motif, the fragment will need to be large enough to encode the functional region(s) of the Survivin protein. If the fragment is to be used as a nucleic acid probe or PCR primer, then the fragment length is chosen so as to obtain a relatively small number of false positives during probing/priming. FIG. 1 identifies fragments of the Survivin gene that are particularly useful as selective hybridization probes or PCR primers.

Fragments of the Survivin encoding nucleic acid molecules of the present invention (i.e., synthetic oligonucleotides) that are used as probes or specific primers for the polymerase chain reaction (PCR), or to synthesize gene sequences encoding Survivin proteins can easily be synthesized by chemical techniques, for example, the phosphotriester method of Matteucci, et al., *J Am Chem Soc* (1981) 103:3185–3191 or using automated synthesis methods. In addition, larger DNA segments can readily be prepared by well known methods, such as synthesis of a group of oligonucleotides that define various modular segments of the Survivin gene, followed by ligation of oligonucleotides to build the complete modified Survivin gene.

The Survivin encoding nucleic acid molecules of the present invention may further be modified so as to contain a detectable label for diagnostic and probe purposes. As described above such probes can be used to identify other members of the Survivin family of proteins and as described below, such probes can be used to detect Survivin expression and tumor growth potential. A variety of such labels are known in the art and can readily be employed with the Survivin encoding molecules herein described. Suitable labels include, but are not limited to, biotin, radiolabeled nucleotides and the like. A skilled artisan can employ any of the art known labels to obtain a labeled Survivin encoding nucleic acid molecule.

Since the Survivin gene is an antisense or reverse orientation of the EPR-1 gene, particularly preferred are single-stranded probes for use in diagnostic purposes. Specifically, single-stranded diagnostic probes can be used to selectively hybridize to mRNA that encodes Survivin. Single-stranded probes can be generated using known methods in which one strand of a double-stranded probe is isolated or in which a single stranded RNA probe is generated.

Modifications to the primary structure itself by deletion, addition, or alteration of the amino acids incorporated into the protein sequence during translation can be made without destroying the activity of the protein. Such substitutions or other alterations result in proteins having an amino acid sequence encoded by DNA falling within the contemplated scope of the present invention.

D. Isolation of other Survivin Encoding Nucleic Acid Molecules

As described above, the identification of the human Survivin encoding nucleic acid molecule allows a skilled artisan to isolate nucleic acid molecules that encode other members of the Survivin family of proteins in addition to the human sequence herein described.

Essentially, a skilled artisan can readily use the amino acid sequence of Survivin to generate antibody probes to screen expression libraries prepared from cells. Typically, polygonal antiserum from mammals such as rabbits immunized with the purified Survivin protein (as described below) or monoclonal antibodies can be used to probe a mammalian cDNA or genomic expression library, such as lambda gt11 library, to obtain the appropriate coding sequence for Survivin, or other members of the Survivin family of proteins. The cloned cDNA sequence can be expressed as a fusion protein, expressed directly using its own control sequences, or expressed by constructions using control sequences appropriate to the particular host used for expression of the enzyme. FIG. 1 identifies important antigenic and/or putative operative domains found in the Survivin protein sequence. Such regions are preferred sources of antigenic portions of the Survivin protein for the production of probe, diagnostic, and therapeutic antibodies.

Alternatively, a portion of the Survivin encoding sequence herein described can be synthesize and used as a probe to retrieve DNA encoding a member of the Survivin family of proteins from any mammalian organisms that contains such a protein. Oligomers containing approximately 18–20 nucleotides (encoding about a 6–7 amino acid stretch) are prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively clone a Survivin-encoding nucleic acid molecule. A PCR denature/anneal/extend cycle for using such PCR primers is well known in the art and can readily be adapted for use in isolating other Survivin encoding nucleic acid molecules. FIG. 1 identifies regions of the human Survivin gene that are particularly well suited for use as a probe or as primers.

E. rDNA Molecules Containing a Survivin Encoding Nucleic Acid Molecule

The present invention further provides recombinant DNA molecules (rDNAs) that contain a Survivin encoding sequence. As used herein, a rDNA molecule is a DNA molecule that has been subjected to molecular manipulation in vitro. Methods for generating rDNA molecules are well known in the art, for example, see Sambrook et al., Molecular Cloning (1989). In the preferred rDNA molecules, a Survivin encoding DNA sequence is operably linked to expression control sequences and/or vector sequences The choice of vector and/or expression control sequences to which one of the Survivin encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the Survivin gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a Survivin encoding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or viral promoter capable of directing the expression (transcription and translation) of the Survivin encoding gene sequences in a bacterial host cell, such as $E.$ $coli.$ A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), pPL and pKK223 available from Phamacia, Piscataway, N.J.

Expression vectors compatible with eukaryotic cells, preferably those compatible with vertebrate cells, can also be used to form rDNA molecules that contain a Survivin encoding sequence. Eukaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. Southern et al., *J Mol Anal Genet* (1982) 1:327–341. Alternatively, the selectable marker can be present on a separate plasmid, and the two vectors are introduced by co-transfection of the host cell, and selected by culturing in the appropriate drug for the selectable marker.

F. Host Cells Containing an Exogenously Supplied Survivin Encoding Nucleic Acid Molecule The present invention further provides host cells transformed with a nucleic acid molecule that encodes a Survivin protein of the present invention. The host cell can be either prokaryotic or eukaryotic. Eukaryotic cells useful for expression of a Survivin protein are not limited, so long as the cell line is compatible with cell culture methods and compatible with the propagation of the expression vector and expression of the Survivin gene product. Preferred eukaryotic host cells include, but are not limited to, yeast, insect and mammalian cells, preferably vertebrate cells such as those from a mouse, rat, monkey or human fibroblastic cell line, the most preferred being cells that do not naturally express a Survivin protein. Preferred eukaryotic host cells include the murine IL-3 dependent cell line BaF3, and the like eukaryotic tissue culture cell lines.

Any prokaryotic host can be used to express a Survivin-encoding rDNA molecule. The preferred prokaryotic host is *E coli.*

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al., *Proc Natl Acad Sci USA* (1972) 69:2110; and Maniatis et al., *Molecular Cloning, A Laboratory Manual*, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol* (1973) 52:456; Wigler et al., *Proc Natl Acad Sci USA* (1979) 76:1373–76.

Successfully transformed cells, i.e., cells that contain a rDNA molecule of the present invention, can be identified by well known techniques. For example, cells resulting from the introduction of an rDNA of the present invention can be cloned to produce single colonies. Cells from those colonies can be harvested, lysed and their DNA content examined for the presence of the rDNA using a method such as that described by Southern *J Mol Biol* (1975) 98:503, or Berent et al, *Biotech* (1985) 3:208 or the proteins produced from the cell assayed via an immunological method.

G. Production of Survivin Using a rDNA Molecule Encoding a Survivin Protein

The present invention further provides methods for producing a Survivin protein that uses one of the Survivin encoding nucleic acid molecules herein described. In general terms, the production of a recombinant form of a Survivin protein typically involves the following steps.

First, a nucleic acid molecule is obtained that encodes a Survivin protein, such as the nucleic acid molecule depicted in FIG. 1. If the Survivin encoding sequence is uninterrupted by introns, it is directly suitable for expression in any host. If not, then a spliced form of the Survivin encoding nucleic acid molecule can be generated and used or the intron containing nucleic acid molecule can be used in a compatible eukaryotic expression system.

The Survivin encoding nucleic acid molecule is then preferably placed in operable linkage with suitable control sequences, as described above, to form an expression unit containing the Survivin encoding sequences. The expression unit is used to transform a suitable host and the transformed host is cultured under conditions that allow the production of the Survivin protein. Optionally the Survivin protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with Survivin encoding sequences to produce a Survivin protein.

H. Inhibition of Cell Death Using Survivin

As provided above, Survivin has been shown to inhibit cellular apoptosis. Accordingly, Survivin can be used in methods to extend the life of cells. In general, cellular apoptosis can be inhibited by contacting a cell with Survivin.

The are a number of situation in which it is desirable to inhibit cellular apoptosis. For example, the death of cells in tissues and organs being prepared for transport and transplant can be inhibited using the Survivin protein. Alternatively, cells lines can be established for long term culture using Survivin encoding nucleic acid molecules expressed in the cell line.

Hence, Survivin protein or Survivin gene expression can be used as a means to inhibit cellular apoptosis. In cell culture systems, the Survivin protein can be introduced into a cell, for example via liposomal, Penetrin-1 delivery, or inclusion in the cell growth media, to inhibit apoptosis. Alternatively, the Survivin gene can be introduced and expressed in cells to increase the longevity of cells in culture. These provide means and methods for increasing the ability of cultured cells to produce desired compounds as well as provide methods of establishing long-term culture of primary explants of cells and tissues.

In tissue transplant, typically tissues and organs are stored and transported prior to transplant. Cell death, by mechanisms similar to apoptosis, can lead to the loss of viability of the tissues or organs. In this setting, infusion with Survivin protein can be used as a method to inhibit cell death in such tissues and organs.

There are pathological conditions characterized by premature and unwanted cellular apoptosis, for example in accelerated aging disorders. It is already known that inactivating mutations in a IAP protein may cause human diseases. The example is for the NAIP (see above). Studies of patients with SMA (Spinal muscular atrophy, a neurodegenrative disease that is thought to be caused by aberrantly increased apoptosis) has demonstrated that the NAIP gene is inactivated and deleted in 75% of these patients (Roy et al. 1995, Cell 80:167). By extension, inactivating mutations in Survivin can result in degenerative diseases characterized by aberrantly increased cell death. Haplotypic markers within and around the Survivin locus on chromosome 17q25 can be used in studies of population genetics to determine if that locus has already been implicated in diseases with increased apoptosis. In such cases, the Survivin gene or the Survivin protein can be used to treat the conditions. Accordingly, the Survivin protein, or a Survivin encoding nucleic acid molecule is administered to an individual as a means of treating abnormal apoptosis.

I. Methods to Identify Survivin Binding Partners

Another embodiment of the present invention provides methods for use in isolating and identifying binding partners of Survivin. Specifically, the Survivin protein can be used as a capture probe to identify Survivin binding partners. As used herein, a Survivin binding partner is a biomolecule (such as a protein, DNA or other cofactor) that binds to Survivin and mediates Survivin inhibition of cellular apoptosis.

In detail, a Survivin protein is mixed with an extract or fraction of a cell that expresses Survivin under conditions that allow the association of a binding partner with Survivin. After mixing, peptides that have become associated with Survivin are separated from the mixture. The binding partner that bound Survivin can then be removed and further analyzed.

To identify and isolate a binding partner, the entire Survivin protein can be used. Alternatively, a fragment of a Survivin protein can be used.

As used herein, a cellular extract refers to a preparation or fraction that is made from a lysed or disrupted cell. The preferred source of cellular extracts will be cells that naturally express Survivin. Examples of such cells include, but are not limited to tumor cells and embryonic tissues.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and the enzyme lysis. In addition, the cellular extract can be prepared from cells that have been freshly isolated from a subject or from cells or cell lines which have been cultured. A skilled artisan can readily adapt methods for preparing cellular extracts in order to obtain extracts for use in the present methods.

Once an extract of a cell is prepared, the extract is mixed with the Survivin protein under conditions in which association of Survivin with the binding partner can occur. A variety of conditions can be used, the most preferred being conditions that closely resemble conditions found in the cytoplasm of a Survivin-expressing cell. Features such as osmolarity, pH, temperature, and the concentration of cellular extract used, can be varied to optimize the association of the Survivin with the binding partner.

After mixing under appropriate conditions, Survivin is separated from the mixture. A variety of techniques can be utilized to separate the mixture. For example, antibodies specific to Survivin can be used to immunoprecipitate the Survivin and associated binding partner. Alternatively, standard chemical separation techniques such as chromatography and density/sediment centrifugation can be used.

After removal of nonassociated cellular constituents found in the extract, the binding partner can be dissociated from the Survivin protein using conventional methods. For example, dissociation can be accomplished by altering the salt concentration or pH of the mixture.

To aid in separating associated Survivin/binding partner pairs from the mixed extract, the Survivin protein can be immobilized on a solid support. For example, Survivin can be attached to a nitrocellulose matrix or acrylic beads. Attachment of Survivin to a solid support further aids in separating peptide/binding partner pair from other constituents found in the extract.

Alternatively, the Survivin-encoding nucleic acid molecule can be used in a yeast two-hybrid system. The yeast two-hybrid system has been used to identify other protein partner pairs and can readily be adapted to employ the Survivin encoding molecules herein described.

J. Use of Survivin Binding Partners

Once isolated, the Survivin binding partners obtained using the above described methods can be used for a variety of purposes. The binding partners can be used to generate antibodies that bind to the Survivin binding partner using techniques known in the art. Antibodies that bind a Survivin binding partner can be used to assay Survivin activity, as a therapeutic agent to modulate a biological or pathological process mediated by Survivin, or to purify the binding partner. These uses are described in detail below.

K. Methods to Identify Agents that Block Survivin/Binding Partner Interactions

Another embodiment of the present invention provides methods for identifying agents that reduce or block the association of Survivin with a Survivin binding partner. Specifically, Survivin is mixed with a Survivin binding partner in the presence and absence of an agent to be tested. After mixing under conditions that allow association of Survivin with the Survivin binding partner, the two mixtures are analyzed and compared to determine if the agent reduced or blocked the association of Survivin with the Survivin binding partner. Agents that block or reduce the association of Survivin with the Survivin binding partner will be identified as decreasing the amount of association present in the sample containing the tested agent.

As used herein, an agent is said to reduce or block Survivin/Survivin binding partner association when the presence of the agent decreases the extent to which or prevents the Survivin binding partner from becoming associated with Survivin. One class of agents will reduce or block the association by binding to the Survivin binding partner while another class of agents will reduce or block the association by binding to Survivin.

The Survivin binding partner used in the above assay can either be an isolated and fully characterized protein or can be a partially characterized protein that binds to Survivin or a Survivin binding partner that has been identified as being present in a cellular extract. It will be apparent to one of ordinary skill in the art that so long as the Survivin binding partner has been characterized by an identifiable property, e.g., molecular weight, the present assay can be used.

Agents that are assayed in the above method can be randomly selected or rationally selected or designed. As used herein, an agent is said to be randomly selected when the agent is chosen randomly without considering the specific sequences involved in the association of the Survivin with the Survivin binding partner. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. As described above, there are two sites of action for agents that block Survivin/Survivin binding partner interaction: the binding partner contact site on Survivin and the Survivin contact site on the Survivin binding partner. Agents can be rationally selected or rationally designed by utilizing the peptide sequences that make up the contact sites of the Survivin/Survivin binding partner pair. For example, a rationally selected peptide agent can be a peptide whose amino acid sequence is identical to the Survivin contact site on the Survivin binding partner. Such an agent will reduce or block the association of Survivin with the binding partner by binding to the Survivin binding partner.

The agents of the present invention can be, as examples, peptides, small molecules, vitamin derivatives, as well as carbohydrates. A skilled artisan can readily recognize that there is no limit as to the structural nature of the agents of the present invention. One class of agents of the present invention are peptide agents whose amino acid sequences are chosen based on the amino acid sequence of the Survivin protein.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of the Survivin or Survivin binding partner. As described above, antibodies are obtained by immunization of suitable mammalian subjects with peptides, containing as antigenic regions, those portions of the Survivin or binding partner, intended to be targeted by the antibodies. Critical regions include the contact sites involved in the association of the Survivin with the Survivin binding partner.

As discussed below, the important minimal sequence of residues involved in Survivin activity define a functional linear domain that can be effectively used as a bait for two-hybrid screening and identification of potential Survivin-associated molecules. Use of such Survivin fragments will significantly increase the specificity of the screening as opposed to using the full length molecule or the entire BIR domain and is therefore preferred. Similarly, this linear sequence can be also used as an affinity matrix also to isolate Survivin binding proteins using a biochemical affinity purification strategy.

L. Uses for Agents that Block the Association of Survivin with a Survivin Biding Partner As provided in the Background section, Survivin inhibits cellular apoptosis. Agents that reduce or block the interactions of Survivin with a Survivin binding partner can be used to modulate biological and pathologic processes associated with Survivin function and activity.

In detail, a biological or pathological process mediated by Survivin can be modulated by administering to a subject an agent that blocks the interaction of Survivin with a Survivin binding partner.

As used herein, a subject can be any mammal, so long as the mammal is in need of modulation of a pathological or biological process mediated by Survivin. The term "mammal" is meant an individual belonging to the class Mammalia. The invention is particularly useful in the treatment of human subjects.

As used herein, a biological or pathological process mediated by Survivin or Survivin binding to a Survivin binding partner refers to the wide variety of cellular events mediated by Survivin. Pathological processes refer to a category of biological processes which produce a deleterious effect. For example, a pathological process mediated by Survivin is the inhibition of cellular apoptosis in tumor cells. This pathological process can be modulated using agents that reduce or block Survivin/Survivin binding partner association or block Survivin expression As used herein, an agent is said to modulate a pathological process when the agent reduces the degree or severity of the process. For example, an agent is said to modulate tumor cell proliferation when the agent decrease the rate or extent of cell division.

M. Administration of Survivin or Agents that Affect Survivin Activity

The agents of the present invention, whether they be agents that block Survivin/binding partner association or the Survivin protein, can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. For example, to treat tumor cells as a means of blocking Survivin inhibition of apoptosis, an agent that blocks Survivin expression or the interaction of Survivin with a binding partner, is administered systemically or locally to the individual being treated. As described below, there are many methods that can readily be adapted to administer such agents.

The present invention further provides compositions containing Survivin or one or more agents that block Survivin/binding partner association. While individual needs vary, a determination of optimal ranges of effective amounts of each component is within the skill of the art. Typical dosages comprise 0.1 to 100 $\mu$g/kg body wt. The preferred dosages comprise 0.1 to 10 $\mu$g/kg body wt. The most preferred dosages comprise 0.1 to 1 $\mu$g/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice, such as chemotherapeutic agents.

N. Combination Therapy

Survivin, as well as agents of the present invention that modulate Survivin activity, can be provided alone, or in combination with another agents that modulate a particular biological or pathological process. For example, an agent of the present invention that reduces Survivin inhibited apoptosis can be administered in combination with other anti-cancer agents in methods to control cancer cell growth. Alternatively, Survivin can be administered with other protective agents as a means for reducing cellular apoptosis. As used herein, two agents are said to be administered in combination when the two agents are administered simultaneously or are administered independently in a fashion such that the agents will act at the same time.

Inhibition of Survivin activity/expression can be used in combination with conventional chemotherapies. The timing for using a chemotherapeutic agent in combination with inhibiting Suvivin activity/expression depends upon chemotherapeutic agent used and the tumor cell type treated. Examples of chemotherapeutic agents that can be used in combination with agents the effect Survivin activity/expression, includes, but is not limited to alkylating agents, such as cyclophosphamide (CTX; cytoxan), chlorambucil (CHL; leukeran), cisplatin (CisP; platinol) busulfan (myleran), melphalan, carmustine (BCNU), streptozotocin, triethylenemelamine (TEM), mitomycin C, and the like alkylating agents; anti-metabolites, such as methotrexate (MTX), etoposide (VP 16; vepesid) 6-mercaptopurine (6MP), 6-thioguanine (6TG), cytarabine (Ara-C), 5-fluorouracil (5FU), dacarbazine (DTIC), and the like anti-metabolites; antibiotics, such as actinomycin D, doxorubicin (DXR; adriamycin), daunorubicin (daunomycin), bleomycin, mithramycin and the like antibiotics; alkaloids, such as vinca alkaloids such as vincristine (VCR), vinblastine, and the like; and other antitumor agents, such as taxol and taxol derivatives, the cytostatic agents glucocorticoids such as dexamethasone (DEX; decadron) and corticosteroids such as prednisone, nucleoside enzyme inhibitors such as hydroxyurea, amino acid depleting enzymes such as asparaginase, and the like diverse antitumor agents.

The use of the cytotoxic agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using the present histoculture methods. Generally, the dosage will be reduced compared to the amount used in the absence of agents the effect Suvivin activity/expression.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

O. Methods for Identifying Survivin Expression and Survivin-Mediated Inhibition of Apoptosis The present invention further provides methods for identifying cells involved in Survivin-mediated inhibition of apoptosis as well as techniques that can be applied to diagnose biological and pathological processes associated with Survivin activity, the progression of such conditions, the susceptibility of such conditions to treatment and the effectiveness of treatment for such conditions. Specifically, Survivin-mediated inhibition of apoptosis can be identified by determining whether the Survivin protein is expressed in a cell. Cells expressing Survivin are considered to be inhibited from natural cellular apoptosis.

A variety of immunological and nucleic acid techniques can be used to determine if the Survivin protein, or a Survivin encoding mRNA, is produced in a particular cell. In one example, an extract of cells is prepared. The extract is then assayed to determine whether Survivin is expressed in the cell. The degree of expression provides a measurement of the degree of inhibition of apoptosis. An increase in expression is a measurement of an increased inhibition of apoptosis.

The measurement of Survivin expression can be used as a marker for a variety of purposes. In tumors, the present of Survivin expression correlates with the proliferative potential of the tumor. In the Examples, it is shown that lymphomas display varying levels of Survivin expression; lymphomas showing little to no Survivin expression are low grade lymphomas that can be effectively treated while lymphomas showing high levels of Survivin expression are high grade aggressive lymphomas that typically cannot be effectively treated. Accordingly, the level of Survivin expression in a lymphoma, or other tumor, can be used as a predictive measurement of the aggressiveness and treatability of the tumor: the higher the level of Survivin expression, the higher the aggressiveness of the tumor and the more difficult the treatment will be.

For example, to determine a tumor's proliferative potential or easy/prognosis of treatment, an extract is made of the tumor cells and the extract is then analyzed, for example, by gel electrophoresis, to determine whether a Survivin protein is present. The presence and level of Survivin correlates with the proliferative potential of the cancer and the ease of treatment. Alternatively, as described above, single-strand probes can be used to identify Survivin-encoding mRNA in the cellular extracts.

In addition to being a marker of tumor aggressiveness and treatment potential, Survivin expression can be used as a measurement of the effectiveness of anti-tumor therapy. In the Examples, it is shown that HL-60, promyelocytic cell line, had high levels of Survivin expression. Treatment of HL-60 cells with retenoic acid, and anti-cancer agent that acts by causing the differentiation of tumor cells, resulted in a reduction and elimination of Survivin expression. The reduction in expression correlated with the degree of differentiation, the greater the differentiation, the lower the level of Survivin expression. Accordingly, Survivin expression can be used to measure the effectiveness of anti-tumor treatment: if Survivin expression decreases during treatment, the treatment protocol is effective and can be continued, whereas if Survivin expression remains unaltered, a different therapeutic regime or protocol needs to be performed.

P. Other Methods to Control Survivin Expression

The present invention further provides additional methods that can be used to control Survivin expression in a cell. As discussed above and below, the Survivin promoter has a CPG island upstream from its promoter. CPG islands are known targets for DNA methylation. The DNA methylation sites in the CPG island serves as a means for regulating Survivin expression: methylation of CPG islands results in the suppression of transcription of the gene found downstream from the promoter. Accordingly, agents that methylate DNA, such as DNA methylase, and agents that stimulate the production of endogenous methylases, can be used to control Survivin expression. Specifically, Survivin expression in a cell can be reduced or eliminated by causing the cell to increase the level of DNA methylation, particularly at the CPG island found upstream from the Survivin gene.

In another method, Survivin expression can be reduced by increasing the level of EPR-1 expression. As shown in the Examples, Survivin expression and EPR-1 expression are generally mutually exclusive, expression of EPR-1 results in a decrease or elimination of Survivin expression and visa-a-versa. Accordingly, Survivin expression can be reduced by causing a cell to increase EPR-1 expression.

Q. Animal Models

We have isolated almost the complete structure of the mouse Survivin gene. The gene is very conserved with its human counterpart including sizes of introns, exons and intron-exon boundaries. The coding regions of the mouse Survivin gene are 88%, to the extent sequenced, identical to the human protein, thereby demonstrating strong evolutionary conservation. We have also determined the differential and developmentally-regulated distribution of Survivin during both human and mouse development. The availability of the complete structure of the mouse Survivin gene and protein will allow the preparation of targeting vectors for gene knockout experiments and a more rational approach for the generation of transgenic mice expressing Survivin under the control of tissue-specific promoters.

The Survivin gene and the Survivin protein can serve as a target for gene therapy in a variety of contexts. For example, in one application, Survivin-deficient non-human animals can be generated using standard knock-out procedures to inactivate a Survivin gene or, if such animals are non-viable, inducible Survivin antisense molecules can be used to regulate Survivin activity/expression. Alternatively, an animal can be altered so as to contain a Survivin or antisense-Survivin expression unit that directs the expression of Survivin or the antisense molecule in a tissue specific fashion. In such a uses, a non-human mammal, for example a mouse or a rat, is generated in which the expression of the Survivin gene is altered by inactivated or activation. This can be accomplished using a variety of art-known procedures such as targeted recombination. Once generated, the Survivin-deficient animal, the animal that expresses Survivin in a tissue specific manner, or an animal that expresses an antisense molecule can be used to 1) identify biological and pathological processes mediated by Survivin, 2) identify proteins and other genes that interact with Survivin, 3) identify agents that can be exogenously supplied to overcome Survivin deficiency and 4) serve as an appropriate screen for identifying mutations within Survivin that increase or decrease activity.

For example, it is possible to generate transgenic mice expressing the human minigene for Survivin in a tissue specific-fashion and test the effect of over-expression of the protein in district that normally do not contain Survivin. This strategy has been successfully used for another family of apoptosis inhibitors, namely bcl-2 (Veis et al., *Cell* (1993) 75:229). Such an approach can readily be applied to the Survivin protein and can be used to address the issue of a potential beneficial effect of Survivin in a specific tissue area to protect cells from apoptosis (transplant).

R. Survivin Gene Therapy

In another embodiment, genetic therapy can be used as a means for modulating a Survivin-mediated biological or pathological processes. For example, in tumor therapy, it may be desirable to introduce into the subject being treated a genetic expression unit that encodes a modulator of Survivin expression, such as an antisense encoding nucleic acid molecule. Such a modulator can either be constitutively produced or inducible within a cell or specific target cell. This allows a continual or inducible supply of a modulator of Survivin expression within the subject. Blocking Survivin expression allows for the control of tumor cell growth. Similarly, cells may be genetically engineered to express Survivin, e.g., in allograft pancreatic β cells for transplantation.

The level of Survivin gene expression may correlate with the level of resistance to apoptosis. Thus, Survivin genes also find use in anti-apoptosis gene therapy. In particular, a functional Survivin gene may be used to sustain neuronal cells that undergo apoptosis in the course of a neurodegenerative disease, lymphocytes (i.e., T cells and B cells), or cells that have been injured by ischemia.

Retroviral vectors, adenoviral vectors, adeno-associated viral vectors, or other viral vectors with the appropriate tropism for cells likely to be involved in apoptosis (for example, epithelial cells) may be used as a gene transfer delivery system for a therapeutic Survivin gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, current opinion in biotechnology 1:55–61, 1990; Sharp, The Lancet 337:1277–1278, 1991; Cornetta et al., Nucleic Acid Research and Molecular Biology 36:311–322, 1987; Anderson, Science 226:401–409, 1984; Moen, blood Cells 17:407–416, 1991; Miller et al., Biotechniques 7:980–990, 1989; Le Gal La Salle et al., Science 259:988–990, 1993; and Johnson, Chest 107:77S–83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches may also be employed for the introduction of therapeutic DNA into cells otherwise predicted to undergo apoptosis. For example, Survivin may be introduced into a neuron or a T cell by lipofection (Feigner et al., Proc. Natl. Acad. Sci. USA 84:7413, 1987; Ono et al., Neurosci. Lett. 117:259, 190; Brigham et al., Meth. Enz. 101:512, 1983), asialorosonucoid-polylysine conjugation (Wu et al., J. Biol. Chem. 263:14621, 1988; Wu et al., J. Biol. Chem. 264:16985, 1989); or, less preferably, microinjection under surgical conditions (Wolff et al., Science 247:1465, 1990).

For any of the methods of application described above, the therapeutic Survivin nucleic acid construct is preferably applied to the site of the predicted apoptosis event (for example, by injection). However, it may also be applied to tissue in the vicinity of the predicted apoptosis event or to a blood vessel supplying the cells predicted to undergo apoptosis.

In the constructs described, Survivin cDNA expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in neural cells, T cells, or B cells may be used to direct Survivin expression. The enhancers used could include, without limitation, those that are characterized as tissue- or cell-specific in their expression. Alternatively, if a Survivin genomic clone is used as a therapeutic construct (for example, following its isolation by hybridization with the Survivin cDNA described above), regulation may be mediated by the cognate regulatory sequences or, if desired, by regulatory sequences derived from a heterologous source, including any of the promoters or regulatory elements described above.

S. Use of the Survivin Promoter to Direct Gene Expression

The present invention further provides the promoter of the Survivin gene in a form that can be used in generating expression vectors. Specifically, the Survivin promoter, identified as being 5' from the ATG start codon in of Survivin, can be used to direct the expression of an operably linked protein encoding DNA sequence. Since the Survivin promoter does not have a TATA box, a skilled artisan would use a 5' fragment, such as nucleotides 2560–2920 (including exon 1). The Survivin promoter is expressed in fetal tissues and can therefore be used to target protein expression in specific cell types during specific stages of development. As discussed below, transfection of 3T3 cells with the c-myc oncogene results in the up-regulation of Survivin mRNA as detected by Northern blots. Accordingly, DNA encoding anti-tumor polypeptides under the control of the Survivin promoter could be used to transfect tumor cell where they would be expressed. A skilled artisan can readily use the Survivin promoter in expression vectors using methods known in the art.

T. Preventative Anti-Apoptotic Therapy

In a patient diagnosed to be heterozygous for a Survivin mutation or to be susceptible to Survivin mutations (even if those mutations do not yet result in alteration or loss of Survivin biological activity), or a patient diagnosed with a degenerative disease (e.g., motor neuron degenerative diseases such as SMA or ALS diseases), or diagnosed as HIV positive, any of the disclosed therapies may be administered before the occurrence of the disease phenotype. For example, the therapies may be provided to a patient who is HIV positive but does not yet show a diminished T cell count or other overt signs of AIDS. In particular, compounds shown to increase Survivin expression or Survivin biological activity may be administered by any standard dosage and route of administration. Alternatively, gene therapy using a Survivin expression construct may be undertaken to reverse or prevent the cell defect prior to the development of the degenerative disease.

The methods of the instant invention may be used to reduce or diagnose the disorders described herein in any mammal, for example, humans, domestics pets, or livestock. Where a non-human mammal is treated or diagnosed, the Survivin polypeptide, nucleic acid, or antibody employed is preferably specific for that species.

U. Examples of Additional Apoptosis Assays

In addition to the foregoing discussion, specific examples of apoptosis assays are also provided in the following references. Assays for apoptosis in lymphocytes are disclosed by: Li et al., "Induction of apoptosis in uninfected lymphocytes by HIV-1 Tat protein", Science 268:429–431, 1995; Gibellini et al., "Tat-expressing Jurkat cells show an increased resistance to different apoptotic stimuli, including acute human immunodeficiency virus-type 1 (HIV-1) infection", Br. J. Haematol. 89:24–33, 1995; Martin et al., "HIV-1 infection of human CD4+ T cells in vitro. Differential induction of apoptosis in these cells." J. Immunol. 152:330–42, 1994; Terai et al., "Apoptosis as a mechanism of cell death in cultured T lymphoblasts acutely infected with HIV-1", J. Clin Invest. 87:1710–5, 1991; Dhein et al., "Autocrine T-cell suicide mediated by APO-1/(Fas/CD95) 11, Nature 373:438–441, 1995; Katsikis et al., "Fas antigen stimulation induces marked apoptosis of T lymphocytes in human immunodeficiency virus-infected individuals", J. Exp. Med. 1815:2029–2036, 1995; Westendorp et al., Sensitization of T cells to CD95-mediated apoptosis by HIV-1 Tat and gp120", Nature 375:497, 1995; DeRossi et al., Virology 198:234–44, 1994.

Assays for apoptosis in fibroblasts are disclosed by: Vossbeck et al., "Direct transforming activity of TGF-beta on rat fibroblasts", Int. J. Cancer 61:92–97, 1995; Goruppi et al., "Dissection of c-myc domains involved in S phase induction of HIH3T3 fibroblasts", Oncogene 9:1537–44, 1994; Fernandez et al., "Differential sensitivity of normal and Ha-ras transformed C3H mouse embryo fibroblasts tumor necrosis factor, induction of bcl-2, c-myc, and manganese superoxide dismutase in resistant cells", Oncogene 9:2009–17, 1994; Harrington et a., "c Myc-induced apoptosis in fibroblasts is inhibited by specific cytokines", EMBO J., 13:3286–3295, 1994; Itoh et al., "A novel protein domain required for apoptosis. Mutational analysis of human Fas antigen", J. Biol. Chem. 268:10932–7, 1993.

Assays for apoptosis in neuronal cells are disclosed by: Melino et al., "Tissue transglutaminase and apoptosis: sense and antisense transfection studies with human neuroblastoma cells", Mol. Cell Biol. 14:6584–6596, 1994; Rosenblaum et al., "Evidence for hypoxia-induced, programmed cell death of cultured neurons", Ann Neurol. 36:864–870, 1994; Sato et al., "Neuronal differentiation of PC12 cells as a result of prevention of cell death by bcl-2", J. Neurobiol. 25:1227–1234, 1994; Ferrari et al., "N-acetylcysteine D- and L-stereoisomers prevents apoptotic death of neuronal cells", J. Neurosci. 1516:2857–2866, 1995; Talley et al., "Tumor necrosis factor alpha-induced apoptosis in human neuronal cells: protection by the antioxidant N-acetylcysteine and the genes bcl-2 and crma", Mol. Cell Biol. 1585:2359–2366, 1995; Talley et al., "Tumor Necrosis Factor Alpha-Induced Apoptosis in Human Neuronal Cells: Protection by the Antioxidant N-Acetylcysteine and the Genes bcl-2 and crma", Mol. Cell. Biol. 15:2359–2366, 1995; Walkinshaw et al., "Induction of apoptosis in catecholaminergic PC12 cells by L-DOPA. Implications for the treatment of Parkinson's disease," J. Clin. Invest. 95:2458–2464, 1995.

Assays for apoptosis in insect cells are disclosed by: Clem et al., "Prevention of apoptosis by a baculovirus gene during infection on insect cells", Science 254:1388–90, 1991; Crook et al., "An apoptosis-inhibiting baculovirus gene with a zinc finger-like motif", J. Virol: 67:2168–74, 1993; Rabizadeh et al., "Expression of the baculovirus p35 gene inhibits mammalian neural cell death", J. Neurochem. 61:2318–21, 1993; Birnbaum et al., "An apoptosis inhibiting gene from a nuclear polyhedrosis virus encoding a polypeptide with Cys/His sequence motifs", J. Virol. 68:2521–8, 1994; Clem et al., *Mol. Cell. Biol.* 14:5212–5222, 1994.

V. Use of Survivin in Tissue and Organ Transplantation

The present invention includes methods of inhibiting or preventing tissue or organ transplant rejection in a subject, comprising the local administration of a Survivin polypeptide, Survivin polypeptide fragment, an apoptosis, inhibiting peptidomimetic thereof, a transgene encoding a Survivin polypeptide or a transgene encoding a Survivin polypeptide fragment to the tissue, organ or to a site proximal to the transplant. Local delivery of the polypeptides, peptidomimetics to the tissue, organ or to a site proximal to the transplant is accomplished by any means commonly available, including but not limited to direct local perfusion, injection, microsponges, microcapsules, liposomes or time-released delivery vehicles.

Local delivery of a transgene encoding a Survivin polypeptide or a transgene encoding a Survivin polypeptide fragment to the tissue, organ or to a site proximal to the transplant may be accomplished with any available vector, via lipofection or via direct plasmid DNA injection See Qin et al. (1995) *Transplantation* 59(6): 809–816; Le Coultre et al. (1997) *Eur. J. Pediatr. Surg.* 7(4):221–226; Wang et al. (1992) *Transplantation* 53(3):703–705; Wang et al. (1996) *Transplantation* 61(12):1726–1729; Schmid et al., (1997) *Eur. J. Cardiothorac. Surg.* 11(6):1023–28; and Boasquevisque, C. et al. (1997) *Ann. Thorac. Surg.* 63(6):1556–1561. Vectors encoding the transgene include both replicable and replication, defective vectors, such as retroviral vectors, adenovirus vectors or other vectors with the appropriate tropism for the cells likely to be involved in apoptosis or cells proximal to the site of apoptosis. In the transgene constructs, expression can be directed from any suitable promoter, including tissue specific promoters which direct gene expression in specific cell types, such as the human insulin promoter. Local delivery of the transgene to the tissue, organ or to a site proximal to the transplant is accomplished by any means commonly available, including but not limited to direct local perfusion, injection, microsponges, microcapsules, liposomes or time-released delivery vehicles.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure. Other generic configurations will be apparent to one skilled in the art. All journal articles and other published documents such as patents and patent applications are hereby incorporated by reference in their entireties.

EXAMPLES

Example 1

Experimental Procedures and Cloning

Cells and cell culture. The following cell lines were obtained from American Type Culture Collection (ATCC, Rockville, Md.), erythroleukemia HEL, B-lymphoma Daudi and JY, monocytic THP-1, T leukemia Jurkat, epithelial carcinoma HeLa, promyelocytic HL-60, and non-transformed human lung fibroblast Lu18. The T leukemia cell line MOLT13 was characterized previously (Altieri, D. C., *FASEB J* (1995) 9:860–865). Cells were maintained in culture in complete medium RPMI 1640 or DMEM (HeLa, Lu18) (BioWittaker, Walkersville, Md.), supplemented with 10% heat-inactivated fetal bovine serum (FBS, Whittaker), 2 mM L-glutamine, and 10 mM HEPES. Human umbilical vein endothelial cells (HUVEC) were isolated by collagenase treatment and maintained in culture in DMEM medium supplemented with 20% FBS, 2 mM L-glutamine and endothelial cell growth factor (Biomedical Technologies, Stoughton, Mass.).

Peripheral blood mononuclear cells (PBMC) were isolated from heparinized blood collected from normal informed volunteers by differential centrifugation on Ficoll-Hypaque (Pharmacia, Piscataway, N.J.) at 400 g for 22° C., and washed in phosphate buffered saline (PBS), pH 7.4. In some experiments, HL-60 cells were terminally differentiated to a mature monocytic phenotype by a 72 h culture in the presence of 0.1 $\mu$M 1, 25-dihydroxy-vitamin $D_3$ and 17.8 $\mu$g/ml indomethacin (Sigma Chemical Co., St. Louis, Mo.). De novo induction of differentiation-dependent markers on vitamin $D_3$-treated HL-60 cells, including CD11b/CD18 integrin (Hickstein, D. D. et al., *J Immunol* (1987) 138:513–519) was determined by flow cytometry with anti-CD11b mAb LM2/1.

Genomic and cDNA cloning, chromosomal localization and Southern blots. A human P1 genomic library (Genome Systems, St. Louis, Mo.) was screened by hybridization with a 1.6 kb fragment containing the complete human EPR-1 cDNA (Altieri, D. C., *FASEB J* (1995) 9:860–865). Three overlapping clones were isolated, purified and confirmed by Southern hybridization with the EPR-1 cDNA. Hybridizing fragments generated by restriction digest with BamHI, HindIII and XbaI (Boehringer Mannheim, Indianapolis, Ind.) were cloned in pBluescript (pBSKS$^-$, Stratagene, San Diego, Calif.) for further analysis. An overlapping contig spanning 14796 bp from two EPR-1-hybridizing P1 clones was arrayed, characterized by restriction analysis, and completely sequenced on both strands by Taq FS polymerase-based automated sequencing using a Applied BioSystem Prism 377 automated sequencer (Foster City, Calif.). In some experiments, 10 mg of total RNA extracted from HeLa cells by the guanidinium isothiocyanate method was primed with EPR-1 forward "sense" oligonucleotide C3/27 (bp 80–102) and reverse transcribed in the presence of 200 U of Superscript II (Life Science, Grand Island, N.Y.) for 50 min at 42° C.

The resulting cDNA was amplified by PCR in the presence of 0.5 mg of EPR-1-derived primers T5/27 (bp 161–184) and G11/16 (1124–1098, numbering from the EPR-1 coding sequence), 200 mM dNTPs (New England Biolabs, Beverly, Mass.) and 2 U Vent DNA polymerase (New England Biolabs) in a total volume of 50 ml. After 35 cycles of amplification with annealing at 58° C. for 1 min, denaturation at 94° C. for 1 min and extension at 72° C. for 1 min, the product was analyzed by agarose gel electrophoresis, subcloned in pCRII (Invitrogen Corp., San Diego, Calif.), and completely sequenced on both strands. Contig assembly, and DNA and protein sequence analyses were performed using Lasergene (DNASTAR, Madison, Wis.) and MacVector (Eastman Kodak, Rochester, N.Y.) software packages. Chromosomal location of the EPR-1-hybridizing gene was carried out by fluorescence in situ hybridization. Purified DNA from a EPR-1-hybridizing P1 clone was labeled with digoxigenin dUTP (Amersham Corp., Arlington Heights, Ill.) by nick translation.

The labeled probe was combined with sheared human DNA and hybridized to normal metaphase chromosomes derived from phytohemagglutinin-stimulated PBMC in a solution containing 50% formamide, 10% dextran sulfate and 2×SSC. For two-color staining, biotin-conjugated probe D17Z1, specific for the centromere of chromosome 17, was co-hybridized with the digoxigenin-labeled P1 clone. Specific staining was detected by incubating the hybridized slides with fluoresceinated anti-digoxigenin antibodies and Texas red avidin. Slides were counterstained with propidium iodide for one color labeling, or with DAPI for two color labeling. A total of 80 metaphase cells were analyzed with 69 cells exhibiting specific labeling. For Southern hybridization, human genomic DNA was extracted from HeLa cells according to published protocols, digested with EcoRI, BamHI, XbaI or HindIII, separated on a 0.8% agarose gel and transferred to GeneScreen nylon membranes (New England Nuclear, Boston, Mass.).

After UV cross-linking (Stratalinker, Stratagene, San Diego, Calif.), the membrane was prehybridized with 100 mg/ml of denatured salmon sperm DNA (Promega Corp. Madison, Wis.) in 5×SSC, 0.5% SDS, 5× Denhardt's solution and 0.1% sodium pyrophosphate at 65° C. in a roller hybridization oven (Hoefer Scientific, San Francisco, Calif.). Hybridization was carried out with gel-purified (GenClean Bio101, Vista, Calif.), $^{32}$P-dCTP (Amersham) random-primed labeled (Boehringer-Mannheim, Indianapolis, Ind.) 1.6 kb EPR-1 cDNA for 16 h at 65° C.

After two washes in 2×SSC, 1% SDS for 30 min at 65° C., and 0.2×SSC at 22° C., radioactive bands were visualized by autoradiography using a Kodak X-Omat AR X-ray film and intensifying screens (DuPont de Nemours, Wilmington, Del.). In other experiments, cultured lymphoblastoid cells were embedded in LMP agarose (Bio Rad, Richmond, Calif.) at the concentration of $2 \times 10^6/220$ µl block and DNA was extracted by standard procedures. After block digestion with MluI or NotI, samples were separated by pulsed field gel electrophoresis on a 1% agarose gel for 20 h at 200 V with a pulse time of 75 sec using a Bio-Rad CHEF DRII apparatus (Hercules, Calif.). After transfer to nylon membranes, and UV cross-linking, hybridization with the EPR-1 cDNA and washes were carried out as described above.

In another series of experiments, a blot containing aliquots of genomic DNA isolated from several species (Clontech, San Francisco, Calif.) was hybridized with a 3' 548 bp fragment of the EPR-1 cDNA, as described above.

Northern blots. Single strand probes specific for sense or antisense EPR-1 sequences were generated by asymmetric PCR amplification of a 301 bp fragment of the EPR-1 cDNA. The template, comprising the first 5' 226 bp of the EPR-1 coding sequence plus 75 bp of the retained regulatory intron (Altieri, D. C., FASEB J (1995) 9:860–865), was generated by restriction digest of the EPR-1 cDNA with EcoRI (cloning site) and SacII, gel-purified, and mixed in a total volume of 10 ml with 15 pmol dNTP (New England Biolabs), 7.5 pmol dCTP, and 25 mCi $^{32}$P-dCTP (Amersham), in the presence of 20 mM Tris HCl, 50 mM KCl, pH 8.4, 1.5 mM MgCl$_2$, and 2.5 U of Taq DNA polymerase (Life Science).

Generation of a EPR-1-specific antisense probe was carried out by addition of 0.2 mg/ml of a "SacII" reverse oligonucleotide 5'TGCTGGCCGCTCCTCCCTC3' SEQ ID NO: 1, while extension of the EPR-1 positive strand and generation of a Survivin-specific probe was preformed using 0.2 mg/ml of forward F11 oligonucleotide 5'ATGACCTCCAGAGGTTTC3' SEQ ID NO: 2. Twenty-five cycles of amplification were carried with denaturation at 94° C. for 1 min, annealing at 52° C. for 1 min, and extension at 72° C. for 1 min. The EPR-1 sense or antisense probes were centrifuged through a Sephadex G-50 spin column (Worthington Biochemical Corp., Freehold, N.J.) at 14,000 g for 5 min to separate free from incorporated radioactivity, heated at 100° C. for 2 min, and immediately added to the hybridization reaction.

Identical strand-specific probes were used for hybridization of multiple tissue blots of adult or fetal human mRNA (Clontech), in 5×SSPE, 10× Denhardt's solution, 2% SDS, 100 mg/ml denatured salmon sperm DNA at 60° C. for 14 h, and washes at 60° C., as described above. Aliquots of total RNA extracted from undifferentiated or vitamin D$_3$ terminally differentiated HL-60 cells, were processed for Northern hybridization with Survivin-specific single strand probe, as described above.

Example 2

Production of Anti-Survivin Antibodies

A Survivin sequence-specific antibody, called JC700, was produced and characterized as follows. A seventeenmer peptide corresponding to the Survivin sequence A$^3$PTLPPAWQPFLKDHRI$^{19}$ SEQ ID NO: 3, was synthesized and characterized by mass spectrometry. One hundred mg of the Survivin peptide were coupled in a 1:1 ratio to Keyhole Limpet Hemocyanin and injected s. c. into a rabbit in complete Freund's adjuvant. After a 4-week interval., animals were boosted with s. c. injection of 100 mg of peptide in incomplete Freund's adjuvant and sequentially boosted and bled at alternate weeks.

Purification of the anti-Survivin antibody was carried out by affinity chromatography on a peptide-Sepharose matrix (5 mg/ml of peptide) with elution of the specific IgG fraction in 1 mM glycine, pH 2.5. Specificity of the affinity-purified anti-Survivin antibody, designated JC700, was determined by ELISA against the immobilized Survivin peptide or a control EPR-1 peptide by absorbance at OD$_{405}$.

Example 3

Production of a Monoclonal Antibody against a Survivin Fusion Protein

The Survivin cDNA was expressed as a GST-fusion protein in E. Coli BL21 strain and purified to homogeneity with removal of the GST frame. The purified protein was used to inject mice and generate monoclonal antibodies using standard hybridoma technology. Three independent mAbs were isolated, cloned twice by limiting dilution and further characterized. One of the new anti-Survivin mAbs, designated 8E2, recognized the immobilized, purified recombinant Survivin by ELISA and bound to Survivin in immunoblots, as shown in FIG. 11.

Example 4

Immunoblotting and In Situ Hybridization

For immunoblotting, aliquots of SDS-solubilized extracts of various transformed cell lines, non-transformed HUVEC, PBMC or Lu18, or undifferentiated or vitamin D$_3$-differentiated HL-60 cells, were normalized for protein content by absorbance at OD$_{280}$, separated by electrophoresis on a 5–20% SDS polyacrylamide gradient gel under non reducing conditions, and electroblotted to Immobilon membranes (Millipore Corp., New Bedford, Mass.) at 1.1 A for 30 min at 22° C. The membrane was blocked in TBS, pH 7.4, plus 5% milk, and incubated with 20 mg/ml of control non-immune rabbit IgG or anti-Survivin antibody JC700 for 1 h at 22° C., followed by washes in TBS, pH 7.4, and addition of a 1:7500 dilution of alkaline phosphatase-conjugated goat anti-rabbit IgG (Promega) for 30 min at 22° C. Binding of the primary antibody was revealed by addition of 75 mg/ml nitro blue tetrazolium in 70% dimethylformamide (Sigma Chemical Co., St Louis, Mo.) plus 50 mg/ml 5-bromo-4-chloro-3-indolyl phosphate (Sigma) in 100% dimethylformamide.

Tissue samples, immunohistochemistry and in situ hybridization. Tissue samples from colon adenocarcinoma (6 cases), lung squamous cell carcinoma (6 cases), lung adenocarcinoma (9 cases), pancreas adenocarcinoma (2 cases), invasive breast adenocarcinoma (7 cases), were obtained from the archives of Yale-New Haven Hospital and used in the present study. Samples of 44 high grade lymphoma tissues and 7 low grade lymphoma tissue was also obtained. Tissue samples were fixed in formalin, embedded in paraffin, cut in 5 μm sections, deparaffinized in xylene, and rehydrated in graded alcohol followed by quenching of endogenous peroxidase activity by treatment with 2% $H_2O_2$ in methanol.

For immunostaining, the slides were boiled for 5 min in a standard pressure cooker, blocked in 10% normal goat serum, and incubated with affinity-purified anti-Survivin antibody JC700 (20 μg/ml) for 14 h at 4° C. After washes in PBS, pH 7.4, slides were further incubated with biotin-conjugated goat anti-rabbit IgG (Vector Laboratories, Burlingame, Calif.) for 30 min at 22° C., and washed in PBS, pH 7.4. After addition of streptavidin-biotin conjugated peroxidase (Boehringer Mannheim) for 30 min at 22° C., slides were washed, and binding of the primary mAbs was revealed by addition of 3'-3'-diamino-benzidine (DAB) and counterstaining with hematoxylin.

Negative controls were carried out by replacing the primary antibody with normal goat serum, under the same experimental conditions. In some experiments, aliquots of JC700 antibody were pre-adsorbed with 25 mg/ml of the Survivin 3–19 peptide before tissue staining. For in situ hybridization, 1 μg of the Survivin cDNA containing the entire coding sequence plus 271 bp of 3' untranslated region in pcDNA3 (Invitrogen), was completely digested with EcoRI and transcribed in the antisense orientation using T7 RNA polymerase in the presence of digoxigenin 11-uridine-5' triphosphate (Boehringer Mannheim). Tissue slides were coated with 1% gelatin, 0.1% chrome-alum, baked at 120° C. for 2 h, and stored dust-free at 22° C. Sections were deparaffinized and rehydrated through graded alcohol, digested with proteinase K (1 μg/ml in 100 mM Tris HCl pH 8.7, 50 mM EDTA) for 30 min at 37° C., and acetylated in 0.25% acetic anhydride acid and 100 mM triethanolamine pH 8.0 for 10 min at 22° C.

Detection of Survivin mRNA in human tissues was carried out by in situ hybridization of the Survivin antisense riboprobe in a buffer containing 4×SSC, 1× Denhardt's solution, 50% deionized formamide, 250 μg/ml yeast tRNA, 500 μg/ml salmon sperm DNA and 5% dextran for 16 h at 50° C. After washes in 2×SSC for 90 min at 48° C., immobilized digoxigenin was detected using an anti-digoxigenin mAb (Boehringer Mannheim) at a 1:3000 dilution, and revealed by alkaline phosphatase staining with NBT/BCIP cytochemical stain.

Example 5

Expression of Survivin in Human Cancers

Figure 6A:
Figure 6B:
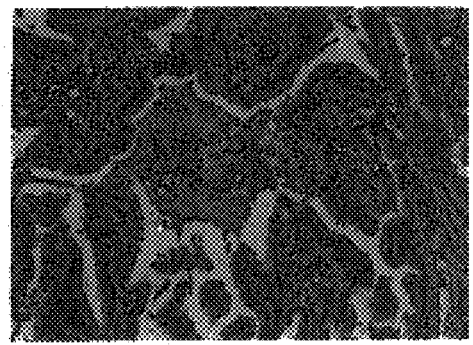
Figure 6C:
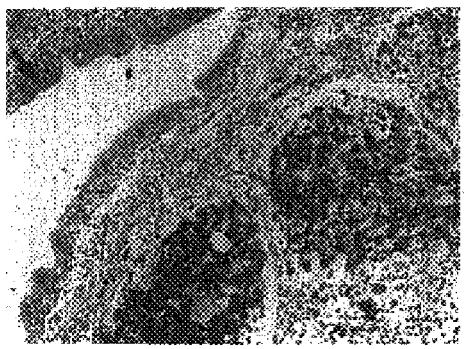

Survivin is prominently expressed in human cancer. For its abundant distribution in transformed cell types, a potential expression of Survivin in neoplasia was investigated, in vivo. Immunohistochemical analysis of formalin-fixed, paraffin embedded tissue sections with the affinity-purified anti-Survivin JC700 antibody demonstrated abundant expression of Survivin in all cases examined of human lung cancer, including adenocarcinoma (FIG. 6A), and squamous cell carcinoma (FIG. 6C). Consistent with the topography of other LAP proteins (Duckett, C. S. et al., *EMBO J* (1996) 15:2685–2694), expression of the protein was exclusively localized to the cytoplasm of tumor cells, while the adjacent normal gland epithelium of the lung did not express Survivin (FIG. 6C, arrow). No staining was observed when the anti-Survivin antibody was substituted with control goat serum (not shown), or after pre-adsorption with the immunizing Survivin 3–19 peptide (FIG. 6B), thus confirming the specificity of the observed recognition.

Figure 6D:
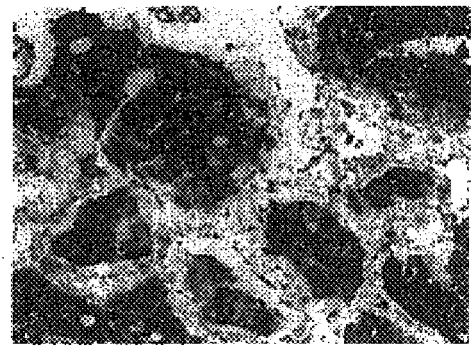
Figure 6E:
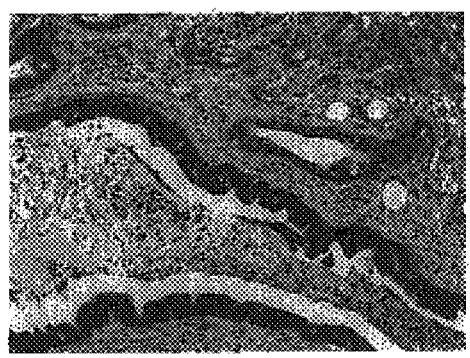
Figure 6F:
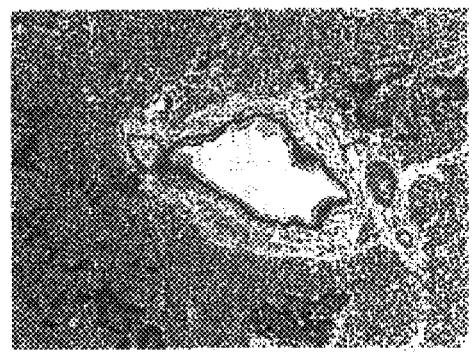
Figure 6G:
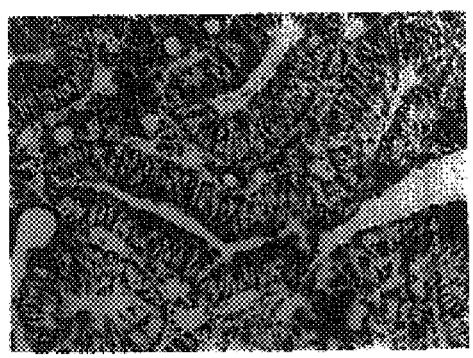
Figure 6H:

Prominent accumulation of Survivin mRNA in squamous lung cell carcinoma was independently demonstrated by in situ hybridization with a Survivin-specific single strand riboprobe (FIG. 6D). Survivin was also abundantly detected in all cases examined of adenocarcinoma of pancreas (FIG. 6E), and breast (not shown) by immunohistochemistry, and colon (FIG. 6G) by in situ hybridization. However, consistent with its absence in non-transformed cell types HUVEC and Lu18 (FIG. 4C), in mature tissues (FIG. 3), and in terminally-differentiated HL-60 cells (FIG. 5), no reactivity of the anti-Survivin JC700 antibody was observed with normal exocrine pancreatic epithelial cells by imnmunohistochemistry (FIG. 6F), and no Survivin mRNA was found in the adjacent non-neoplastic colon gland epithelium by in situ hybridization (FIG. 6H).

Expression of Survivin in Lymphoma Tissue. Tissue samples were obtained from 44 patients with aggressive, high grade lymphoma and 7 samples were obtained from 7 patients with non-aggressive, low grade lymphoma. The sample were treated as described above and examined for Survivin expression. None of the low grade lymphoma samples displayed Survivin expression whereas 27 samples (61%) from patients with high grade lymphoma expressed Survivin.

Example 6

Expression of Survivin in other Cancers

In addition to the malignant forms of cancer discussed above, the expression of Survivin in other types of cancers was investigated in the inventors' laboratory or collaboratively with other academic investigators. Survivin was found prominently expressed in the most aggressive and metastatic forms of malignant thymoma (~100 cases tested), in head and-neck squamous cell carcinoma (~140 cases) and in all forms of prostate cancer (15 cases), including the transition lesion of benign prostate hyperplasia. The most aggressive forms of neuroblastoma are also positive for Survivin as discussed below.

Example 7

Tissue Specific Expression of Survivin

Survivin, was recently found in all the most common human cancers but not in normal, terminally differentiated adult tissues. The expression of Survivin in embryonic and fetal development was investigated. Immunohistochemistry and in situ hybridization studies demonstrated strong expression of Survivin in several apoptosis-regulated fetal tissues, including the stem cell layer of stratified epithelia, endocrine pancreas and thymic medulla, with a pattern non-overlapping with that of another apoptosis inhibitor, i.e. bcl-2. A sequence-specific antibody to Survivin immunoblotted a single ~16.5 kD Survivin band in human fetal lung, liver, heart, kidney and gastrointestinal tract. In mouse embryo, prominent and nearly ubiquitous distribution of Survivin was found at embryonic date (E) 11.5, whereas at E15–21, Survivin expression was restricted to the distal bronchiolar epithelium of the lung and neural crest-derived cells, including dorsal root ganglion neurons, hypophysis and the chorioid plexus. These data suggest that expression of Survivin in embryonic and fetal development may contribute to tissue homeostasis and differentiation independently of bcl-2.

Example 8

Preparation of Survivin Transfectants

Inducible Survivin antisense transfectants and apoptosis/proliferation experiments. A 708 bp SmaI-EcoRI fragment comprising nucleotides 379–1087 of the EPR-1 cDNA, was directionally cloned in the sense orientation in the mammalian cell expression vector pML1 (generously provided by Dr. R Pytela, Cardiovascular Research Institute, University of California, San Francisco). The vector is derived from the episomal mammalian cell expression vector pCEP4 by replacing the cytomegalovirus promoter cassette with the MMT1 promoter, directing $Zn^{2+}$-dependent expression of recombinant proteins in mammalian cells (Lukashev, M. E. et al., *J Biol Chem* (1994) 269:18311–18314).

Ten million HeLa cells were incubated with 10 mg of pML1 DNA containing the Survivin antisense construct plus 50 mg of salmon sperm DNA for 15 min on ice, followed by a single electric pulse delivered by a Gene Pulser apparatus (Bio-Rad) at 350 V at 960 $\mu$F. Forty-eight h after transfection, cells were diluted fifteen fold, plated onto 100 mm diameter tissue culture dishes and selected for 4 weeks in complete growth medium containing 0.4 mg/ml hygromycin. Apoptosis in control cultures or Survivin antisense HeLa cell transfectants was evaluated by in situ detection of internucleosomal DNA degradation after $Zn^{2+}$-dependent induction of EPR-1 transcription under serum-starving conditions.

Briefly, control or antisense Survivin transfectants were treated with 200 mM $ZnSO_4$ in 0% FBS for 24 h at 37° C. Cells were harvested, centrifuged at 800 g for 10 min at 4° C., and the pellet was fixed in 10% formalin overnight, dehydrated, embedded in paraffin blocks, and sections of 3–5 mm were put on high adhesive slides. Samples were treated with 20 mg/ml proteinase K for 15 min at 22° C., washed in distilled water, quenched of endogenous peroxidase in 2% $H_2O_2$ in PBS, and subsequently mixed with digoxigenin-labeled dUTP in the presence of terminal deoxynucleotidyl transferase (TdT) followed by peroxidase conjugated anti-digoxigenin antibody.

Nuclear staining in apoptotic cells was detected by DAB, according to the manufacturer's instructions (AptoTag, Oncor, Gaithersburg, Md.). Control experiments were performed by omitting the enzyme incubation step. Morphologic features of apoptotic cells (apoptotic bodies) under the various conditions tested were detected by hematoxylin/eosin staining of the same slides.

For proliferation experiments, vector control HeLa cells or Survivin antisense transfectants were plated at $20 \times 10^4$/well onto 24-well tissue culture plates (Costar), induced with 200 mM $ZnSO_4$ for 16 h at 37° C., harvested at 24 h intervals, and cell proliferation under the various conditions tested was determined microscopically by direct cell count. Down-regulation of Survivin expression under these experimental conditions was assessed by immunoblotting with JC700 antibody.

Example 9

Identification of EPR-1 Complementary Gene

Three overlapping clones were isolated by hybridization screening of a human P1 plasmid genomic library with the EPR-1 cDNA and confirmed by Southern blot. This gene was located to the long arm of chromosome 17, to band 17q25, by fluorescence in situ hybridization (FIG. 1A, B).

A contig of P1 fragments spanning 14796 bp was cloned in pBSKS⁻ and completely sequenced on both strands (FIG. 1C). Three putative splice sites, matching perfectly the consensus sequences for eukaryotic intron-exon boundaries (Padgett, R. A. et al., *Ann Rev Biochem* (1986) 55:1119–1150), were identified at position 2922, 3284, and 5276 (donor), and 3173, 5157, and 11954 (acceptor), thus defining a gene organization in four exons and three introns of 252, 1874, and 6678 bp, respectively (FIG. 1D).

Sequence analysis of the putative coding regions demonstrated a nearly complete identity with the EPR-1 cDNA (Altieri, D. C., *FASEB J* (1995) 9:860–865), except for 5 nucleotide changes and 6 nucleotide insertions. However, the three splice sites were found on the complementary, antisense strand of the EPR-1 coding sequence. Consistent with this unexpected orientation, the EPR-1 complementary gene revealed a 5' GC rich region, comprising nucleotides 2560–2920 and including exon 1 (see below), which fulfilled the base composition criteria of a CpG island (Gardiner-Garde, M. et al., *J Mol Biol* (1987) 196:261–282 and Frommer, 1987). Sequencing the 2.5 kb upstream the CpG island revealed a TATA-less promoter with numerous Sp1 sites (not shown).

Complex hybridization pattern and evolutionary conservation of EPR-1 sequences. Probing human genomic DNA with the EPR-1 cDNA revealed several hybridizing fragments (FIG. 2A). Of these, a ~7.5 kb XbaI, a 7.6 kb BamHI, and 4 HindIII fragments of ~15, 7.5, 6.4, and 3.7 kb, respectively (FIG. 2A, arrows), could not be recapitulated by the restriction map of the antisense EPR-1 gene (FIG. 1C). In contrast, other bands of comparable intensity, including a 5.15 kb XbaI and a 7.1 kb BamHI fragment, genuinely originated from the antisense EPR-1 gene and comprised the first two, or three exons, respectively (FIG. 2A).

Figure 2B:
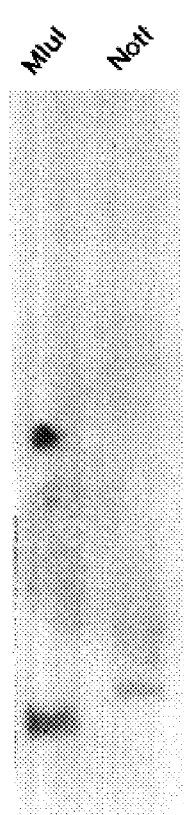
Figure 2C:
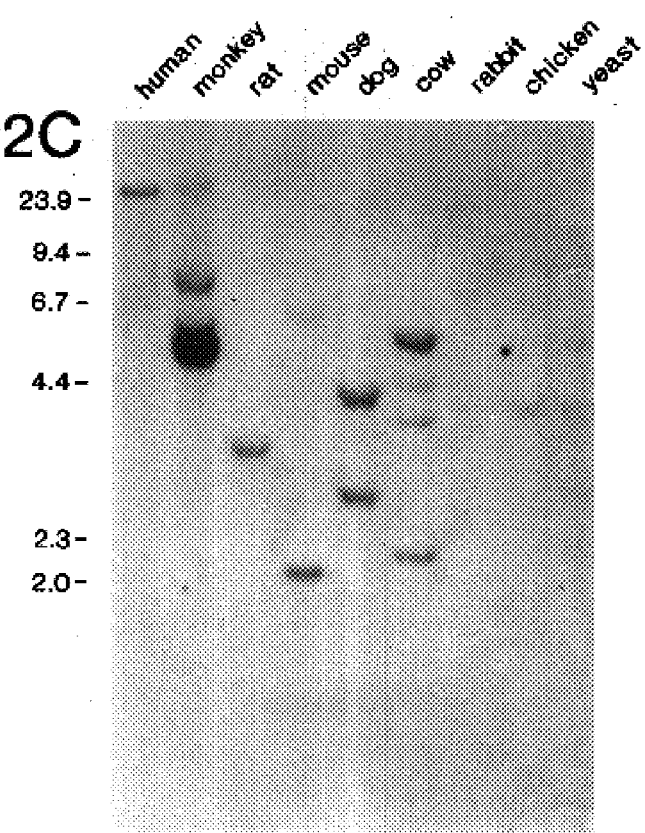

At variance with this complex hybridization pattern, Southern blot of high molecular weight human genomic DNA digested with MluI or NotI and separated by pulsed field gel electrophoresis, revealed single EPR-1-hybridizing bands of ~75 kb and 130 kb, respectively (FIG. 2B). Finally, Southern blots of multiple species genomic DNA revealed significant evolutionary conservation of EPR-1-related sequences (FIG. 2C), with numerous strongly hybridizing bands in mammalian species and fainter signals in rabbit or chicken genomic DNA, under high stringency hybridization conditions (FIG. 2C).

Figure 3A:
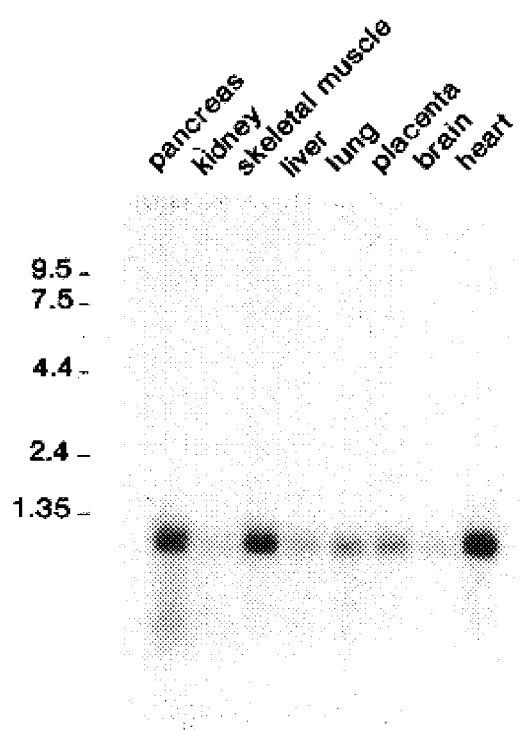
FIGS. 3A–F show the discordant tissue distribution of sense/antisense EPR-1 transcripts. Northern hybridization was carried out on a multiple tissue adult (A–C) or fetal (D–F) mRNA blot with single strand-specific probes in 5×SSPE, 10× Denhardt's solution, 2% SDS, 100 mg/ml denatured salmon sperm DNA at 60° C. for 14 h. After washes in 2×SSC at 60° C. and in 0.2×SSC at 22° C., radioactive bands were visualized by autoradiography. A and B. EPR-1-specific single-strand probe. D and E. Antisense EPR-1-specific single-strand probe. C and F. Control actin probe. Molecular weight markers in kb are shown on the left.
Figure 3B:
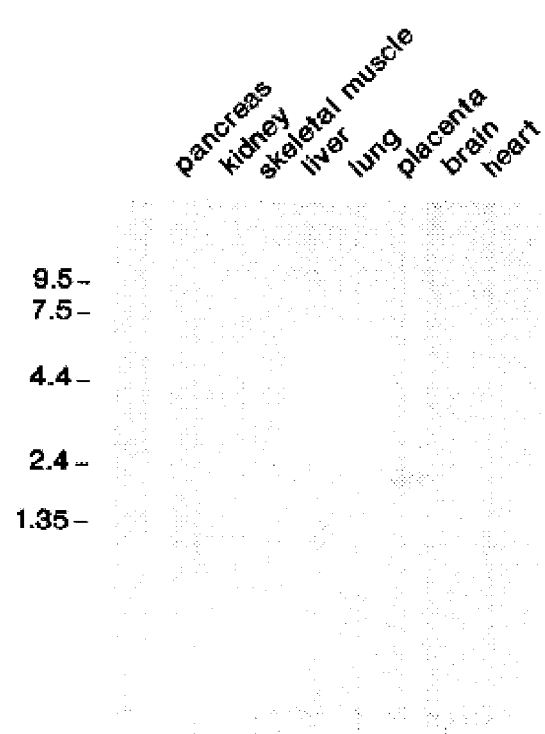
Figure 3C:
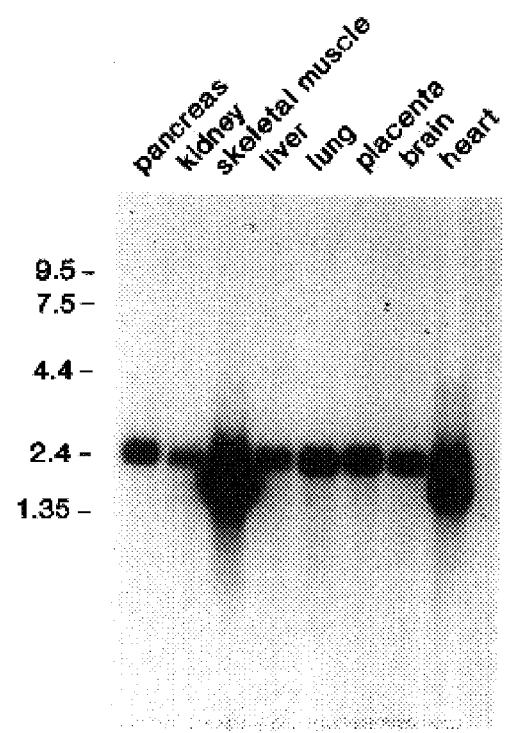
Figure 3D:
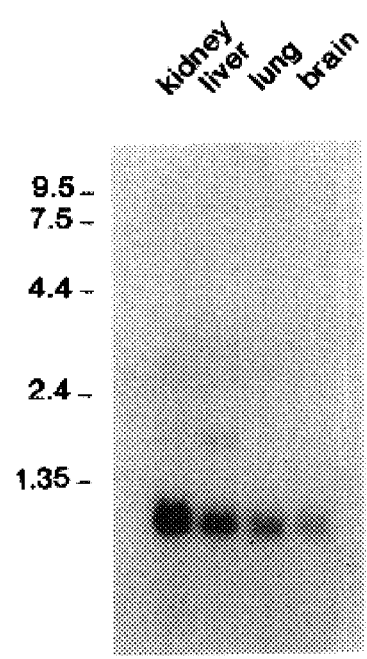
Figure 3E:
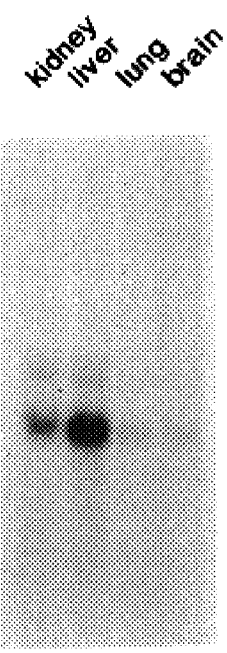
Figure 3F:
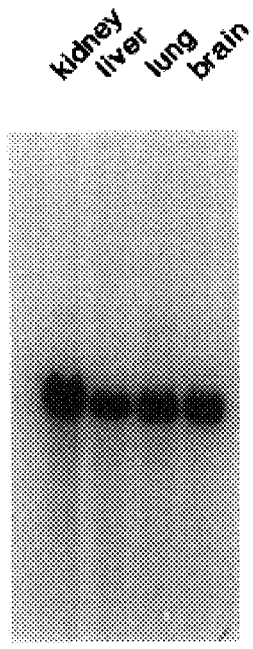

Discordant tissue distribution of sense/antisense EPR-1 transcripts. The potential expression of distinct sense or antisense EPR-1 transcripts was investigated in Northern blots with single strand-specific probes. Consistent with the size of the spliced EPR-1 message (Altieri, D. C., *FASEB J* (1995) 9:860–865), an EPR-1 strand-specific probe detected a prominent ~1.2 kb band in mRNA extracted from all adult and terminally-differentiated human tissues examined (FIG. 3A). In contrast, no specific bands hybridized with a EPR-1 antisense-specific single strand probe in adult tissues, under the same experimental conditions (FIG. 3B). A similar ~1.2 kb band was detected by the single strand EPR-1-specific probe in fetal kidney, and, to a lesser extent, in fetal liver, lung and brain (FIG. 3A). At variance with the absence of hybridization in adult tissues, the EPR-1 antisense-specific probe recognized a prominent ~1.9 kb band, and a larger 3.2 kb species corresponding to the size of an incompletely processed transcript, in fetal liver, while fainter hybridization bands were also seen in fetal kidney, lung and brain (FIG. 3B). A control hybridization with an actin probe confirmed comparable loading of mRNA in adult or fetal samples (FIG. 3C).

Characterization of the antisense EPR-1 gene product. Inspection of the 5' CpG island in the antisense EPR-1 gene revealed a putative ATG initiation codon at position 2811, surrounded by a sequence (CGGCATGG) that conformed well to the consensus for eukaryotic initiation of translation (Kozak, M., *Nucleic Acids Res* (1984) 12:857–872). Analysis of the antisense EPR-1 sequence in the 5'→3' direction dictated by the position of intron-exon boundaries revealed an open reading frame of 426 bp, spanning all four exons, and terminating with a TGA codon at position 12042 in exon 4. A canonical polyadenylation signal (AATAAA) was found at position 13166. PCR products amplified from reverse-transcribed HeLa cell RNA primed with EPR-1 "sense" oligonucleotides matched perfectly the genomic sequence and confirmed the open reading frame and the predicted intron-exon boundaries (not shown).

Two λgt11 cDNA clones isolated by hybridization of a HEL library with the EPR-1 cDNA, also matched the consensus genomic sequence and revealed a homopolymeric A tail on the antisense EPR-1 strand at position 13186, 14 bp downstream the polyadenylation signal, generating a 3' untranslated region of 1144 bp. In these clones, the 5' untranslated region upstream from the initiating ATG was of 49 bp, beginning at position 2762 in the genomic sequence, and contained an in-frame termination codon. Translation of the antisense EPR-1 open reading frame predicted a new protein of 142 amino acids, with an estimated molecular weight of 16,389 and an acidic pI of 5.74, lacking an amino-terminus signal peptide or a carboxy terminus hydrophobic stretch for membrane insertion (FIG. 4A).

A coiled coil was predicted for the last 40 carboxy terminus residues (Lupas, A. et al., *Science* (1991) 252:1162–1164). BLAST database searches revealed a significant degree of similarity between residues 18–88 of the antisense EPR-1 gene product and the BIR module in the IAP family of inhibitors of apoptosis (Birnbaum, M. J. et al., *J Virology* (1994) 68:2521–2528; Clem, R. J. et al., *Mol Cell Biol* (1994) 14:5212–5222). For this analogy, the antisense EPR-1 gene product was designated Survivin. At variance with other IAP proteins, Survivin contained only one BIR, encoded by the first thee exons of the gene, and lacked a carboxy terminus RING finger, without additional/alternative exon(s) potentially encoding this domain (FIG. 1C).

An alignment by the Clustal method between the Survivin BIR and that of other known IAP proteins is shown in FIG. 4B. Despite the overall match of the consensus and several conservative substitutions, phylogenetic analysis suggested that Survivin is a distantly related member of the IAP family, most closely related to NAIP, which also lacked a RING finger (FIG. 4B, shaded boxes) (Roy, N. et al., *Cell* (1995) 80:167–178).

A rabbit polyclonal antiserum designated JC700, was raised against residues A$^3$PTLPPAWQPFLKDHRI$^{19}$ SEQ ID NO: 3, oF Survivin, purified by affinity chromatography on a peptide-Sepharose column, and used in Western blots. Consistent with the predicted molecular weight of Survivin, JC700 antibody immunoblotted a single band of ~16.5 kDa from detergent-solubilized extracts of all transformed cell lines examined, including B lymphoma Daudi and JY, T leukemia Jurkat and MOLT13, monocytic THP-1, and erytholeukemia HEL (FIG. 4C).

Survivin was also found in isolated peripheral blood mononuclear cells (PBMC). In contrast, no expression of Survivin was detected in non-transformed Lu-18 human lung fibroblasts or human umbilical vein endothelial cells (HUVEC) (FIG. 4C). No specific bands were immunoblotted by control non-immune rabbit IgG, under the same experimental conditions (FIG. 4C).

Identification of agents that modulate transcription of the EPR-1 gene. Agents that increase the transcription of the EPR-1 gene may be identified by conventional techniques. Preferably, a candidate agent is brought into contact with a cell that expresses the EPR-1 gene product and the level of expression of this product or the level of transcription are determined and agents that increase or decrease EPR-1 gene transcripts may readily be identified. Alternatively, the EPR-1 transcriptional regulatory elements may be placed upstream of a reporter gene such as CAT or β-galactosidase.

Example 10

Regulation of Survivin Expression by Cell Growth/Differentiation

Consistent with the expression of Survivin in transformed cell lines (FIG. 4C), undifferentiated and actively proliferating promyelocytic HL-60 cells constitutively expressed high levels of Survivin, as demonstrated by immunoblotting of a single ~16.5 kDa band with JC700 antibody, and Northern hybridization of a ~1.9 kb transcript with a single strand-specific probe (FIG. 5). In contrast, no specific bands were recognized by control non-immune rabbit IgG under the same experimental conditions (FIG. 5).

Vitamin $D_3$-induced terminal differentiation of HL-60 cells to a mature monocytic phenotype resulted in growth arrest of these cells and de novo induction of differentiation-specific markers, including a ~200-fold increased expression of leukocyte CD11b/CD18 integrin detected by flow cytometry (not shown), and in agreement with previous observations (Hickstein, D. D. et al., *J Immunol* (1987) 138:513–519). Under these experimental conditions, the anti-Survivin JC700 antibody failed to immunoblot specific bands from vitamin $D_3$-treated HL-60 extracts, and no Survivin transcript(s) were detected by Northern hybridization with a single strand-specific probe (FIG. 5).

In contrast, an anti-EPR-1 polyclonal antibody immunoblotted a single ~62 kDa band corresponding to EPR-1 in vitamin $D_3$-differentiated HL-60 extracts under the same experimental conditions (not shown). Moreover, downregulation of Survivin in vitamin $D_3$-differentiated HL-60 cells was accompanied by a 5- to 10-fold increased surface expression of EPR-1 in these cells, as detected by flow cytometry with anti-EPR-1 monoclonal antibodies B6 or 12H1 (FIG. 8).

As shown in FIG. 16, Survivin is down regulated by the combination of cytokines γ interferon and tumor necrosis factor α, but not by either cytokine alone. Similarly, the transfection of 3T3 cells with the c-myc oncogene results in the up-regulation of Survivin mRNA as detected by Northern blots.

Example 11

Promoting Apoptosis with Survivin

Targeting Survivin promotes apoptosis and inhibits cell proliferation

Transfection of the Survivin cDNA in mouse or hamster cell lines (NIH 3T3, CHO) was not suitable for the presence of immunochemically indistinguishable endogenous homologues in these cells (not shown). Similarly, initial attempts to target the Survivin gene in stable antisense transfectants were unsuccessful for slow cell growth and rapid loss of viability (not shown). Therefore, Survivin+ HeLa cells were transfected with the 3' end of the EPR-1 cDNA (Survivin antisense) under the control of a metallothionein-inducible promoter (Lukashev, M. E. et al., *J Biol Chem* (1994) 269:18311–18314), selected in hygromycin, and analyzed for apoptosis and cell proliferation after $Zn^{2+}$-dependent activation of transcription.

Consistent with the expression of Survivin in transformed cell lines (FIG. 4C), the JC700 antibody immunoblotted a single molecular species of ~16.5 kDa in extracts of control HeLa cells transfected with the vector alone (FIG. 7A). In contrast, no specific bands were recognized by JC700 antibody in metallothionein-induced HeLa cells transfected with the EPR-1 cDNA (Survivin antisense) (FIG. 7A). Under these experimental conditions, in situ analysis of internucleosomal DNA fragmentation by AptoTag staining revealed only a few apoptotic cells in serun-starved, $Zn^{2+}$-induced, vector control HeLa cells (FIG. 7B).

In contrast, as discussed above, inhibition of Survivin expression in $Zn^{2+}$-induced antisense HeLa cell transfectants was associated with prominent nuclear staining in the vast majority of cells examined (FIG. 7B). No nuclear staining was detected in the absence of TdT tagging of the digoxigenin-labeled dUTP (not shown). Typical morphologic features of apoptosis, including numerous apoptotic bodies, were also demonstrated in induced antisense HeLa cell transfectants by hematoxylin/eosin staining, while only occasional apoptotic bodies were observed in vector control HeLa cultures, under the same experimental conditions (FIG. 7B).

A potential effect of Survivin on cell growth was also investigated. In these experiments, metallothionein-controlled, EPR-1-dependent, inhibition of Survivin expression caused a profound reduction of serum-dependent HeLA cell proliferation (FIG. 7C). Three days after $Zn^{2+}$ induction, the cell count in vector control HeLa cultures increased by 288%, as opposed to only a 20% increase in Survivin antisense transfectants, under the same experimental conditions (FIG. 7C).

Example 12

Structure-Function Relationship of Survivin

The minimal structural requirements involved in Survivin-mediated inhibition of apoptosis have been identified through a mutagenesis strategy of Ala substitutions of the most evolutionarily conserved residues in the single Survivin BIR (baculovirus IAP repeat) module. These residues included in the amino-terminal half of the Survivin BIR, $Arg^{18}$, $Phe^{22}$, $Trp^{25}$, $Pro^{26}$, $Pro^{35}$, $Ala^{39}$, $Ala^{41}$, $Gly^{42}$, and $Cys^{46}$. In the carboxyl-terminal half of the Survivin BIR, Ala mutants were first targeted at the $Cys^{57}X_2Cys^{60}X_{16}His^{77}X_6Cys^{844}$ putative zinc binding motif. Additional conserved residues targeted by mutagenesis include $Asp^{53}$, $Leu^{64}$, $Trp^{67}$, $Pro^{69}$, $Asp^{71}$, $Asp^{72}$ and $Pro^{73}$.

The Survivin mutants are characterized in stable and transiently transfected cells, IL-3-dependent BaF3 cells and NIH3T3, respectively. In addition to these point mutants, a Survivin chimeric molecule containing a carboxyl-terminal RING finger has also been generated and screened for apoptosis inhibition (the RING finger is a domain found in most other IAP proteins, but not in Survivin). Secondly, a truncated form of Survivin has also been generated, in which the last 40 carboxylterminus residues, containing a predicted coiled-coil structure, have been deleted. As shown in FIG. 12, Ala mutagenesis of key conserved residues in Survivin $Trp^{67}$-$Pro^{73}$-$Cys^{84}$ produced a recombinant molecule which lacked the ability to protect BaF3 cells from apoptosis induced by IL-3 withdrawal.

Example 13

Cytoprotective Effects of Survivin

Classical examples of cell damage to stable cell populations mediated by apoptosis include allograft rejection by infiltrating lymphocytes, Alzheimer's disease and reperfusion injury following myocardial infarction. In addition to being expressed in cancer, thereby functioning as a growth-advantage factor for cancer cells, the targeted expression of Survivin is useful to protect stable cell populations from apoptosis and other cellular insults. This application of Survivin was tested by adding increasing concentrations of purified recombinant Survivin to monolayers of human endothelial cells injured with hydrogen peroxide ($H_2O_2$), a classical apoptosis-inducing stimulus. The results are summarized in FIG. 13. Increasing concentrations of added Survivin resulted in a significant increased viability of the treated cells as opposed to control cultures treated with control protein myoglobin. Similarly, Survivin protected NIH3T3 cells from apoptosis induced by hydrogen peroxide after transient co-transfection with a lacZ reporter gene as shown in FIG. 17.

Example 14

Survivin as a Predictive-Prognostic Factor

The presence of Survivin can be utilized as predictive-prognostic negative factor in neuroblastoma and non-Hodgkin's lymphoma, and in other cancers.

Neuroblastoma. A large series of neuroblastoma cases (72) was screened for Survivin expression in a multicentric study. As shown in FIG. 14, Survivin expression increased dramatically when patients contained at least one negative prognostic factor for aggressive and rapidly progressing disease. Secondly, expression of Survivin strongly correlated with a more aggressive disease and unfavorable histology. Importantly, expression of Survivin was a more sensitive prognostic index than simple histology. Survivin-positive cases with early diagnosis of favorable histology were found to contain at least one negative prognostic factor for disease progression and dissemination.

Hodgkin's Lymphoma. A similar multicentric study has been recently completed on analysis of Survivin expression in high grade non-Hodgkin's lymphoma (n=48). The results are similar to those observed for neuroblastoma. As shown in FIG. 15, expression of Survivin strongly correlated with a more widespread disease predominantly in stage IV. Clinically, Survivin-expressing patients had fewer episodes of complete remission and more episodes of incomplete remission, no remission or relapses as compared with Survivin-negative patients.

Potential implications. The demonstrated role of Survivin as a negative predictive prognostic factor in these two embryologically different types of cancer iterates the potential use of this molecules a diagnostic tool to monitor disease progression and response to the therapy. It can also be used for staging purposes and to identify populations of patients potentially susceptible to multi-drug resistance (groups with no remissions or incomplete remissions). Also, Survivin derived primers easily designed from the complete sequence of the Survivin gene can be used as a screening tool to identify potential cases of cancer in which the Survivin gene has been deleted or mutated. These cases will be very important to identify because targeted inactivation of the Survivin gene would confer a favorable prognostic factor to cancer patients, removing a potential drug-resistance gene. Inactivating mutations in the Survivin gene can target the same key residues identified in our initial screening of Ala-based mutagenesis or result in an abortive or truncated protein for premature termination of translation.

Example 15

Survivin Cancer Vaccine

Vaccines directed against Survivin, as found in various types of cancer, may be developed as with other disease-related intracellular protein targets. These techniques are commonly available and representative approaches are described by the references cited below. Vaccines may also include the systemic administration of peptide fragments of Survivin and the use of vectors to deliver mini-genes encoding Survivin peptides to tumor cell targets are contemplated. As mentioned above, Survivin is not expressed in normal cells, even in proliferating stem cells in the bone marrow. This ensures that the immune response mounted against Survivin will be highly selective and specific and will not involve normal cells.

Development and Administration of Polypeptide-Based Vaccines

Methods of the use of peptide components in a monovalent or a polyvalent cancer immunotherapy-vaccine product are described by Nardi, N. et al., *Mol. Med.* (1995) 1(5) :563–567. Additional references that discuss the different cancer vaccine and cancer immunotherapies currently being used include: N. P. Restifo and M. Sznol "Cancer Vaccines," in DeVita's Cancer: Principles & Practice of Oncology 3023–3043 (Lippincott-Raven, Philadelphia; 1997); J. Galea-Lauri et al., *Cancer Gene Ther*. (1996) 3(3): 202–214; D. C. Linehan et al., *Ann. Surg. Oncol.* (1996) 3(2): 219–228; and J. Vieweg et al., *Cancer Invest.* (1995) 13(2): 193–201.

Consistent with the foregoing approach, Survivin polypeptides or full length Survivin are synthesized either chemically by known techniques or recombinantly by expressing appropriate cDNAs in prokaryotic or eukaryotic cells. Survivin proteins so produced are then purified as necessary to remove contaminating proteins, such as serum or bacterial proteins. Survivin can be further purified using columns containing antibodies that bind Survivin, such as the monoclonal antibody JC700 or the antibody 8E2 (both described above) which recognize and bind to Survivin. In purifying an antibody-based vaccine, the recombinantly produced Survivin would bind to the antibodies while other proteins and cellular debris would be washed out. Survivin polypeptides are then be isolated and concentrated to a desired strength.

Alternatively Survivin polypeptides are created by cleaving the native Survivin with one or more proteases (e.g., trypsin). Proteolytic fragments are then be separated and recovered using SDS-PAGE, high-resolution/high-pressure separation techniques, or reverse-phase HPLC. See R. J. BEYNON AND J. S. BOND, PROTEOLYTIC ENZYMES: A PRACTICAL APPROACH (Oxford University Press, New York 1989). These isolated peptides are then be concentrated to a desired final concentration.

Once purified, Survivin polypeptides or full length Survivin molecules may then placed in an emulsion containing an adjuvant. Adjuvants contemplated for use with Survivin include aluminum adjuvants, Freund's adjuvant, oil-in-water emulsions containing tubercle bacilli, and interleukin-2 (IL-2). Additional preparations include combining the Survivin polypeptides with other appropriate tumor-associated antigens and, optionally, other immunomodulatory agents such as cytokines. Other suitable carriers or excipients can be used including bovine serum albumin, coupling the Survivin polypeptide with haptens, keyhole limpet hemocyanin, ovalbumin, and purified protein derivative of tuberculin. Peptides may be coupled to carriers using techniques such as those described in ED HARLOW AND DAVID LANE, ANTIBODIES: A LABORATORY MANUAL (Cold Spring Harbor Laboratory, 1988).

Vaccines in human subjects may be administered in the form of an emulsion injected subcutaneously, intradermally or intramuscularly (IM); vaccines appropriately formulated can be taken orally. With vaccines containing adjuvants, the vaccine is generally preferably be given IM, e.g., in the deltoid.

The amount of Survivin vaccine or Survivin peptide vaccine to be administered to a patient will correspond to values typically used in for other cancer vaccines. Dosage concentrations will range from about 0.25 g to about 1000 g per day. More preferred ranges will be from about 10 $\mu$g to about 500 $\mu$g per day.

Example 16

Diagnostic Use of Anti-Survivin Antibodies

Frequently, tumor associated antigens (TAA) are shed from tumor cells into the surrounding plasma or into the blood. As a result, TAA often are found in the blood, and blood samples obtained from patients may be used in detecting the presence of cancer, as well as used as a factor is staging cancers (e.g. stage I, II, III or IV). Survivin is one such TAA, and healthy, normal individuals do not express Survivin. Results from studies of several cancers have indicated that the presence of Survivin (or Survivin fragments) correlates with and is predictive that the disease may be aggressive or may have metastasized. A similar strategy of detecting and quantifying the levels of Survivin or Survivin fragments can be used to determine residual tumor burden in patients undergoing chemotherapy or radiation therapy for cancer treatment. Elevated or increasing levels of Survivin may reflect late stage neoplastic disease.

For diagnostic uses, blood is drawn from patients, by well known techniques, who have known cancer loads or from patients suspected of having cancer. The blood sample is prepared by known techniques and is tested for binding with antibodies to Survivin that are prepared and, optionally, labeled, as discussed above. Such general antibody detection protocols and associated reagents are well established in the art. Other biological fluid samples such as semen, urine, or saliva can also be monitored for the presence of Survivin. This diagnostic technique also can be used to monitor disease progression and response to individualized therapies. This method offers a relatively non-invasive means of tracking cancer progression or regression.

Example 17

Detection of Survivin by Immunobioassay

An illustrative example of an immunobioassay to test for the presence of Survivin in the blood of patient relies on the ability of the monoclonal antibodies to Survivin to bind Survivin and remove the detectable Survivin from solution by immunoprecipitation. Such an immunobioassay is used to detect Survivin in suspected cancer patients and in fractions eluted from fractionation columns. An aliquot of each patient sample is incubated for 2 hours at 4° C. with a monoclonal antibody that specifically recognizes and binds Survivin, such as the Mab 8E2, described above. The monoclonal antibody is insolubilized on anti-mouse IgG agarose beads, which can be acquired from Sigma Chemical Co., St. Louis, Mo.

The agarose bead anti-mouse (IgG(H+L))-Survivin complex is prepared by first washing the agarose beads with binding buffer containing 0.01 M phosphate buffer, (pH 7.2), and 0.25 M NaCl and then incubating the beads with the Survivin monoclonal antibody for 18 hours at 4° C. in the same buffer. The agarose beads may then be sedimented by centrifugation for 30 seconds at 16,000×g in a microcentrifuge and non-specific sites may be blocked by incubation with 2% non-fat dry milk in 0.5 M NaCl-TMK for 30 minutes at 4° C. After blocking, the beads may be washed 3 times with 0.5 M NaCl-TMK and resuspended in an equal volume of the same buffer. 20:1 of the agarose bead-monoclonal antibody complex may then incubated with each 250:1 of the patient test sample for 2 hours at 4° C. Any Survivin present in the patient test sample will be found by the Survivin monoclonal antibody on the beads. The bead complex, now with Survivin bound, may be removed by centrifugation for 30 seconds at 16,000×g. The supernatant is then assayed for Survivin activity in the bioassay as described below. Control samples are treated with blocked beads that lacked the Survivin monoclonal antibody and tested for Survivin activity in the bioassay.

Example 18

Detecting Survivin Using a Direct ELISA Test

Samples of normal plasma (control) and cancer patient-plasma are diluted 1:1 with phosphate buffered saline (PBS). One volume of each mixture is added to centricon-10 filter having a 10 kD molecular weight limit and centrifuged at 5000×g (7000 rpm) for 1 hour. One volume of PBS is added to the retentate and centrifuged for 30 min. The final dilution is about 1:3. The ELISA plate wells are then coated with retentate at 1:6, 1:12, 1:24, 1:48 and 1:96 final dilution in bicarbonate coating buffer, having a pH 9.6 overnight at 4° C. C. The plates are then washed 2 times with wash buffer containing 5% Tween 20 in phosphate buffered saline. Residual binding sites are blocked with 4% bovine serum albumin (BSA), 300 $\mu$l/well for 2 hours. Plates are then washed 2 times with wash buffer. Next, 100 $\mu$l of a monoclonal antibody that specifically recognizes and binds to Survivin, such as Mab 8E2, is used at 1:200 dilution in 1% BSA is added to the wells and incubated for 1 hour with agitation. Plates are washed 5 times with wash buffer. Next, 100 $\mu$l horseradish peroxidase conjugated secondary antibody is added, typically at a 1:2,000 dilution to each well, and incubated for 1 hour. Plates are again washed 5 times with wash buffer. Next, 100 $\mu$l/well of substrate containing 5 $\mu$g of Survivin and 5 $\mu$l $H_2O_2$/10 ml citrate-phosphate buffer is added to each well and incubated for 5 minutes. The enzyme reaction is stopped by adding 50 $\mu$l/well 2 M $H_2SO_4$. The absorbance of light is measured at 492 nm in an EIA reader. Patient samples that contain Survivin will produce a positive reading, whereas those samples that do not contain Survivin will be negative.

Example 19

Survivin Fragmnets, Peptides and Small Molecule Antagonists

As described above, key functional residues in Survivin required for apoptosis have been identified. These data provide a template upon which to produce synthetic peptides and small molecule antagonists and competitive inhibitors of Survivin function. Preferably, the peptides are produced from native Survivin or include substitutions from the native Survivin peptide backbone that include the functionally relevant residues $Trp^{67}$-$Pro^{73}$-$Cys^{84}$. Peptide fragments of native Survivin can be generated by standard techniques, including protein digests. A determination of which fragments compete with Survivin can readily be made by using the apoptosis measurement systems and apoptosis assay systems described above. These results provide a unique opportunity to identify a discrete linear sequence in Survivin, that is essential for inhibition of apoptosis.

Consistent with the general paradigm of IAP proteins-dependent inhibition of apoptosis, it also was predicted that a structural region in the molecule required for the anti-apoptotic function is the primary candidate for being a site of interaction with other molecules (such as binding partners). The fimctionally relevant peptide sequence in Survivin, based on the mutagenesis data, is: EG<u>W</u>EPDDD PIEEHKKHSSG<u>C</u> (SEQ ID NO: 4), Ala substitutions of the underlined residues results in a complete loss of function of Survivin in transfected cells. This linear sequence can be synthesized and used as a much more stringent and specific reagent to isolate associated molecules using standard biochemical procedures of affinity chromatography or as a bait for the yeast two-hybrid system.

Also, preferably, the βCOOH coiled-coil region of Survivin is included in Survivin fragments and peptides. Recent data indicates that this Survivin domain is important for the anti-apoptosis function of Survivin. We have generated a recombinant truncated form of Survivin lacking the last 40 βCOOH terninus amino acids comprising the coiled-coil domain. This truncated form was co-transfected with a lacZ plasmid in NIH3T3 cells sideby-side with wild type Survivin and XIAP, another member of the IAP gene family. The results, shown in FIG. 17, indicate that the truncated Survivin had lost most (~80%) of the cytoprotective effect at preventing apoptosis in transfected cells induced by hydrogen peroxide. Incidentally, in this system, Survivin was more potent than NAIP at preventing apoptosis.

Agonists and antagonists of Survivin also can readily be identified through conventional techniques. Designed, synthetic peptides based on the native linear sequence also function as competitive inhibitors of Survivin's interaction with as yet unidentified partner molecules. However, this inhibition should be sufficient to block the anti-apoptosis function of Survivin.

A similar peptide-based strategy has been successful to block caspase activation in vitro and in vivo, protecting cells from apoptosis. See, e.g., Milligan, C. E. et al., (1995) *Neuron* 15:385–393.

Example 20

Therapeutic Uses of Antisense Survivin DNA

As described above, the transcription of a Survivin antisense sequence altered the EPR-1/Survivin gene balance. This was demonstrated in HeLa cell transfectants, in which metallothionein-induced transcription of the EPR-1 "sense" strand suppressed the expression of Survivin and profoundly influenced apoptosis/cell proliferation. Additionally, transiently co-transfecting a Survivin antisense construct with a LacZ reported plasmid decreased the viability of Survivin antisense transfectants after a 48 h transfection in β-galactosidase expressing cells. Accordingly, the level of expression of Survivin in a Survivin expressing cell or tissue, such as a tumor, is decreased by transfecting the cell or tissue with the EPR-1 sense stand of DNA. Alternatively, a Survivin antisense-encoding DNA is used to transfect a target cell or tissue. Such therapy effectively decreases the translation of Survivin-encoding mRNA into Survivin protein.

Example 21

Use of Survivin as a Protective Agent Against Apoptosis

Survivin has been shown to protect cells from apoptosis when administered to cells that have been exposed to hydrogen peroxide or other agents that typically induce apoptosis. It is contemplated that cellular permeability may need to be increased, preferably in a transient manner in order to facilitate delivery of Survivin, or fragments thereof effective to reduce apoptosis. Certain conditions involving transient metabolic inhibition or transient hypoxia are likely to increase cellular permeability without the need for additional, external agents. Agents that may be appropriate include, metabolic inhibitors like 2-deoxygluocose and sodium azide. However, the ability of Survivin to mediate cytoprotection during a transient increase in cellular permeability offers the possibility of using therapeutic infusion of recombinant Survivin to decrease reperfusion injury and cellular damage during myocardial infarction and stroke. It is contemplated that such processes are mediated by increased tissue damage due to apoptosis. Treatment with Survivin could reduce the extent and magnitude of the injured tissue.

The use of Survivin or allelic variants of Survivin in subjects to modulate or prevent apoptosis related cell death would be beneficial in treating or ameliorating the effects of a variety of apoptosis-related indications. These indications include, but are not limited to, dermatological effects of aging (e.g., baldness that is caused by apoptosis of cells of hair follicle cells), disorder and diseases such as immunosuppression, gastrointestinal perturbations (e.g., damage of lining of the gut, ulcers, and radiation or chemotherapy induced damage), cardiovascular disorders, apoptosis related to reperfusion damage (e.g., coronary artery obstruction, cerebral infarction, spinal/head trauma and concomitant severe paralysis, damage due to insults such as frostbite or burns, and any indication previously thought to be treatable by superoxide dismutase), rejection of tissue transplantation (e.g., graft versus host disease), and Alzheimer's disease. The administration of Survivin also may be cytoprotective against chemotherapy or radiation-induced apoptosis.

Survivin protein for administration can be produced as described above, e.g., using the cDNA described herein. The protein may require purification for purposes of pharmaceutical administration and such purification steps preferably utilize monoclonal antibody separation and purification techniques as also described above.

In a clinical setting, Survivin is administered to patients in pharmaceutically effective dosages, i.e., in dosages effective to reduce the level or extent of apoptosis otherwise present, via several routes. For example, to treat dermatological ailments that involve apoptosis, Survivin can be administered in a salve, cream, ointment or powder form. Topical formulations may contain additional pharmaceutical or cosmetic compositions such as moisturizers, humectants, odor modifiers, buffer, pigment, preservatives, vitamins (such as A, C or E), emulsifiers, dispersing agents, wetting agents, stabilizers, propellants, antimicrobial agents, sunscreen, enzymes and the like. Typical dosages of Survivin that may be administered to patients will be 0.01% to 1.0% by weight. Additional topical pharmaceutical compositions are described in S. Nakai et al., U.S. Pat. No. 5,672,603.

Survivin may also be administered, as may be appropriate for the condition being treated, in the form of pills, solutions, suspensions, emulsions, granules or capsules. Survivin can be administered orally; injected in solutions administered intravenously either alone or in admixture with conventional fluids for parenteral infusion (e.g., fluids containing glucose, amino acids etc.); injected intramuscularly, intradermally, subcutaneously or intraperitoneally; using suppositories; and in the form of ophthalmic solutions such as eye drops. Survivin can also be administered using delayed release carriers, such as liposomes, microsponges, microspheres or microcapsules that are deposited in close proximity to the tissue being treated for prevention of apoptosis related cell death.

Concentrations of Survivin or functional allelic variants of Survivin administered via routes other than topical administration typically would range in dose from about 10 µg per day to about 25 mg per day depending on the route of administration. Of course, it would be expected that skilled artisans, such as physicians, may alter these values on a case by case basis as required for the particular patient.

What is claimed:

1. An isolated polypeptide comprising the amino acid sequence as set forth in SEQ ID NO: 34.

2. An isolated polypeptide encoded by a nucleic acid molecule, wherein the polypeptide inhibits cellular apoptosis and wherein the nucleic acid molecule hybridizes to the full length complement of an open reading frame (ORF) of a nucleic acid molecule, said ORF consisting of nucleotides 2811–2921, 3174–3283, 5158–5275 and 11955–12041 of SEQ ID NO: 35, which encodes SEQ ID NO: 34, under conditions comprising washing with 0.015 M NaCl, 0.0015 M sodium citrate, 0.1% NaDodSO$_4$ at 50° C.

3. An isolated polypeptide that inhibits cellular apoptosis, wherein said polypeptide is encoded by a nucleic acid molecule that hybridizes to a nucleic acid encoding SEQ ID NO: 34, under conditions comprising washing with 0.015 M NaCl, 0.0015 M sodium citrate, 0.1% NaDodSO$_4$ at 50° C.

4. An isolated polypeptide of claim 2 or 3, wherein hybridization conditions further comprises hybridizing in 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.

5. An isolated polypeptide encoded by a nucleic acid molecule, wherein the polypeptide inhibits cellular apoptosis and wherein the nucleic acid molecule hybridizes to the full length complement of an open reading frame (ORF) of a nucleic acid molecule, said ORF consisting of nucleotides 2811–2921, 3174–3283, 5158–5275 and 11955–12041 of SEQ ID NO: 35, which encodes SEQ ID NO: 34, under conditions comprising hybridizing in 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC and 0.1% SDS.

6. The isolated polypeptide of claim 2, 3, or 5, wherein the polypeptide is a mammalian polypeptide.

7. The isolated polypeptide of claim 6, wherein the mammalian polypeptide is a human polypeptide.

8. A polypeptide of claim 2, 3, or 5, wherein the polypeptide has a molecular weight of 16.5 KDa as determined by SDS PAGE.

9. A polypeptide of claim 8, wherein the polypeptide is a mammalian polypeptide.

10. A polypeptide of claim 9, wherein the polypeptide is a human polypeptide.

11. A polypeptide of claim 10, wherein the polypeptide consists essentially of the amino acid sequence as set forth in SEQ ID NO: 34.

12. A polypeptide of claim 10, wherein the polypeptide consists of the amino acid sequence as set forth in SEQ ID NO: 34.

13. A polypeptide consisting of at least 10 contiguous amino acids of SEQ ID NO:34.

14. A polypeptide consisting of at least 15 contiguous amino acids of SEQ ID NO:34.

15. A polypeptide consisting of at least 17 contiguous amino acids of SEQ ID NO:34.

16. A polypeptide of claim 2, 3, or 5, wherein the polypeptide comprises a βCOOH coiled-coil region.

17. A polypeptide of claim 2, 3, or 5, wherein the polypeptide comprises a BIR domain.

18. A polypeptide of claim 2, 3, or 5, wherein the polypeptide further comprises a heterologous amino acid sequence.

19. A polypeptide of claim 2, 3, or 5 comprising SEQ ID NO: 3.

20. A polypeptide of claim 2, 3, or 5 comprising the sequence EGWEPDDDPIEEHKKHSSGC (SEQ ID NO: 4).

21. A fusion protein comprising a polypeptide of any one of claims 1, 2, 3, or 5.

22. A fusion protein of claim 21, wherein the fusion protein comprises a C-terminal RING finger domain.

23. A composition comprising a polypeptide of any one of claims 1, 2, 3, or 5.

24. A pharmaceutical composition comprising a polypeptide of any one of claims 1, 2, 3, or 5, and a carrier.

* * * * *

UNITED STATES PATENT AND TRADEMARK OFFICE
CERTIFICATE OF CORRECTION

PATENT NO. : 6,943,150 B1 Page 1 of 1
APPLICATION NO. : 09/690825
DATED : September 13, 2005
INVENTOR(S) : Dario C. Altieri It is certified that error appears in the above-identified patent and that said Letters Patent is hereby corrected as shown below:

Column 80, line 14, claim 13, please delete "A" and insert therefore "An" and before "polypeptide", please insert --isolated--;

Column 80, line 16, claim 14, please delete "A" and insert therefore "An" and before "polypeptide", please insert --isolated--; and Column 80, line 18, claim 15, please delete "A" and insert therefore "An" and before "polypeptide", please insert --isolated--.

Signed and Sealed this

Eighth Day of July, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,943,150 B1 | Page 1 of 1 |
| APPLICATION NO. | : 09/690825 | |
| DATED | : September 13, 2005 | |
| INVENTOR(S) | : Dario C. Altieri | |

It is certified that error appears in the above-identified patent and that said Letters Patent is hereby corrected as shown below:

In Column 1, line 12, before the section entitled "FIELD OF THE INVENTION", insert the following --GOVERNMENT SUPPORT
This invention was made with government support under HL054131 and HL043773 awarded by National Institute of Health. The government has certain rights in the invention.--

Signed and Sealed this
Twenty-seventh Day of November, 2012

David J. Kappos
*Director of the United States Patent and Trademark Office*

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 1:

TGCTGGCCGC TCCTCCCTC                                                                                    19

(2) INFORMATION FOR SEQ ID NO: 2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 2:

ATGACCTCCA GAGGTTTC                                                                                     18

(2) INFORMATION FOR SEQ ID NO: 3:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

Ala Pro Thr Leu Pro Pro Ala Trp Gln Pro Phe Leu Lys Asp His Arg
1               5                   10                  15

Ile (2) INFORMATION FOR SEQ ID NO: 4:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Glu Gly Trp Glu Pro Asp Asp Pro Ile Glu Glu His Lys Lys His
1               5                   10                  15

Ser Ser Gly Cys
            20

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GCGGGTGAGC TGTCCCTTGC AGATGGC                                                                           27

(2) INFORMATION FOR SEQ ID NO: 6:

(i) SEQUENCE CHARACTERISTICS:
        (A) LENGTH: 27 base pairs
        (B) TYPE: nucleic acid

```
          (C) STRANDEDNESS: single
          (D) TOPOLOGY: linear (ii) MOLECULE TYPE: DNA (genomic)

(xi) SEQUENCE DESCRIPTION: SEQ ID NO: 6:

CCATGTAAGT TGATTTTTCT AGAGAGG                                          27

(2) INFORMATION FOR SEQ ID NO: 7:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 7:

AATTGTATGT CTTTATTTCC AGGCAAA                                          27

(2) INFORMATION FOR SEQ ID NO: 8:

(i) SEQUENCE CHARACTERISTICS:
          (A) LENGTH: 45 amino acids
          (B) TYPE: amino acid
          (C) STRANDEDNESS: <Unknown>
          (D) TOPOLOGY: linear (ii) MOLECULE TYPE: protein (xi) SEQUENCE DESCRIPTION: SEQ ID NO: 8:

Glu Glu Ala Arg Leu Val Thr Phe Gln Asn Trp Pro Asp Ala Phe Leu
1               5                  10                  15

Thr Pro Gln Glu Leu Ala Lys Ala Gly Phe Tyr Tyr Leu Gly Arg Gly
            20                  25                  30

Asp Gln Val Gln Cys Phe Ala Cys Gly Gly Lys Leu Ala
        35                  40                  45

(2) INFORMATION FOR SEQ ID NO: 9:

(i) SEQUENCE CHARACTERISTICS:
          (A) LENGTH: 45 amino acids
          (B) TYPE: amino acid
          (C) STRANDEDNESS: <Unknown>
          (D) TOPOLOGY: linear (ii) MOLECULE TYPE: protein (xi) SEQUENCE DESCRIPTION: SEQ ID NO: 9:

Glu Glu Ala Arg Phe Leu Thr Tyr Ser Met Trp Pro Leu Ser Phe Leu
1               5                  10                  15

Ser Pro Ala Glu Leu Ala Arg Ala Gly Phe Tyr Tyr Ile Gly Pro Gly
            20                  25                  30

Asp Arg Val Ala Cys Phe Ala Cys Gly Gly Lys Leu Ser
        35                  40                  45

(2) INFORMATION FOR SEQ ID NO: 10:

(i) SEQUENCE CHARACTERISTICS:
          (A) LENGTH: 45 amino acids
          (B) TYPE: amino acid
          (C) STRANDEDNESS: <Unknown>
          (D) TOPOLOGY: linear (ii) MOLECULE TYPE: protein
```

(xi) SEQUENCE DESCRIPTION: SEQ ID NO: 10:

Glu Ala Asn Arg Leu Val Thr Phe Lys Asp Trp Pro Asn Pro Asn Ile
1               5                   10                  15

Thr Pro Gln Ala Leu Ala Lys Ala Gly Phe Tyr Tyr Leu Asn Arg Leu
            20                  25                  30

Asp His Val Lys Cys Val Trp Cys Asn Gly Val Ile Ala
        35                  40                  45

(2) INFORMATION FOR SEQ ID NO: 11:

(i) SEQUENCE CHARACTERISTICS:
        (A) LENGTH: 45 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 11:

Glu Glu Val Arg Leu Asn Thr Phe Glu Lys Trp Pro Val Ser Phe Leu
1               5                   10                  15

Ser Pro Glu Thr Met Ala Lys Asn Gly Phe Tyr Tyr Leu Gly Arg Ser
            20                  25                  30

Asp Glu Val Arg Cys Ala Phe Cys Lys Val Glu Ile Met
        35                  40                  45

(2) INFORMATION FOR SEQ ID NO: 12:

(i) SEQUENCE CHARACTERISTICS:
        (A) LENGTH: 45 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 12:

Lys Ala Ala Arg Leu Gly Thr Tyr Thr Asn Trp Pro Val Gln Phe Leu
1               5                   10                  15

Glu Pro Ser Arg Met Ala Ala Ser Gly Phe Tyr Tyr Leu Gly Arg Gly
            20                  25                  30

Asp Glu Val Arg Cys Ala Phe Cys Lys Val Glu Ile Thr
        35                  40                  45

(2) INFORMATION FOR SEQ ID NO: 13:

(i) SEQUENCE CHARACTERISTICS:
        (A) LENGTH: 47 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 13:

Glu Glu Ala Arg Leu Ala Ser Phe Arg Asn Trp Pro Phe Tyr Val Gln
1               5                   10                  15

Gly Ile Ser Pro Cys Val Leu Ser Glu Ala Gly Phe Val Phe Thr Gly
            20                  25                  30

Lys Gln Asp Thr Val Gln Cys Phe Ser Cys Gly Gly Cys Leu Gly
        35                  40                  45

(2) INFORMATION FOR SEQ ID NO: 14:

(i) SEQUENCE CHARACTERISTICS:
    (A) LENGTH: 45 amino acids
    (B) TYPE: amino acid
    (C) STRANDEDNESS: <Unknown>
    (D) TOPOLOGY: linear (ii) MOLECULE TYPE: protein (xi) SEQUENCE DESCRIPTION: SEQ ID NO: 14:

Glu Ala Asn Arg Leu Val Thr Phe Lys Asp Trp Pro Asn Pro Asn Ile
1               5                   10                  15

Thr Pro Gln Ala Leu Ala Lys Ala Gly Phe Tyr Tyr Leu Asn Arg Leu
            20                  25                  30

Asp His Val Lys Cys Val Trp Cys Asn Gly Val Ile Ala
        35                  40                  45

(2) INFORMATION FOR SEQ ID NO: 15:

(i) SEQUENCE CHARACTERISTICS:
        (A) LENGTH: 46 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 15:

Glu Glu Ala Arg Leu Lys Ser Phe Gln Asn Trp Pro Asp Tyr Ala His
1               5                   10                  15

Leu Thr Pro Arg Glu Leu Ala Ser Ala Gly Leu Tyr Tyr Thr Gly Ile
            20                  25                  30

Gly Asp Gln Val Gln Cys Phe Cys Cys Gly Gly Lys Leu Lys
        35                  40                  45

(2) INFORMATION FOR SEQ ID NO: 16:

(i) SEQUENCE CHARACTERISTICS:
        (A) LENGTH: 46 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 16:

Glu Glu Ala Arg Leu Lys Ser Phe Gln Asn Trp Pro Asp Tyr Ala His
1               5                   10                  15

Leu Thr Pro Arg Glu Leu Ala Ser Ala Gly Leu Tyr Tyr Thr Gly Ala
            20                  25                  30

Asp Asp Gln Val Gln Cys Phe Cys Cys Gly Gly Lys Leu Glu
        35                  40                  45

(2) INFORMATION FOR SEQ ID NO: 17:

(i) SEQUENCE CHARACTERISTICS:
        (A) LENGTH: 45 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 17:

Glu Asn Ala Arg Leu Leu Thr Phe Gln Thr Trp Pro Leu Thr Phe Leu
1               5                   10                  15

```
Ser Pro Thr Asp Leu Ala Arg Ala Gly Phe Tyr Tyr Thr Gly Pro Gly
        20                  25                  30

Asp Arg Val Ala Cys Phe Ala Cys Gly Gly Lys Leu Ser
        35                  40                  45

(2) INFORMATION FOR SEQ ID NO: 18:

(i) SEQUENCE CHARACTERISTICS:
        (A) LENGTH: 45 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 18:

Glu Glu Ala Arg Phe Leu Thr Tyr His Met Trp Pro Leu Thr Phe Leu
1               5                   10                  15

Ser Pro Ser Glu Leu Ala Arg Ala Gly Phe Tyr Tyr Ile Gly Pro Gly
        20                  25                  30

Asp Arg Val Ala Cys Phe Ala Cys Gly Gly Lys Leu Ser
        35                  40                  45

(2) INFORMATION FOR SEQ ID NO: 19:

(i) SEQUENCE CHARACTERISTICS:
        (A) LENGTH: 46 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 19:

Glu Glu Ala Arg Leu Lys Ser Phe Gln Asn Trp Pro Asp Tyr Ala His
1               5                   10                  15

Leu Thr Pro Arg Glu Leu Ala Ser Ala Gly Leu Tyr Tyr Thr Gly Ile
        20                  25                  30

Gly Asp Gln Val Gln Cys Phe Cys Cys Gly Gly Lys Leu Lys
        35                  40                  45

(2) INFORMATION FOR SEQ ID NO: 20:

(i) SEQUENCE CHARACTERISTICS:
        (A) LENGTH: 45 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 20:

Glu Ala Asn Arg Leu Val Thr Phe Lys Asp Trp Pro Asn Pro Asn Ile
1               5                   10                  15

Thr Pro Gln Ala Leu Ala Lys Ala Gly Phe Tyr Tyr Leu Asn Arg Leu
        20                  25                  30

Asp His Val Lys Cys Val Trp Cys Asn Gly Val Ile Ala
        35                  40                  45

(2) INFORMATION FOR SEQ ID NO: 21:

(i) SEQUENCE CHARACTERISTICS:
        (A) LENGTH: 50 amino acids
        (B) TYPE: amino acid
```

(C) STRANDEDNESS: <Unknown>
        (D) TOPOLOGY: linear (ii) MOLECULE TYPE: protein (xi) SEQUENCE DESCRIPTION: SEQ ID NO: 21:

Tyr Val Gly Ile Gly Asp Lys Val Lys Cys Phe His Cys Asp Gly Gly
1               5                   10                  15

Leu Arg Asp Trp Glu Pro Gly Asp Asp Pro Trp Glu Glu His Ala Lys
            20                  25                  30

Trp Phe Pro Arg Cys Glu Phe Leu Leu Leu Ala Lys Gly Gln Glu Tyr
        35                  40                  45

Val Ser
50

(2) INFORMATION FOR SEQ ID NO: 22:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 22:

Tyr Val Asp Arg Asn Asp Asp Val Lys Cys Phe Cys Asp Gly Gly
1               5                   10                  15

Leu Arg Cys Trp Glu Pro Gly Asp Asp Pro Trp Ile Glu His Ala Lys
            20                  25                  30

Trp Phe Pro Arg Cys Glu Phe Leu Ile Arg Met Lys Gly Gln Glu Phe
        35                  40                  45

Val Asp
50

(2) INFORMATION FOR SEQ ID NO: 23:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 23:

Tyr Gln Lys Ile Gly Asp Gln Val Arg Cys Phe His Cys Asn Ile Gly
1               5                   10                  15

Leu Arg Ser Trp Gln Lys Glu Asp Glu Pro Trp Phe Glu His Ala Lys
            20                  25                  30

Trp Ser Pro Lys Cys Gln Phe Val Leu Leu Ala Lys Gly Pro Ala Tyr
        35                  40                  45

Val Ser
50

(2) INFORMATION FOR SEQ ID NO: 24:

(i) SEQUENCE CHARACTERISTICS:
        (A) LENGTH: 49 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 24:

Tyr Thr Gly Tyr Gly Asp Asn Thr Lys Cys Phe Tyr Cys Asp Gly Gly
1               5                   10                  15

Leu Lys Asp Trp Glu Pro Glu Asp Val Pro Trp Glu Gln His Val Arg
            20                  25                  30

Trp Phe Asp Arg Cys Ala Tyr Val Gln Leu Val Lys Gly Arg Asp Tyr
        35                  40                  45

Val (2) INFORMATION FOR SEQ ID NO: 25:

(i) SEQUENCE CHARACTERISTICS:
        (A) LENGTH: 49 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 25:

Tyr Thr Gly Gln Gly Asp Lys Thr Arg Cys Phe Cys Cys Asp Gly Gly
1               5                   10                  15

Leu Lys Asp Trp Glu Pro Asp Asp Ala Pro Trp Gln Gln His Ala Arg
            20                  25                  30

Trp Tyr Asp Arg Cys Glu Tyr Val Leu Leu Val Lys Gly Arg Asp Phe
        35                  40                  45

Val (2) INFORMATION FOR SEQ ID NO: 26:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 26:

Tyr Thr Gly Ile Lys Asp Ile Val Gln Cys Phe Ser Cys Gly Gly Cys
1               5                   10                  15

Leu Glu Lys Trp Gln Glu Gly Asp Asp Pro Leu Asp Asp His Thr Arg
            20                  25                  30

Cys Phe Pro Asn Cys Pro Phe Leu Gln Asn Met Lys Ser Ser Ala Glu
        35                  40                  45

Val Thr
    50

(2) INFORMATION FOR SEQ ID NO: 27:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 27:

Tyr Gln Lys Ile Gly Asp Gln Val Arg Cys Phe His Cys Asn Ile Gly
1               5                   10                  15

```
Leu Arg Ser Trp Gln Lys Glu Asp Glu Pro Trp Phe Glu His Ala Lys
            20                  25                  30

Trp Ser Pro Lys Cys Gln Phe Val Leu Ala Lys Gly Pro Ser Tyr
        35                  40                  45

Val Ser
    50

(2) INFORMATION FOR SEQ ID NO: 28:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 28:

Ala Leu Gly Glu Gly Asp Lys Val Lys Cys Phe His Cys Gly Gly
1               5                   10                  15

Leu Thr Asp Trp Lys Pro Ser Glu Asp Pro Trp Glu Gln His Ala Lys
            20                  25                  30

Trp Tyr Pro Gly Cys Lys Tyr Leu Leu Glu Gln Lys Gly Gln Glu Tyr
        35                  40                  45

Ile Asn
    50

(2) INFORMATION FOR SEQ ID NO: 29:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 29:

Ala Leu Gly Glu Gly Asp Lys Val Lys Cys Phe His Cys Gly Gly
1               5                   10                  15

Leu Thr Asp Trp Lys Pro Ser Glu Asp Pro Trp Glu Gln His Ala Lys
            20                  25                  30

Trp Tyr Pro Gly Cys Lys Tyr Leu Leu Asp Glu Lys Gly Gln Glu Tyr
        35                  40                  45

Ile Asn
    50

(2) INFORMATION FOR SEQ ID NO: 30:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 30:

Tyr Val Gly Asn Ser Asp Asp Val Lys Cys Phe Cys Cys Asp Gly Gly
1               5                   10                  15

Leu Arg Cys Trp Glu Ser Gly Asp Asp Pro Trp Val Gln His Ala Lys
            20                  25                  30

Trp Phe Pro Arg Cys Glu Tyr Leu Ile Arg Ile Lys Gly Gln Glu Phe
```

```
                    35                  40                  45
Ile Arg
    50

(2) INFORMATION FOR SEQ ID NO: 31:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 31:

Tyr Val Gly Arg Asn Asp Asp Val Lys Cys Phe Gly Cys Asp Gly Gly
1               5                  10                  15

Leu Arg Cys Trp Glu Ser Gly Asp Asp Pro Trp Val Glu His Ala Lys
                20                  25                  30

Trp Phe Pro Arg Cys Glu Phe Leu Ile Arg Met Lys Gly Gln Glu Phe
                35                  40                  45

Val Asp
    50

(2) INFORMATION FOR SEQ ID NO: 32:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 32:

Ala Leu Gly Glu Gly Asp Lys Val Lys Cys Phe His Cys Gly Gly Gly
1               5                  10                  15

Leu Thr Asp Trp Lys Pro Ser Glu Asp Pro Trp Glu Gln His Ala Lys
                20                  25                  30

Trp Tyr Pro Gly Cys Lys Tyr Leu Leu Glu Gln Lys Gly Gln Glu Tyr
                35                  40                  45

Ile Asn
    50

(2) INFORMATION FOR SEQ ID NO: 33:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 33:

Tyr Gln Lys Ile Gly Asp Gln Val Arg Cys Phe His Cys Asn Ile Gly
1               5                  10                  15

Leu Arg Ser Trp Gln Lys Glu Asp Glu Pro Trp Phe Glu His Ala Lys
                20                  25                  30

Trp Ser Pro Lys Cys Gln Phe Val Leu Leu Ala Lys Gly Pro Ala Tyr
                35                  40                  45

Val Ser
    50
```

(2) INFORMATION FOR SEQ ID NO: 34:

(i) SEQUENCE CHARACTERISTICS:
        (A) LENGTH: 142 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 34:

```
Met Gly Ala Pro Thr Leu Pro Pro Ala Trp Gln Pro Phe Leu Lys Asp
 1               5                  10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
50                  55                  60

Glu Gly Trp Glu Pro Asp Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140
```

(2) INFORMATION FOR SEQ ID NO: 35:

(i) SEQUENCE CHARACTERISTICS:
        (A) LENGTH: 14796 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

```
TCTAGACATG CGGATATATT CAAGCTGGGC ACAGCACAGC AGCCCCACCC CAGGCAGCTT    60

GAAATCAGAG CTGGGGTCCA AAGGGACCAC ACCCCGAGGG ACTGTGTGGG GGTCGGGGCA   120

CACAGGCCAC TGCTTCCCCC CGTCTTTCTC AGCCATTCCT GAAGTCAGCC TCACTCTGCT   180

TCTCAGGGAT TTCAAATGTG CAGAGACTCT GGCACTTTTG TAGAAGCCCC TTCTGGTCCT   240

AACTTACACC TGGATGCTGT GGGGCTGCAG CTGCTGCTCG GCTCGGGAG GATGCTGGGG    300

GCCCGGTGCC CATGAGCTTT TGAAGCTCCT GGAACTCGGT TTTGAGGGTG TTCAGGTCCA   360

GGTGGACACC TGGGCTGTCC TTGTCCATGC ATTTGATGAC ATTGTGTGCA GAAGTGAAAA   420

GGAGTTAGGC CGGGCATGCT GGCTTATGCC TGTAATCCCA GCACTTTGGG AGGCTGAGGC   480

GGGTGGATCA CGAGGTCAGG AGTTCAATAC CAGCCTGGCC AAGATGGTGA AACCCCGTCT   540

CTACTAAAAA TACAAAAAAA TTAGCCGGGC ATGGTGGCGG GCGCATGTAA TCCCAGCTAC   600

TGGGGGGGCT GAGGCAGAGA ATTGCTGGAA CCCAGGAGAT GGAGGTTGCA GTGAGCCAAG   660

ATTGTGCCAC TGCACTGCAC TCCAGCCTGG CGACAGAGCA AGACTCTGTC TCAAAAAAAA   720

AAAAAAAAAG TGAAAAGGAG TTGTTCCTTT CCTCCCTCCT GAGGGCAGGC AACTGCTGCG   780
```

```
GTTGCCAGTG GAGGTGGTGC GTCCTTGGTC TGTGCCTGGG GGCCACCCCA GCAGAGGCCA    840

TGGTGGTGCC AGGGCCCGGT TAGCGAGCCA ATCAGCAGGA CCCAGGGGCG ACCTGCCAAA    900

GTCAACTGGA TTTGATAACT GCAGCGAAGT TAAGTTTCCT GATTTTGATG ATTGTGTTGT    960

GGTTGTGTAA GAGAATGAAG TATTTCGGGG TAGTATGGTA ATGCCTTCAA CTTACAAACG   1020

GTTCAGGTAA ACCACCCATA TACATACATA TACATGCATG TGATATATAC ACATACAGGG   1080

ATGTGTGTGT GTTCACATAT ATGAGGGGAG AGAGACTAGG GGAGAGAAAG TAGGTTGGGG   1140

AGAGGGAGAG AGAAAGGAAA ACAGGAGACA GAGAGAGAGC GGGGAGTAGA GAGAGGGAAG   1200

GGGTAAGAGA GGGAGAGGAG GAGAGAAAGG GAGGAAGAAG CAGAGAGTGA ATGTTAAAGG   1260

AAACAGGCAA AACATAAACA GAAAATCTGG GTGAAGGGTA TATGAGTATT CTTTGTACTA   1320

TTCTTGCAAT TATCTTTTAT TTAAATTGAC ATCGGGCCGG GCGCAGTGGC TCACATCTGT   1380

AATCCCAGCA CTTTGGGAGG CCGAGGCAGG CAGATCACTT GAGGTCAGGA GTTTGAGACC   1440

AGCCTGGCAA ACATGGTGAA ACCCCATCTC TACTAAAAAT ACAAAAATTA GCCTGGTGTG   1500

GTGGTGCATG CCTTTAATCT CAGCTACTCG GGAGGCTGAG GCAGGAGAAT CGCTTGAACC   1560

CGTGGCGGGG AGGAGGTTGC AGTGAGCTGA GATCATGCCA CTGCACTCCA GCCTGGGCGA   1620

TAGAGCGAGA CTCAGTTTCA AATAAATAAA TAAACATCAA AATAAAAAGT TACTGTATTA   1680

AAGAATGGGG GCGGGGTGGG AGGGGTGGGG AGAGGTTGCA AAAATAAATA AATAAATAAA   1740

TAAACCCCAA AATGAAAAAG ACAGTGGAGG CACCAGGCCT GCGTGGGGCT GGAGGGCTAA   1800

TAAGGCCAGG CCTCTTATCT CTGGCCATAG AACCAGAGAA GTGAGTGGAT GTGATGCCCA   1860

GCTCCAGAAG TGACTCCAGA ACACCCTGTT CCAAAGCAGA GGACACACTG ATTTTTTTTT   1920

TAATAGGCTG CAGGACTTAC TGTTGGTGGG ACGCCCTGCT TTGCGAAGGG AAAGGAGGAG   1980

TTTGCCCTGA GCACAGGCCC CCACCCTCCA CTGGGCTTTC CCCAGCTCCC TTGTCTTCTT   2040

ATCACGGTAG TGGCCCAGTC CCTGGCCCCT GACTCCAGAA GGTGGCCCTC CTGGAAACCC   2100

AGGTCGTGCA GTCAACGATG TACTCGCCGG GACAGCGATG TCTGCTGCAC TCCATCCCTC   2160

CCCTGTTCAT TTGTCCTTCA TGCCCGTCTG GAGTAGATGC TTTTTGCAGA GGTGGCACCC   2220

TGTAAAGCTC TCCTGTCTGA CTTTTTTTTT TTTTTAGAC TGAGTTTTGC TCTTGTTGCC   2280

TAGGCTGGAG TGCAATGGCA CAATCTCAGC TCACTGCACC CTCTGCCTCC CGGGTTCAAG   2340

CGATTCTCCT GCCTCAGCCT CCCGAGTAGT TGGGATTACA GGCATGCACC ACCACGCCCA   2400

GCTAATTTTT GTATTTTTAG TAGAGACAAG GTTTCACCGT GATGGCCAGG CTGGTCTTGA   2460

ACTCCAGGAC TCAAGTGATG CTCCTGCCTA GGCCTCTCAA AGTGTTGGGA TTACAGGCGT   2520

GAGCCACTGC ACCCGGCCTG CACGCGTTCT TTGAAAGCAG TCGAGGGGC GCTAGGTGTG   2580

GGCAGGGACG AGCTGGCGCG GCGTCGCTGG GTGCACCGCG ACCACGGGCA GAGCCACGCG   2640

GCGGGAGGAC TACAACTCCC GGCACACCCC GCGCCGCCCC GCCTCTACTC CCAGAAGGCC   2700

GCGGGGGGTG GACCGCCTAA GAGGGCGTGC GCTCCCGACA TGCCCCGCGG CGCGCCATTA   2760

ACCGCCAGAT TTGAATCGCG GGACCCGTTG GCAGAGGTGG CGGCGGCGGC ATGGGTGCCC   2820

CGACGTTGCC CCCTGCCTGG CAGCCCTTTC TCAAGGACCA CCGCATCTCT ACATTCAAGA   2880

ACTGGCCCTT CTTGGAGGGC TGCGCCTGCA CCCCGGAGCG GGTGAGACTG CCCGCCTCC   2940

TGGGGTCCCC CACGCCCGCC TTGCCCTGTC CCTAGCGAGG CCACTGTGAC TGGGCCTCGG   3000

GGGTACAAGC CGCCCTCCCC TCCCCGTCCT GTCCCCAGCG AGGCCACTGT GGCTGGGCCC   3060

CTTGGGTCCA GGCCGGCCTC CCCTCCCTGC TTTGTCCCCA TCGAGGCCTT TGTGGCTGGG   3120
```

-continued

```
CCTCGGGGTT CCGGGCTGCC ACGTCCACTC ACGAGCTGTG CTGTCCCTTG CAGATGGCCG    3180
AGGCTGGCTT CATCCACTGC CCCACTGAGA ACGAGCCAGA CTTGGCCCAG TGTTTCTTCT    3240
GCTTCAAGGA GCTGGAAGGC TGGGAGCCAG ATGACGACCC CATGTAAGTC TTCTCTGGCC    3300
AGCCTCGATG GGCTTTGTTT TGAACTGAGT TGTCAAAAGA TTTGAGTTGC AAAGACACTT    3360
AGTATGGGAG GGTTGCTTTC CACCCTCATT GCTTCTTAAA CAGCTGTTGT GAACGGATAC    3420
CTCTCTATAT GCTGGTGCCT TGGTGATGCT TACAACCTAA TTAAATCTCA TTTGACCAAA    3480
ATGCCTTGGG GTGGACGTAA GATGCCTGAT GCCTTTCATG TTCAACAGAA TACATCAGCA    3540
GACCCTGTTG TTGTGAACTC CCAGGAATGT CCAAGTGCTT TTTTTGAGAT TTTTTAAAAA    3600
ACAGTTTAAT TGAAATATAA CCTACACAGC ACAAAAATTA CCCTTTGAAA GTGTGCACTT    3660
CACACTTTCG GAGGCTGAGG CGGGCGGATC ACCTGAGGTC AGGAGTTCAA GACCTGCCTG    3720
GCCAACTTGG CGAAACCCCG TCTCTACTAA AAATACAAAA ATTAGCCGGG CATGGTAGCG    3780
CACGCCCGTA ATCCCAGCTA CTCGGGAGGC TAAGGCAGGA GAATCGCTTG AACCTGGGAG    3840
GCGGAGGTTG CAGTGAGCCG AGATTGTGCC AATGCACTCC AGCCTCGGCG ACAGAGCGAG    3900
ACTCCGTCAT AAAAATAAAA AATTGAAAAA AAAAAAAGAA AGAAAGCATA TACTTCAGTG    3960
TTGTTCTGGA TTTTTTTCTT CAAGATGCCT AGTTAATGAC AATGAAATTC TGTACTCGGA    4020
TGGTATCTGT CTTTCCACAC TGTAATGCCA TATTCTTTTC TCACCTTTTT TTCTGTCGGA    4080
TTCAGTTGCT TCCACAGCTT TAATTTTTTT CCCCTGGAGA ATCACCCCAG TTGTTTTTCT    4140
TTTTGGCCAG AAGAGAGTAG CTGTTTTTTT TCTTAGTATG TTTGCTATGG TGGTTATACT    4200
GCATCCCCGT AATCACTGGG AAAAGATCAG TGGTATTCTT CTTGAAAATG AATAAGTGTT    4260
ATGATATTTT CAGATTAGAG TTACAACTGG CTGTCTTTTT GGACTTTGTG TGGCCATGTT    4320
TTCATTGTAA TGCAGTTCTG GTAACGGTGA TAGTCAGTTA TACAGGGAGA CTCCCCTAGC    4380
AGAAAATGAG AGTGTGAGCT AGGGGGTCCC TTGGGGAACC CGGGGCAATA ATGCCCTTCT    4440
CTGCCCTTAA TCCTTACAGT GGGCCGGGCA CGGTGGCTTA CGCCTGTAAT ACCAGCACTT    4500
TGGGAGGCCG AGGCGGGCGG ATCACGAGGT CAGGAGATCG AGACCATCTT GGCTAATACG    4560
GTGAAACCCC GTCTCCACTA AAAATACAAA AAATTAGCCG GGCGTGGTGG TGGGCGCCTG    4620
TAGTCCCAGC TACTCGGGAG GCTGAGGCAG GAGAATGGCG TGAACCCAGG AGGCGGAGCT    4680
TGCAGTGAGC CGAGATTGCA CCACTGCACT CCAGCCTGGG CGACAGAATG AGACTCCGTC    4740
TCAAAAAAAA AAAAAAAAGA AAAAAATCTT TACAGTGGAT TACATAACAA TTCCAGTGAA    4800
ATGAAATTAC TTCAAACAGT TCCTTGAGAA TGTTGGAGGG ATTTGACATG TAATTCCTTT    4860
GGACATATAC CATGTAACAC TTTTCCAACT AATTGCTAAG GAAGTCCAGA TAAAATAGAT    4920
ACATTAGCCA CACAGATGTG GGGGGAGATG TCCACAGGGA GAGAGAAGGT GCTAAGAGGT    4980
GCCATATGGG AATGTGGCTT GGGCAAAGCA CTGATGCCAT CAACTTCAGA CTTGACGTCT    5040
TACTCCTGAG GCAGAGCAGG GTGTGCCTGT GGAGGGCGTG GGGAGGTGGC CCGTGGGGAG    5100
TGGACTGCCG CTTTAATCCC TTCAGCTGCC TTTCCGCTGT TGTTTTGATT TTTCTAGAGA    5160
GGAACATAAA AAGCATTCGT CCGGTTGCGC TTTCCTTTCT GTCAAGAAGC AGTTTGAAGA    5220
ATTAACCCTT GGTGAATTTT TGAAACTGGA CAGAGAAAGA GCCAAGAACA AAATTGTATG    5280
TATTGGGAAT AAGAACTGCT CAAACCCTGT TCAATGTCTT TAGCACTAAA CTACCTAGTC    5340
CCTCAAAGGG ACTCTGTGTT TTCCTCAGGA AGCATTTTTT TTTTTTTTCT GAGATAGAGT    5400
TTCACTCTTT TTGCCCAGGC TGGAGTGCAA TGGTGCAATC TTGGCTCACT GCAACCTCTG    5460
CCTCTCGGGT TCAAGTGATT CTCCTGCCTC AGCCTCCCAA GTAACTGGGA TTACAGGGAA    5520
```

```
GTGCCACCAC ACCCAGCTAA TTTTTGTATT TTTAGTAGAG ATGGGGTTTC ACCACATTGC    5580

CCAGGCTGGT CTTGAACTCC TGACCTCGTG ATTCGCCCAC CTTGGCCTCC CAAAGTGCTG    5640

GGATTACAGG CGTGAACCAC CACGCCTGGC TTTTTTTTTT TTGTTCTGAG ACACAGTTTC    5700

ACTCTGTTAC CCAGGCTGGA GTAGGGTGGC CTGATCTCGG ATCACTGCAA CCTCCGCCTC    5760

CTGGGCTCAA GTGATTTGCC TGCTTCAGCC TCCCAAGTAG CCGAGATTAC AGGCATGTGC    5820

CACCACACCC AGGTAATTTT TGTATTTTTG GTAGAGACGA GGTTTCACCA TGTTGGCCAG    5880

GCTGGTTTTG AACTCCTGAC CTCAGGTGAT CCACCCGCCT CAGCCTCCCA AAGTGCTGAG    5940

ATTATAGGTG TGAGCCACCA CACCTGGCCT CAGGAAGTAT TTTTATTTTT AAATTTATTT    6000

ATTTATTTGA GATGGAGTCT TGCTCTGTCG CCCAGGCTAG AGTGCAGCGA CGGGATCTCG    6060

GCTCACTGCA AGCTCCGCCC CCCAGGTTCA AGCCATTCTC CTGCCTCAGC CTCCCGAGTA    6120

GCTGGGACTA CAGGCGCCCG CCACCACACC CGGCTAATTT TTTTGTATTT TTAGTAGAGA    6180

CGGGTTTTCA CCGTGTTAGC CAGGAGGGTC TTGATCTCCT GACCTCGTGA TCTGCCTGCC    6240

TCGGCCTCCC AAAGTGCTGG GATTACAGGT GTGAGCCACC ACACCCGGCT ATTTTTATTT    6300

TTTTGAGACA GGGACTCACT CTGTCACCTG GCTGCAGTG CAGTGGTACA CCATAGCTCA    6360

CTGCAGCCTC GAACTCCTGA GCTCAAGTGA TCCTCCCACC TCATCCTCAC AAGTAATTGG    6420

GACTACAGGT GCACCCCACC ATGCCCACCT AATTTATTTA TTTATTTATT TATTTATTTT    6480

CATAGAGATG AGGGTTCCCT GTGTTGTCCA GGCTGGTCTT GAACTCCTGA GCTCACGGGA    6540

TCCTTTTGCC TGGGCCTCCC AAAGTGCTGA GATTACAGGC ATGAGCCACC GTGCCCAGCT    6600

AGGAATCATT TTTAAAGCCC CTAGGATGTC TGTGTGATTT TAAAGCTCCT GGAGTGTGGC    6660

CGGTATAAGT ATATACCGGT ATAAGTAAAT CCCACATTTT GTGTCAGTAT TTACTAGAAA    6720

CTTAGTCATT TATCTGAAGT TGAAATGTAA CTGGGCTTTA TTTATTTATT TATTTATTTA    6780

TTTATTTTTA ATTTTTTTT TTGAGACGAG TCTCACTTTG TCACCCAGGC TGGAGTGCAG    6840

TGGCACGATC TCGGCTCACT GCAACCTCTG CCTCCCGGGG TCAAGCGATT CTCCTGCCTT    6900

AGCCTCCCGA GTAGCTGGGA CTACAGGCAC GCACCACCAT GCCTGGCTAA TTTTTGTATT    6960

TTTAGTAGAC GGGGTTTCAC CATGCTGGCC AAGCTGGTCT CAAACTCCTG ACCTTGTGAT    7020

CTGCCCGCTT TAGCCTCCCA GAGTGCTGGG ATTACAGGCA TGAGCCACCA TGCGTGGTCT    7080

TTTTAAAATT TTTTGATTTT TTTTTTTTTT GAGACAGAGC CTTGCTCTGT CGCCCAGGCT    7140

GGAGTGCAGT GGCACGATCT CAGCTCACTA CAAGCTCCGC CTCCCGGGTT CACGCCATTC    7200

TTCTGCCTCA GCCTCCTGAG TAGCTGGGAC TACAGGTGCC CACCACCACG CCTGGCTAAT    7260

TTTTTTTGGT ATTTTTATTA GAGACAAGGT TTCATCATGT TGGCCAGGCT GGTCTCAAAC    7320

TCCTGACCTC AAGTGATCTG CCTGCCTCGG CCTCCCAAAG CGCTGAGATT ACAGGTGTGA    7380

TCTACTGCGC CAGGCCTGGG CGTCATATAT TCTTATTTGC TAAGTCTGGC AGCCCCACAC    7440

AGAATAAGTA CTGGGGGATT CCATATCCTT GTAGCAAAGC CCTGGGTGGA GAGTCAGGAG    7500

ATGTTGTAGT TCTGTCTCTG CCACTTGCAG ACTTTGAGTT TAAGCCAGTC GTGCTCATGC    7560

TTTCCTTGCT AAATAGAGGT TAGACCCCCT ATCCCATGGT TTCTCAGGTT GCTTTTCAGC    7620

TTGAAAATTG TATTCCTTTG TAGAGATCAG CGTAAAATAA TTCTGTCCTT ATATGTGGCT    7680

TTATTTTAAT TTGAGACAGA GTGTCACTCA GTCGCCCAGG CTGGAGTGTG GTGGTGCGAT    7740

CTTGGCTCAC TGCGACCTCC ACCTCCCAGG TTCAAGCGAT TCTCGTGCCT CAGGCTCCCA    7800

AGTAGCTGAG ATTATAGGTG TGTGCCACCA GGCCCAGCTA ACTTTGTAT TTTTAGTAGA    7860
```

| | |
|---|---|
| GACAGGGTTT TGCCATGTTG GCTAAGCTGG TCTCGAACTC CTGGCCTCAA GTGATCTGCC | 7920 |
| CGCCTTGGCA TCCCAAAGTG CTGGGATTAC AGGTGTGAAC CACCACACCT GGCCTCAATA | 7980 |
| TAGTGGCTTT TAAGTGCTAA GGACTGAGAT TGTGTTTTGT CAGGAAGAGG CCAGTTGTGG | 8040 |
| GTGAAGCATG CTGTGAGAGA GCTTGTCACC TGGTTGAGGT TGTGGGAGCT GCAGCGTGGG | 8100 |
| AACTGGAAAG TGGGCTGGGG ATCATCTTTT TCCAGGTCAG GGGTCAGCCA GCTTTTCTGC | 8160 |
| AGCGTGCCAT AGACCATCTC TTAGCCCTCG TGGGTCAGAG TCTCTGTTGC ATATTGTCTT | 8220 |
| TTGTTGTTTT TCACAACCTT TTAGAAACAT AAAAAGCATT CTTAGCCCGT GGGCTGGACA | 8280 |
| AAAAAAGGCC ATGACGGGCT GTATGGATTT GGCCCAGCAG GCCCTTGCTT GCCAAGCCCT | 8340 |
| GTTTTAGACA AGGAGCAGCT TGTGTGCCTG GAACCATCAT GGGCACAGGG GAGGAGCAGA | 8400 |
| GTGGATGTGG AGGTGTGAGC TGGAAACCAG GTCCCAGAGC GCTGAGAAAG ACAGAGGGTT | 8460 |
| TTTGCCCTTG CAAGTAGAGC AACTGAAATC TGACACCATC CAGTTCCAGA AAGCCCTGAA | 8520 |
| GTGCTGGTGG ACGCTGCGGG TGCTCCGCT CTAGGGTTAC AGGGATGAAG ATGCAGTCTG | 8580 |
| GTAGGGGGAG TCCACTCACC TGTTGGAAGA TGTGATTAAG AAAAGTAGAC TTTCAGGGCC | 8640 |
| GGGCATGGTG GCTCACGCCT GTAATCCCAG CACTTTGGGA GGCCGAGGCG GGTGGATCAC | 8700 |
| GAGGTCAGGA GATCGAGACC ATCCTGGCTA ACATGGTGAA ACCCCGTCTT TACTAAAAAT | 8760 |
| ACAAAAAATT AGCTGGGCGT GGTGGCGGGC GCCTGTAGTC CCAGCTACTC GGGAGGCTGA | 8820 |
| GGCAGGAGAA TGGCGTGAAC CTGGGAGGTG GAGCTTGCTG TGAGCCGAGA TCGCGCCACT | 8880 |
| GCACTCCAGC CTGGGCGACA GAGCGAGACT CCGTCTCAAA AAAAAAAAAA AAAGTAGGCT | 8940 |
| TTCATGATGT GTGAGCTGAA GGCGCAGTAG GCAGAAGTAG AGGCCTCAGT CCCTGCAGGA | 9000 |
| GACCCCTCGG TCTCTATCTC CTGATAGTCA GACCCAGCCA CACTGGAAAG AGGGGAGACA | 9060 |
| TTACAGCCTG CGAGAAAAGT AGGGAGATTT AAAAACTGCT TGGCTTTTAT TTTGAACTGT | 9120 |
| TTTTTTTGTT TGTTTGTTTT CCCCAATTCA GAATACAGAA TACTTTTATG GATTTGTTTT | 9180 |
| TATTACTTTA ATTTTGAAAC AATATAATCT TTTTTTTGTT GTTTTTTTGA GACAGGGTCT | 9240 |
| TACTCTGTCA CCCAGGCTGA GTGCAGTGGT GTGATCTTGG CTCACCTCAG CCTCGACCCC | 9300 |
| CTGGGCTCAA ATGATTCTCC CACCTCAGCT TCCCAAGTAG CTGGGACCAC AGGTGCGTGT | 9360 |
| GTTGCGCTAT ACAAATCCTG AAGACAAGGA TGCTGTTGCT GGTGATGCTG GGGATTCCCA | 9420 |
| AGATCCCAGA TTTGATGGCA GGATGCCCCT GTCTGCTGCC TTGCCAGGGT GCCAGGAGGG | 9480 |
| CGCTGCTGTG GAAGCTGAGG CCCGGCCATC CAGGGCGATG CATTGGGCGC TGATTCTTGT | 9540 |
| TCCTGCTGCT GCCTCGGTGC TTAGCTTTTG AAACAATGAA ATAAATTAGA ACCAGTGTGA | 9600 |
| AAATCGATCA GGGAATAAAT TTAATGTGGA AATAAACTGA ACAACTTAGT TCTTCATAAG | 9660 |
| AGTTTACTTG GTAAATACTT GTGATGAGGA CAAAACGAAG CACTAGAAGG AGAGGCGAGT | 9720 |
| TGTAGACCTG GGTGGCAGGA GTGTTTTGTT TGTTTTCTTT GGCAGGGTCT TGCTCTGTTG | 9780 |
| CTCAGGCTGG AGTACAGTGG CACAATCACA GCTCACTATA GCCTCGACCT CCTGGACTCA | 9840 |
| AGCAATCCTC CTGCCTCAGC CTCCCAGTAG CTGGGACTAC AGGCGCATGC CACCATGCCT | 9900 |
| GGCTAATTTT AAATTTTTTT TTTTCTCTTT TTTGAGATGG AATCTCACTC TGTCGCCCAG | 9960 |
| GCTGGAGTGC AGTGGCGTGA TCTCGGCTGA CGGCAAGCTC CGCCTCCCAG GTTCACTCCA | 10020 |
| TTCGCCTGCC TCAGCCTCCC AAGTAGCTGG GACTACAGGC GCTGGGATTA CAAACCCAAA | 10080 |
| CCCAAAGTGC TGGGATTACA GGCGTGAGCC ACTGCACCCG GCCTGTTTTG TCTTTCAATA | 10140 |
| GCAAGAGTTG TGTTTGCTTC GCCCCTACCT TTAGTGGAAA AATGTATAAA ATGGAGATAT | 10200 |
| TGACCTCCAC ATTGGGGTGG TTAAATTATA GCATGTATGC AAAGGAGCTT CGCTAATTTA | 10260 |

```
AGGCTTTTTT GAAAGAGAAG AAACTGAATA ATCCATGTGT GTATATATAT TTTAAAAGCC    10320

ATGGTCATCT TTCCATATCA GTAAAGCTGA GGCTCCCTGG GACTGCAGAG TTGTCCATCA    10380

CAGTCCATTA TAAGTGCGCT GCTGGGCCAG GTGCAGTGGC TTGTGCCTGA ATCCCAGCAC    10440

TTTGGGAGGC CAAGGCAGGA GGATTCATTG AGCCCAGGAG TTTTGAGGCG AGCCTGGGCA    10500

ATGTGGCCAG ACCTCATCTC TTCAAAAAAT ACACAAAAAA TTAGCCAGGC ATGGTGGCAC    10560

GTGCCTGTAG TCTCAGCTAC TCAGGAGGCT GAGGTGGGAG GATCACTTTG AGCCTTGCAG    10620

GTCAAAGCTG CAGTAAGCCA TGATCTTGCC ACTGCATTCC AGCCTGGATG ACAGAGCGAG    10680

ACCCTGTCTC TAAAAAAAAA AAAAACCAAA CGGTGCACTG TTTTCTTTTT TCTTATCAAT    10740

TTATTATTTT TAAATTAAAT TTTCTTTTAA TAATTTATAA ATTATAAATT TATATTAAAA    10800

AATGACAAAT TTTTATTACT TATACATGAG GTAAAACTTA GGATATATAA AGTACATATT    10860

GAAAAGTAAT TTTTTGGCTG GCACAGTGGC TCACACCTGT AATCCCAGCA CTTTGGGAGG    10920

CCGTGGCGGG CAGATCACAT GAGATCATGA GTTCGAGACC AACCTGACCA ACATGGAGAG    10980

ACCCCATCTC TACTAAAAAT ACAAAATTAG CCGGGGTGGT GGCGCATGCC TGTAATCCCA    11040

GCTACTCGGG AGGCTGAGGC AGGAGAATCT CTTGAACCCG GGAGGCAGAG GTTGCGGTGA    11100

GCCAAGATCG TGCCTTTGCA CACCAGCCTA GGCAACAAGA GCGAAAGTCC GTCTCAAAAA    11160

AAAAGTAATT TTTTTAAGT TAACCTCTGT CAGCAAACAA ATTTAACCCA ATAAAGGTCT    11220

TTGTTTTTTA ATGTAGTAGA GGAGTTAGGG TTTATAAAAA ATATGGTAGG AAGGGGGTC    11280

CCTGGATTTG CTAATGTGAT TGTCATTTGC CCCTTAGGAG AGAGCTCTGT TAGCAGAATG    11340

AAAAAATTGG AAGCCAGATT CAGGGAGGGA CTGGAAGCAA AAGAATTTCT GTTCGAGGAA    11400

GAGCCTGATG TTTGCCAGGG TCTGTTTAAC TGGACATGAA GAGGAAGGCT CTGGACTTTC    11460

CTCCAGGAGT TTCAGGAGAA AGGTAGGGCA GTGGTTAAGA GCAGAGCTCT GCCTAGACTA    11520

GCTGGGGTGC CTAGACTAGC TGGGGTGCCC AGACTAGCTG GGGTGCCTAG ACTAGCTGGG    11580

TACTTTGAGT GGCTCCTTCA GCCTGGACCT CGGTTTCCTC ACCTGTATAG TAGAGATATG    11640

GGAGCACCCA GCGCAGGATC ACTGTGAACA TAAATCAGTT AATGGAGGAA GCAGGTAGAG    11700

TGGTGCTGGG TGCATACCAA GCACTCCGTC AGTGTTTCCT GTTATTCGAT GATTAGGAGG    11760

CAGCTTAAAC TAGAGGGAGT TGAGCTGAAT CAGGATGTTT GTCCCAGGTA GCTGGGAATC    11820

TGCCTAGCCC AGTGCCCAGT TTATTTAGGT GCTCTCTCAG TGTTCCCTGA TTGTTTTTTC    11880

CTTTGTCATC TTATCTACAG GATGTGACTG GGAAGCTCTG GTTTCAGTGT CATGTGTCTA    11940

TTCTTTATTT CCAGGCAAAG GAAACCAACA ATAAGAAGAA AGAATTTGAG GAAACTGCGA    12000

AGAAAGTGCG CCGTGCCATC GAGCAGCTGG CTGCCATGGA TTGAGGCCTC TGGCCGGAGC    12060

TGCCTGGTCC CAGAGTGGCT GCACCACTTC CAGGGTTTAT TCCCTGGTGC CACCAGCCTT    12120

CCTGTGGGCC CCTTAGCAAT GTCTTAGGAA AGGAGATCAA CATTTTCAAA TTAGATGTTT    12180

CAACTGTGCT CCTGTTTTGT CTTGAAAGTG GCACCAGAGG TGCTTCTGCC TGTGCAGCGG    12240

GTGCTGCTGG TAACAGTGGC TGCTTCTCTC TCTCTCTCTC TTTTTTGGGG GCTCATTTTT    12300

GCTGTTTTGA TTCCCGGGCT TACCAGGTGA GAAGTGAGGG AGGAAGAAGG CAGTGTCCCT    12360

TTTGCTAGAG CTGACAGCTT TGTTCGCGTG GGCAGAGCCT TCCACAGTGA ATGTGTCTGG    12420

ACCTCATGTT GTTGAGGCTG TCACAGTCCT GAGTGTGGAC TTGGCAGGTG CCTGTTGAAT    12480

CTGAGCTGCA GGTTCCTTAT CTGTCACACC TGTGCCTCCT CAGAGGACAG TTTTTTTGTT    12540

GTTGTGTTTT TTTGTTTTTT TTTTTGGTA GATGCATGAC TTGTGTGTGA TGAGAGAATG    12600
```

-continued

```
GAGACAGAGT CCCTGGCTCC TCTACTGTTT AACAACATGG CTTTCTTATT TTGTTTGAAT   12660

TGTTAATTCA CAGAATAGCA CAAACTACAA TTAAAACTAA GCACAAAGCC ATTCTAAGTC   12720

ATTGGGAAA CGGGGTGAAC TTCAGGTGGA TGAGGAGACA GAATAGAGTG ATAGGAAGCG    12780

TCTGGCAGAT ACTCCTTTTG CCACTGCTGT GTGATTAGAC AGGCCCAGTG AGCCGCGGGG   12840

CACATGCTGG CCGCTCCTCC CTCAGAAAAA GGCAGTGGCC TAAATCCTTT TTAAATGACT   12900

TGGCTCGATG CTGTGGGGA CTGGCTGGGC TGCTGCAGGC CGTGTGTCTG TCAGCCCAAC    12960

CTTCACATCT GTCACGTTCT CCACACGGGG GAGAGACGCA GTCCGCCCAG GTCCCGCTT    13020

TCTTTGGAGG CAGCAGCTCC CGCAGGGCTG AAGTCTGGCG TAAGATGATG GATTTGATTC   13080

GCCCTCCTCC CTGTCATAGA GCTGCAGGGT GGATTGTTAC AGCTTCGCTG GAAACCTCTG   13140

GAGGTCATCT CGGCTGTTCC TGAGAAATAA AAAGCCTGTC ATTTCAAACA CTGCTGTGGA   13200

CCCTACTGGG TTTTTAAAAT ATTGTCAGTT TTTCATCGTC GTCCCTAGCC TGCCAACAGC   13260

CATCTGCCCA GACAGCCGCA GTGAGGATGA GCGTCCTGGC AGAGACGCAG TTGTCTCTGG   13320

GCGCTTGCCA GAGCCACGAA CCCCAGACCT GTTTGTATCA TCCGGGCTCC TTCCGGGCAG   13380

AAACAACTGA AAATGCACTT CAGACCCACT TATTTATGCC ACATCTGAGT CGGCCTGAGA   13440

TAGACTTTTC CCTCTAAACT GGGAGAATAT CACAGTGGTT TTTGTTAGCA GAAAATGCAC   13500

TCCAGCCTCT GTACTCATCT AAGCTGCTTA TTTTTGATAT TTGTGTCAGT CTGTAAATGG   13560

ATACTTCACT TTAATAACTG TTGCTTAGTA ATTGGCTTTG TAGAGAAGCT GGAAAAAAAT   13620

GGTTTTGTCT TCAACTCCTT TGCATGCCAG GCGGTGATGT GGATCTCGGC TTCTGTGAGC   13680

CTGTGCTGTG GGCAGGGCTG AGCTGGAGCC GCCCCTCTCA GCCCGCCTGC CACGGCCTTT   13740

CCTTAAAGGC CATCCTTAAA ACCAGACCCT CATGGCTGCC AGCACCTGAA AGCTTCCTCG   13800

ACATCTGTTA ATAAAGCCGT AGGCCCTTGT CTAAGCGCAA CCGCCTAGAC TTTCTTTCAG   13860

ATACATGTCC ACATGTCCAT TTTTCAGGTT CTCTAAGTTG GAGTGGAGTC TGGGAAGGGT   13920

TGTGAATGAG GCTTCTGGGC TATGGGTGAG GTTCCAATGG CAGGTTAGAG CCCCTCGGGC   13980

CAACTGCCAT CCTGGAAAGT AGAGACAGCA GTGCCCGCTG CCCAGAAGAG ACCAGCAAGC   14040

CAAACTGGAG CCCCCATTGC AGGCTGTCGC CATGTGGAAA GAGTAACTCA CAATTGCCAA   14100

TAAAGTCTCA TGTGGTTTTA TCTACTTTTT TTTTCTTTTT CTTTTTTTTT GAGACAAGGC   14160

CTTGCCCTCC CAGGCTGGAG TGCAGTGGAA TGACCACAGC TCACCGCAAC CTCAAATTCT   14220

TGCGTTCAAG TGAACCTCCC ACTTTAGCCT CCCAAGTAGC TGGGACTACA GGCGCACGCC   14280

ATCACACCCG GCTAATTGAA AAATTTTTTT TTTGTTTAG ATGGAATCTC ACTTTGTTGC    14340

CCAGGCTGGT CTCAAACTCC TGGGCTCAAG TGATCATCCT GCTTCAGCGT CCGACTTGTT   14400

GGTATTATAG GCGTGAGCCA CTGGGCCTGA CCTAGCTACC ATTTTTTAAT GCAGAAATGA   14460

AGACTTGTAG AAATGAAATA ACTTGTCCAG GATAGTCGAA TAAGTAACTT TTAGAGCTGG   14520

GATTTGAACC CAGGCAATCT GGCTCCAGAG CTGGCCCTC ACTGCTGAAG GACACTGTCA    14580

GCTTGGGAGG GTGGCTATGG TCGGCTGTCT GATTCTAGGG AGTGAGGGCT GTCTTTAAAG   14640

CACCCCATTC CATTTTCAGA CAGCTTTGTC AGAAAGGCTG TCATATGGAG CTGACACCTG   14700

CCTCCCCAAG GCTTCCATAG ATCCTCTCTG TACATTGTAA CCTTTTATTT TGAAATGAAA   14760

ATTCACAGGA AGTTGTAAGG CTAGTACAGG GGATCC                            14796
```